(12) United States Patent
Duncan et al.

(10) Patent No.: US 7,019,019 B2
(45) Date of Patent: Mar. 28, 2006

(54) MATRIPTASE INHIBITORS AND METHODS OF USE

(75) Inventors: David F. Duncan, San Diego, CA (US); L. Josue Alfaro-Lopez, San Marcos, CA (US); Mallareddy Komandla, San Diego, CA (US); Odile Esther Levy, San Diego, CA (US); Ofir Moreno, Del Mar, CA (US); Joseph E. Semple, San Diego, CA (US); Amir P. Tamiz, San Diego, CA (US)

(73) Assignee: Dendreon Corporation, Seattle, WA (US)

(*) Notice: Subject to any disclaimer, the term of this patent is extended or adjusted under 35 U.S.C. 154(b) by 64 days.

(21) Appl. No.: 10/740,946

(22) Filed: Dec. 18, 2003

(65) Prior Publication Data

US 2004/0186060 A1 Sep. 23, 2004

Related U.S. Application Data

(60) Provisional application No. 60/436,264, filed on Dec. 23, 2002.

(51) Int. Cl.
| | |
|---|---|
| A61K 31/44 | (2006.01) |
| A61K 31/425 | (2006.01) |
| A61K 31/38 | (2006.01) |
| C07D 333/22 | (2006.01) |
| C07D 211/72 | (2006.01) |

(52) U.S. Cl. ........................ 514/352; 514/369; 514/438; 546/312; 548/205; 549/77

(58) Field of Classification Search ................. 514/352, 514/369, 438; 546/312; 548/205; 549/77
See application file for complete search history.

(56) References Cited

U.S. PATENT DOCUMENTS

| | | | |
|---|---|---|---|
| 5,492,895 | A | 2/1996 | Vlasuk et al. |
| 5,534,498 | A | 7/1996 | Brunck et al. |
| 5,658,939 | A | 8/1997 | Abelman et al. |
| 5,681,844 | A | 10/1997 | Abelman et al. |
| 5,696,231 | A | 12/1997 | Abelman et al. |

(Continued)

FOREIGN PATENT DOCUMENTS

| | | |
|---|---|---|
| WO | WO 99/42120 A1 | 8/1999 |
| WO | WO 00/05245 A2 | 2/2000 |
| WO | WO 00/05245 | 2/2000 |
| WO | WO 00/26211 A1 | 5/2000 |
| WO | WO 00/53232 | 9/2000 |

(Continued)

OTHER PUBLICATIONS

Coligan, J. E. et al. (eds.) Current Protocols in Protein Science, John Wiley and Sons, 1997.
Doonan, S. (ed.) Protein Purification Protocols, Humana Press, 1966.
Gennaro, A.R. (ed.) Remington's Pharmaceutical Sciences, Mack Publishing Co., 1985, at p. 1449.

(Continued)

*Primary Examiner*—Deborah C. Lambkin
(74) *Attorney, Agent, or Firm*—Townsend and Townsend and Crew LLP

(57) ABSTRACT

The present invention provides matriptase inhibitors and compositions thereof useful for treating cancer. Martripase is a trypsin-like serine protease active in the development of cancerous conditions, such as tumors and metastasis of cancer.

42 Claims, 2 Drawing Sheets

U.S. PATENT DOCUMENTS

| | | | |
|---|---|---|---|
| 5,703,208 | A | 12/1997 | Semple et al. |
| 5,714,499 | A | 2/1998 | Semple et al. |
| 5,731,413 | A | 3/1998 | Webb et al. |
| 5,739,112 | A | 4/1998 | Brunck et al. |
| 5,770,600 | A | 6/1998 | Abelman et al. |
| 5,883,077 | A | 3/1999 | Brunck et al. |
| 5,886,146 | A | 3/1999 | Vlasuk et al. |
| 5,972,616 | A | 10/1999 | O'Brien et al. |
| 6,025,472 | A | 2/2000 | Abelman et al. |
| 6,034,215 | A | 3/2000 | Semple et al. |
| 6,335,155 | B1 * | 1/2002 | Wells et al. .............. 435/4 |
| 6,392,010 | B1 | 5/2002 | Salvino et al. |
| 6,506,754 | B1 | 1/2003 | Siev et al. |
| 6,586,405 | B2 * | 7/2003 | Semple et al. ............ 514/19 |
| 6,838,074 | B2 * | 1/2005 | Carpenter, Jr. ............ 424/9.1 |

FOREIGN PATENT DOCUMENTS

| | | |
|---|---|---|
| WO | WO 00/53232 A1 | 9/2000 |
| WO | WO 01/29056 A1 | 4/2001 |
| WO | WO 01/57194 | 8/2001 |
| WO | WO 01/57194 A2 | 8/2001 |
| WO | WO 01/97794 | 12/2001 |
| WO | WO 01/97794 A2 | 12/2001 |
| WO | WO 02/08392 A2 | 1/2002 |
| WO | WO 02/08392 | 1/2002 |

OTHER PUBLICATIONS

Bock, P.E. et al., "Isolation of human blood coagulation alpha–factor Xa by soybean trypsin inhibitor–sepharose chromatography and its active–site titration with fluorescein mono–p–guanidinobenzoate" *Arch. Biochem. Biophys.*, vol. 273, pp. 375–388 (1989).

Boring, et al., "Cancer Statistics, 1993" *CA Cancer J. Clin.*, vol. 43, p. 7 (1993).

Brooks et al., "Use of the 10–day–old chick embryo model for studying angiogenesis" *Methods Mol. Biol.*, vol. 129, pp. 257–269 (1999).

Enyedy et al., "Structure–based approach for the discovery of bis–benzamidines as novel inhibitors of matriptase" *J. Med. Chem.*, 44:1349–1355 (2001).

Graham, J. E. et al., "Theoretical studies applied to drug design: ab initio electronic distribution of bioisosteres" *J. Mol. Structure (Theochem)*, vol. 343, pp. 105–109 (1995).

Hunter, T., "Cooperation between oncogenes" *Cell*, vol. 64, No. 2; pp. 249–270 (1991).

Land, et al., "Cellular oncogenes and multistep carcinogenesis" *Science*, vol. 222, p. 771 (1983).

Lin et al., "Purification and characterization of a complex containing matriptase and a Kunitz–type serine protease" *J. Biol. Chem.*, vol. 274, No. 26; pp. 18237–18242 (1999).

Lin et al., "Molecular cloning of cdna for matriptase, a matrix–degrading serine protease with trypsin–like activity" *J. Biol. Chem.*, vol. 274, No. 26; pp. 18231–18236 (1999).

Liotta, et al., "Metastatic potential correlates with enzymatic degradation of basement membrane collagen" *Nature*, vol. 284, pp. 67–68 (1980).

Lipinski, "Bioisosterism in drug design" *Annual Reports in Medicinal Chemistry*, vol. 21, Section VI, Chapter 27, pp. 283–291 (1986).

McDonnell and Matrisian, "Stromelysin in tumor progression and metastasis," *Cancer Metastasis Rev.*, vol. 9, No. 4; pp. 305–319 (1990).

Matrisian and Bowden, "Stromelysin/transin and tumor progression," *Seminars in Cancer Biology*, vol. 1, pp. 107–115 (1990).

Mignatti, et al., "Biology and biochemistry of proteinases in tumor invasion," *Physiol. Rev.*, vol. 73, No. 1; pp. 161–195 (1993).

Ossowski, L., "In vivo invasion of modified chorioallantoic membrane by tumor cells: the role of cell surface–bound urokinase," *J. Cell. Biol.*, vol. 107, No. 6; pp. 2437–2445 (1988).

Ruley, H.E., "Adenovirus early region 1A enables viral and cellular transforming genes to transform primary cells in culture," *Nature*, vol. 304, No. 5927; pp. 602–606 (1983).

Takeuchi, et al., "Cellular localization of membrane–type serine protease 1 and identification of protease–activated receptor–2 and single–chain urokinase–type plasminogen activator as substrates," *J. Biol. Chem.*, vol. 275, No. 34; pp. 26333–26342 (2000).

Tamura, et al. "Novel benzo–fused lactam scaffolds as factor Xa inhibitors" *Bioorg. Med. Chem. Lett.*, vol. 9, No. 17; pp. 2573–2578 (1999).

Yun, S.H., "Application of bioisosterism to new drug design," *Hwahak Sekye*, vol. 33, No. 8; pp. 576–579 (1993) [Korean].

Zhao, G. and H. Yang, "Bioisosteric replacement and development of lead compounds in drug designs" *Huaxue Tongbao*, No. 6, pp. 34–38 (1995) [Chinese].

* cited by examiner

MATRIPTASE INHIBITORS AND METHODS OF USE

CROSS-REFERENCE TO RELATED APPLICATIONS

The present application claims priority to U.S. patent application Ser. No. 60/436,264, filed Dec. 23, 2002, the disclosure of which is hereby incorporated by reference in its entirety for all purposes.

BACKGROUND OF THE INVENTION

Cancer is the second leading cause of death in the United States, after heart disease (Boring et al., *CA Cancer J. Clin.*, 43:7 (1993)), and develops in one in three Americans. One of every four Americans dies of cancer. Cancer is characterized primarily by an increase in the number of abnormal, or neoplastic, cells derived from a given normal tissue which proliferate to form a tumor mass, the invasion of adjacent tissues by these neoplastic tumor cells, and the generation of malignant cells which spread via the blood or lymphatic system to regional lymph nodes and to distant sites. The latter progression to malignancy is referred to as metastasis.

Cancer can be viewed as a breakdown in the communication between tumor cells and their environment, including their normal neighboring cells. Signals, both growth-stimulatory and growth-inhibitory, are routinely exchanged between cells within a tissue. Normally, cells do not divide in the absence of stimulatory signals, and likewise, will cease dividing in the presence of inhibitory signals. In a cancerous, or neoplastic, state, a cell acquires the ability to "override" these signals and to proliferate under conditions in which normal cells would not grow.

Tumor cells must acquire a number of distinct aberrant traits to proliferate. Reflecting this requirement is the fact that the genomes of certain well-studied tumors carry several different independently altered genes, including activated oncogenes and inactivated tumor suppressor genes. Each of these genetic changes appears to be responsible for imparting some of the traits that, in aggregate, represent the full neoplastic phenotype (Land et al., *Science*, 222:771 (1983); Ruley, H. E., *Nature* 304:602 (1983); Hunter, T., *Cell*, 64:249 (1991)).

In addition to unhindered cell proliferation, cells must acquire several traits for tumor progression to occur. For example, early on in tumor progression, cells must evade the host immune system. Further, as tumor mass increases, the tumor must acquire vasculature to supply nourishment and remove metabolic waste. Additionally, cells must acquire an ability to invade adjacent tissue, and, ultimately, cells often acquire the capacity to metastasize to distant sites.

A variety of biochemical factors have been associated with different phases of metastases. Cell surface receptors for collagen, glycoproteins such as laminin, or proteoglycans facilitate tumor cell attachment, an important step in invasion and metastases. Attachment then triggers the release of degradative enzymes which facilitate the penetration of tumor cells through tissue barriers. Once the tumor cells have entered the target tissue, specific growth factors are required for further proliferation.

One of the major characteristics of cancer cells is their ability to invade surrounding normal tissues and metastasize to distant body sites. It is the metastatic nature of malignant tumors that presents a great challenge to clinicians in terms of treatment, since the tumor is no longer localized to one area.

Tumor invasion (or progression) is a complex series of events, in which tumor cells detach from the primary tumor, break down the normal tissue surrounding it, and migrate into a blood or lymphatic vessel to be carried to a distant site. The breaking down of normal tissue barriers is accomplished by the elaboration of specific enzymes that degrade the proteins of the extracellular matrix that make up basement membranes and stromal components of tissues.

Elevated proteolytic activity has been implicated in neoplastic progression. The role(s) of proteolytic enzymes, including serine proteases, in neoplastic progression are under study. Proteases have been proposed to contribute to the degradation of excellular matrix and to tissue remodeling and, thus, may assist in cancer invasion and metastasis.

A number of extracellular proteases have been reported and expression of some of these proteases has been said to correlate with tumor progression. (Mignatti et al., *Physiol. Rev.*, 73:161–195 (1993).)

A class of extracellular matrix degrading enzymes has been identified called the matrix metalloproteinases (MMPs). Two of the matrix metalloproteinases have been implicated in tumor invasion. The type IV collagenase has been correlated with the metastatic potential of tumor cells. (Liotta et al., *Nature*, 284:67–68 (1980)). It has been reported that the production of the matrix metalloproteinase stromelysin was associated with malignant tumors with metastatic potential. (McDonnell and Matrisian, *Smnrs. in Cancer Biology*, 1:107–115 (1990); McDonnell and Matrisian, *Cancer and Metastasis Reviews*, 9:309–319 (1990).)

The capacity of cancer cells to metastasize and invade tissue has been reported to be facilitated by degradation of the basement membrane. Several proteinase enzymes have been reported to facilitate the process of invasion of tumor cells. One family of enzymes, the MMPs, has been implicated as enhancing degradation of the basement membrane to allow tumorous cells to invade tissues. MMPs have been reported to differ in molecular weight and antigenic properties. Previously, two major metalloproteinases having molecular weights of about 70 kDa and 92 kDa have been studied. Both of these MMPs have been reported to enhance ability of tumor cells to metastasize. Two natural inhibitors of these enzymes known as tissue inhibitors of metalloproteinase (TIMP) have been identified. The inactivated unclipped collagenases are generally secreted as a complex with TIMP. Enzymatic activity of the 70 kDa and 92 kDa proteins has been reported to depend on secreted ratios of collagenase/TIMP.

Matriptase is a trypsin-like serine protease has also been isolated and cloned from T-47D human breast cancer cells. Matriptase has been isolated from T-47D cell-conditioned medium. (Lin et al., *J. Biol. Chem.*, 274(26):18231–18236 (1999).) Upon analysis of the cDNA, it was determined that the protease had 683 amino acids and contained three main structural regions: a serine protease domain near the carboxyl-terminal region, four tandem low-density lipoprotein receptor domains, and two tandem complement subcomponents, C1r and C1s. Matriptase was reported to be a mosaic protein with broad spectrum cleavage activity and two potential regulatory modules. It was named "matriptase" because of the ability of the protease to degrade the extra-cellular matrix and its trypsin-like activity. (Lin et al., *J. Bio. Chem.*, 274:18231–18236 (1999).)

Matriptase is reported to be a protease having activity in degrading extracellular matrix that is localized on the cell surface. When isolated from breast cancer cells (or T-47D cell conditioned medium), matriptase has been reported to be primarily in an uncomplexed form. Matriptase has also been isolated from human milk. When isolated from human milk, matriptase was reported to be in one of two complexed forms, 95 kDa (the predominant form) and 110 kDa; uncomplexed matriptase was not detected. (Liu et al., *J. Biol. Chem.*, 274(26):18237–18242 (1999).) It has been proposed that matriptase exists as an uncomplexed protease when in its active state. In breast milk, matriptase has been reported to exist in complex with a fragment of hepatocyte growth factor inhibitor-1 (HAI-1), a Kunitz-type serine protease inhibitor having activity against trypsin-like serine proteases.

Published PCT application WO 00/53232, "Matriptase, a Serine Protease and Its Applications", is said to describe matriptase.

Ecotin and Ecotin M84R/M85R have been reported to be macromolecular inhibitors of serine proteases of the chymotrypsin fold and have been reported to inhibit ductal branching, morphogenesis and differentiation of the explanted ductal prostate. PC-3 is a cell line derived from prostate cancer epithelial cells. Ecotin and M84R/M85R ecotin were found to decrease tumor size and metastasis in PC-3 implanted nude mice. Studies to identify additional serine proteases made by cancer cells were done using PC-3 cells. By using PCR techniques and degenerate oligonucleotide primers, five independent serine protease cDNAs were reported isolated from PC-3 mRNA. A serine protease termed "MT-SP1" was cloned, its cDNA characterized and reported to encode a mosaic, transmembrane protease. (Takeuchi et al., *PNAS (US)*, 96:11054–11061 (1999).)

It was subsequently reported that the reported matriptase sequence was included in the translated sequence for the cDNA of MT-SP1. The matriptase cDNA was reported to be a partial MT-SP1 cDNA and to lack 516 of the coding nucleotides (Takeuchi et al., *J. Biol. Chem*, 275:26333–26342 (2000).) Since the reported matriptase cDNA sequence encoded a possible initiating methionine, it was proposed that alternative splicing could yield a protein lacking the N-terminal region of MT-SP1.

Both matriptase and MT-SP1 are reported to demonstrate trypsin-like protease activity. MT-SP1 has been reported to be a Type II transmembrane protein with an extracellular protease domain. Studies on matriptase have reported that a portion of enzyme molecules were localized on the surfaces of cells.

Additional studies have investigated the substrate specificity of MT-SP1. These experiments have reported that protease-activated receptor 2 (PAR2) and single-chain urokinase-type plasminogen activator (sc-uPA) are macromolecular substrates of MT-SP1. PAR2 is reported to function in inflammation, cytoprotection and/or cell adhesion, while sc-uPa is reported to function in tumor cell invasion and metastasis.

Published PCT application WO 01/57194, "Nucleic Acid Molecules Encoding Transmembrane Serine Proteases, the Encoded Proteins and Methods Based Thereon", is said to describe polypeptides which comprise protease domains of certain membrane-type serine proteases ("MTSP"), including MTSP1.

Published PCT application WO 99/42120 "TADG-15: An Extracellular Serine Protease Over expressed in Breast and Ovarian Carcenomas" and U.S. Pat. No. 5,972,616 are said to describe DNA sequences encoding the TADG-15 protein and an isolated TADG-15 protein coded by such DNA sequences.

Published PCT application WO 01/29056 "TADG-15: An Extracellular Serine Protease Over expressed in Carcinomas" is said to describe DNA sequences encoding TADG-15 proteins.

Certain bis-benzamidine compounds which are said to be inhibitors of matriptase were reported by Enyedy et al., *J. Med. Chem.*, 44:1349–1355 (2001).

Published PCT application WO 01/97794 "Structure Based Discovery of Inhibitors of Matriptase for the Treatment of Cancer and Other Conditions", is said to describe methods of inhibiting carcinoma progression wherein matriptase plays a role and compounds useful in those methods.

Published PCT Application WO 02/08392 "Regulation of Human Matriptase-Like Serine Protease" is said to describe, inter alia, certain matriptase-like serine proteases, methods for their detection, and methods of screening for agents which modulate the activity of a human matriptase-like serine protease.

SUMMARY OF THE INVENTION

The present invention relates to compounds that bind to the serine protease domain of matriptase or MTSP1 and that are selective inhibitors of the serine protease activity of matriptase or MTSP1 and to their use in inhibiting the serine protease activity of matriptase or MTSP1. Inhibition of serine protease activity of matriptase or MTSP1 is useful in the prevention and treatment of cancerous conditions, including having activity in retarding tumor progression and metastasis.

Matriptase and MTSP1 both have been reported to be trypsin-like serine proteases involved in the degradation of the extracellular matrix (ECM). Cloning studies indicate that matriptase and MTSP1 share a common serine protease domain. Degradation of the extracellular matrix (basement membrane and interstitial stroma) is an important aspect of metastasis and is required for metastatic cancer cells to migrate through anatomical barriers and to invade tissues. Thus, breakdown of the extracellular matrix is a primary factor in progression of cancerous conditions. In one aspect, the present invention relates to compounds and their use for the selective inhibition of serine protease activity of matriptase or MTSP1 in order to decrease the cancer-related breakdown of the extracellular matrix.

As such, in one embodiment, the present invention provides a compound Formula I:

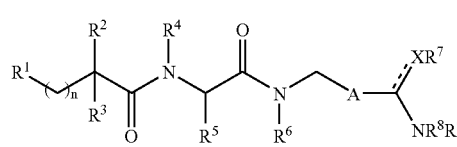

wherein:

$R^1$ is selected from an optionally substituted $C_1$–$C_8$ alkyl, an optionally substituted $C_1$–$C_8$ alkoxy, an optionally substituted $C_1$–$C_8$ alkoxycarbonylamino, an optionally substituted carboxy, an optionally substituted carboxyalkyl, an optionally substituted carboxyalkenyl, an optionally substituted $C_1$–$C_8$ alkanoyl, an optionally substituted carbamoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylalkyl, an optionally substituted $C_1$–$C_8$ alkylthio, an optionally substituted $C_1$–$C_8$ alkylsulfinyl, an optionally substituted $C_1$–$C_8$ alkylsulfonyl, an optionally substituted $C_1$–$C_8$ alkylsulfonylcarbamoyl, an optionally substituted aryl, an optionally substituted arylsulfinyl, an optionally substituted arylsulfonyl, an optionally substituted arylsulfonylcarbamoyl, an optionally substituted aralkylsulfonyl, an optionally substituted amino, and an acid isostere.

n is a value of 0 to about 6.

$R^2$ is selected from an optionally substituted aryl, an optionally substituted $C_1$–$C_8$ alkylcarbamoyl, an optionally substituted $C_1$–$C_8$ alkoxycarbonylamino, an optionally substituted $C_1$–$C_8$ alkoxycarbonyl, an optionally substituted $C_1$–$C_8$ alkoxycarbonylalkyl, an optionally substituted amino, an optionally substituted carbamoyl, an optionally substituted carboxyalkyl, an optionally substituted heteroaryl, an optionally substituted aralkyl, an optionally substituted heteroaralkyl, an optionally substituted heteroararyl, an optionally substituted cycloalkyl, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted heteroarylalkylsulfamoyl, an optionally substituted alkylsulfamoyl, an optionally substituted arylsulfamoyl, an optionally substituted heteroarylsulfamoyl, an optionally substituted aralkylsulfonylcarbamoyl and hydroxy; or in an alternative embodiment, $R^1$, $R^2$ and the atoms to which they are attached, join to form an optionally substituted 5- or 6-membered heterocyclic or carbocylic ring.

$R^3$ is selected from an optionally substituted aryl, an optionally substituted $C_1$–$C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group; or in alternative embodiments, $R^1$ and $R^3$, or $R^2$ and $R^3$, together with the atoms to which they are attached, join to form an optionally substituted 5- or 6-membered carbocylic ring, or heterocylic ring.

$R^4$ is selected from hydrogen, an optionally substituted $C_1$–$C_8$ alkyl, and an optionally substituted aryl; or in alternative embodiments, $R^3$, $R^4$ or, $R^2$, $R^4$ and the atoms to which they are attached, join to form an optionally substituted 5- or 6-membered heterocyclic or carbocylic ring.

$R^5$ is selected from hydrogen, an optionally substituted $C_1$–$C_8$ alkyl, and an optionally substituted aryl, an optionally substituted aralkyl, or, alternatively, $R^4$, $R^5$ and the atoms to which they are attached, join to form a 5- or 6-membered heterocyclic or heteroaryl ring.

$R^6$ is selected from hydrogen, an optionally substituted $C_1$–$C_8$ alkyl, and an optionally substituted aryl; or in an alternative embodiment, $R^5$, $R^6$ and the atoms to which they are attached, join to form an optionally substituted 5- or 6-membered heterocyclic or carbocylic ring.

'A' is selected from an optionally substituted $C_1$–$C_8$ alkylene, a five- or a six-membered optionally substituted cycloalkyl group, a 5 to 10-membered optionally substituted aryl group and a 5 to 10-membered optionally substituted heteroaryl group, wherein said 5 to 10-membered optionally substituted heteroaryl group has from 1 to 3 heteroatoms selected from optionally substituted N, O, and S, wherein 'A' can optionally have a heteroatom for attachment.

X is a heteroatom selected from S, O and N.

$R^7$, if present, is a member selected from hydrogen, hydroxy, an optionally substituted $C_1$–$C_8$ alkyl, an optionally substituted $C_1$–$C_8$ alkoxy, an optionally substituted aryl, an optionally substituted $C_1$–$C_8$ alkanoyl, an optionally substituted $C_1$–$C_8$ alkanoyloxy, an optionally substituted alkylcarbamoyl, an optionally substituted alkoxycarbonyl, an optionally substituted $C_1$–$C_8$ alkoxycarbonyloxy; alternatively, A, $R^7$, and the atoms to which they are attached, join to form a 5- to 10-membered optionally substituted heteroaryl group, wherein said 5- to 10-membered optionally substituted heteroaryl group has at least 1 optionally substituted nitrogen and the dotted line is either a bond or is absent.

$R^8$ and $R^9$ are members independently selected from hydrogen, hydroxy, an optionally substituted $C_1$–$C_8$ alkyl, an optionally substituted alkoxy, an optionally substituted aryl, an optionally substituted $C_1$–$C_8$ alkanoyl, an optionally substituted alkanoyloxy, an optionally substituted $C_1$–$C_8$ alkylcarbamoyl, an optionally substituted alkoxycarbonyl, and an optionally substituted $C_1$–$C_8$ alkoxycarbonyloxy, in an alternative embodiment, $R^7$ and $R^9$ and the atoms to which they are attached, join to form a 5- to 7-membered heterocyclic or heteroaryl ring.

Also, according to an aspect of the present invention, provided are pharmaceutical compositions which comprise an amount effective to inhibit or decrease serine protease activity of matriptase or MTSP1 of a compound of Formula I.

According to an alternate aspect of the present invention, provided are methods of creating a pathologic condition in a mammal which is ameliorated by decreasing or inhibiting serine protease activity of matriptase or MTSP1 which comprises administering to the mammal an amount of a compound of Formula I effective to decrease or inhibit serine protease activity of matriptase or MTSP1. Also provided are methods of treating a pathologic condition in mammal which is ameliorated by decreasing or inhibiting serine protease activity of matriptase or MTSP1 which comprises administering to said mammal a pharmaceutical composition comprising a compound of formula effective to decrease or inhibit serine protease activity of matriptase or MTSP1.

The present invention is also directed to administration of a selective inhibitor of serine protease activity of matriptase or MTSP1 to an area of a mammal suspected of having metastatic cancer cells in order to retard tumor progression. Also, provided are pharmaceutical compositions which comprise a selective inhibitor of serine protease activity matriptase or MTSP1 and a pharmaceutically acceptable carrier. In addition, the compounds of the present invention are suitable to treat other conditions such as unstable angina, refractory angina, myocardial infarction, deep venous thrombosis, pulmonary embolism, myocardial infarction, stroke, thromboembolic complications of surgery and peripheral arterial occlusion.

These and other aspects of the present invention will become more apparent when read with the accompanying detailed description and drawings which follow.

DETAILED DESCRIPTION OF THE INVENTION

I. Definitions

Figure 1:
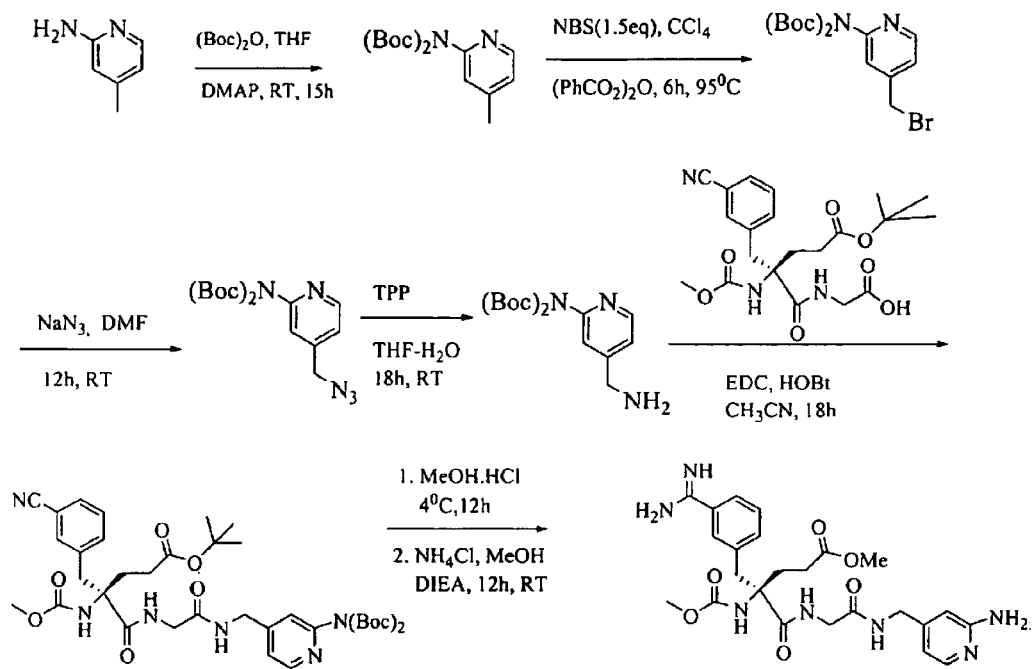
FIG. 1 illustrates a synthetic scheme for certain embodiments of the present invention.

"Matriptase" is a trypsin-like serine protease active in the development of cancerous conditions, such as tumors and metastasis of cancer. Matriptase is a matrix degrading protease that is reported to be localized on the cell surface. Matriptase is reported to have 683 amino acids and contains three main structural regions, a serine protease domain near the carboxyl-terminal region, four tandem low-density lipoprotein receptor domains, and two tandem complement subcomponents C1r and C1s.

Membrane-type serine protease 1 ("MT-SP1" or "MTSP1") refers to a serine protease originally cloned from the PC-3 cell line. MT-SP1 is reported to be a Type II transmembrane protein with an extracellular protease domain. The amino acid sequence reported for matriptase has been reported to be included within the translated sequence for the cDNA of MT-SP1. The cDNA of MT-SP1 is reported to have, in addition to regions coding for the three main structural regions described above for matriptase, an additional 516 nucleotides that make up a signal/anchor domain.

A "cancerous condition" is one in which the patient has a progressive human cancer, such as, leukemia, lymphomas, human melanomas, breast, gastrointestinal, such as esophageal, stomach, colon, bowel, colorectal and rectal cancers, prostate, bladder, testicular, ovarian, uterine, cervical, brain, lung, bronchial, larynx, pharynx, pancreatic, thyroid, bone, and various types of skin cancers.

"Metastasis" is the spread of cancer from an original location to a new location in the body.

In accordance with the present invention and as used herein, the following terms are defined to have following meanings, unless explicitly stated otherwise:

"Acid isostere" means a group which has chemical and physical similarities producing broadly similar biological properties to a carboxylic group (see, Lipinski, Annual Reports in Medicinal Chemistry, 1986 21, p283 "Bioisosterism In Drug Design"; Yun, Hwahak Sekye, 1993,33, p576–579 "Application Of Bioisosterism To New Drug Design"; Zhao, Huaxue Tongbao, 1995, p34–38 "Bioisosteric Replacement And Development Of Lead Compounds In Drug Design"; Graham, Theochem, 1995 343 p105–109 "Theoretical Studies Applied To Drug Design: ab initio Electronic Distributions In Bioisosteres"). Examples of suitable acid bioisosteres include: —C(=O)—NH—OH, C(=O)—CH$_2$OH, —C(=O)—CH$_2$SH, —C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl. Those of skill in the art will know of other acid isosteres suitable for use in the present invention.

"Alkanoyl" means an alkyl-C(O) group wherein the alkyl group is as defined herein. Representative alkanoyl groups include methoyl, ethoyl, and the like.

"Alkanoyloxy" means an alkyl-C(O)O group wherein the alkyl group is as defined herein. Representative alkanoyloxy groups include methoyloxy, ethoyloxy, and the like.

"Alkoxy" means an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" means an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxyalkoxy" means an alkyl-O-alkylenyl-O— group. Representative alkoxyalkoxy include methoxymethoxy, methoxyethoxy, ethoxyethoxy, and the like.

"Alkoxycarbonyl" means an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkylcarbamoyl" means an alkyl-NH—CO— group wherein alkyl group is defined herein. Preferred alkylcarbamoyl groups are those wherein the alkyl group is lower alkyl.

"Alkoxycarbonyloxy" means a carbonate group; i.e., an alkyl-O—C(O)O— group wherein alkyl is as defined herein. Representative alkoxycarbonyloxy groups include methoxycarbonyloxy, ethoxycarbonyloxy, t-butyloxycarbonyloxy, and the like.

"Alkoxycarbonylalkyl" means an alkyl-O—CO-alkylene-group wherein alkyl and alkylene are as defined herein. Representative alkoxycarbonylalkyl include methoxycarbonylmethyl, and ethoxycarbonylmethyl, methoxycarbonyl ethyl, and the like.

"Alkoxycarbonylamino" means a carbamate functionality i.e., alkyl-O—C(O)—NH— group wherein the alkyl group is as defined herein. Preferred alkoxycarbonylamino groups include those wherein the alkyl group is a lower alkyl.

"Alkyl" means an aliphatic hydrocarbon group, which may be straight or branched-chain, having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means 1 to about 4 carbon atoms in the chain, which may be straight or branched. The alkyl is optionally substituted with one or more "alkyl group substituents" which may be the same or different, and include halo, cycloalkyl, hydroxy, alkoxy, amino, carbamoyl, acylamino, aroylamino, carboxy, alkoxycarbonyl, aralkyloxycarbonyl, or heteroaralkyloxycarbonyl. Representative alkyl groups include methyl, trifluoromethyl, cyclopropylmethyl, cyclopentylmethyl, ethyl, n-propyl, i-propyl, n-butyl, 1-butyl, n-pentyl, 3-pentyl, methoxyethyl, carboxymethyl, methoxycarbonylethyl, benzyloxycarbonylmethyl, and pyridylmethyloxycarbonylmethyl.

"Alkylene" means a straight or branched bivalent hydrocarbon chain of 1 to about 6 carbon atoms. The alkylene is optionally substituted with one or more "alkylene group substituents" which may be the same or different, and include halo, cycloalkyl, hydroxy, alkoxy, carbamoyl, carboxy, cyano, aryl, heteroaryl or oxo. The alkylene is optionally interrupted by a heteroatom, i.e., a carbon thereof is substituted by, —O—, —S(=O)$_m$ (where m is 0–2), or —NR'-(where R' is lower alkyl). Preferred alkylene groups are the lower alkylene groups having 1 to about 4 carbon atoms. Representative alkylene groups include methylene, ethylene, and the like.

"Alkenylene" means a straight or branched bivalent hydrocarbon chain containing at least one carbon—carbon double bond. The alkenylene is optionally substituted with one or more "alkylene group substituents" as defined herein. The alkenylene is optionally interrupted by a heteroatom, i.e., a carbon thereof is substituted by, —O—, —S(O)$_m$ (where m is 0–2), or —NR'-(where R' is lower alkyl). Representative alkenylene include —CH=CH—, —CH$_2$CH=CH—, —C(CH$_3$)=CH—, —CH$_2$CH=CHCH$_2$—, and the like.

"Alkylsulfinyl" means an alkyl-SO— group wherein the alkyl group is as defined above. Preferred alkylsulfinyl groups are those wherein the alkyl group is lower alkyl.

"Alkylsulfonyl" means an alkyl-SO$_2$— group wherein the alkyl group is as defined herein. Preferred alkylsulfonyl groups are those wherein the alkyl group is lower alkyl.

"Alkylsulfonylcarbamoyl" means an alkyl-SO$_2$—NH—CO— group wherein alkyl group is defined herein. Preferred alkylsulfonylcarbamoyl groups are those wherein the alkyl group is lower alkyl.

"Alkylthio" means an alkyl-S— group wherein the alkyl group is as defined herein. Preferred alkylthio groups are those wherein the alkyl group is lower alkyl. Representative alkylthio groups include methylthio, ethylthio, i-propylthio, heptylthio, and the like.

"Alkynyl" means a straight or branched aliphatic hydrocarbon group of 2 to about 15 carbon atoms which contains at least one carbon-carbon triple bond. Preferred alkynyl groups have 2 to about 12 carbon atoms. More preferred alkynyl groups contain 2 to about 4 carbon atoms. "Lower alkynyl" means alkynyl of 2 to about 4 carbon atoms. The alkynyl group may be substituted by one or more alkyl group substituents as defined herein. Representative alkynyl groups include ethynyl, propynyl, n-butynyl, 2-butynyl, 3-methylbutynyl, n-pentynyl, heptynyl, octynyl, decynyl, and the like.

"Alkynyloxy" means an alkynyl-O— group wherein the alkynyl group is as defined herein. Representative alkynyloxy groups include propynyloxy, 3-butynyloxy, and the like.

"Alkynyloxyalkyl" means alkynyl-O-alkylene- group wherein alkynyl and alkylene are as defined herein.

"Amino" means a group of formula Y$_1$Y$_2$N— wherein Y$_1$ and Y$_2$ are independently hydrogen; acyl; or alkyl, or Y$_1$ and Y$_2$ taken together with the N through which Y$_1$ and Y$_2$ are linked form a 4 to 7 membered azaheterocyclyl. Representative amino groups include amino (H$_2$N—), methylamino, dimethylamino, diethylamino, and the like.

"Aminoalkyl" means an amino-alkylene- group wherein amino and alkylene are defined herein. Representative aminoalkyl groups include aminomethyl, aminoethyl, dimethylaminomethyl, and the like.

"Aralkenyl" means an aryl-alkenylene- group wherein aryl and alkenylene are as defined herein. Preferred aralkenyls contain a lower alkenylene moiety. A representative aralkenyl group is 2-phenethenyl.

"Aralkyloxy" means an aralkyl-O— group wherein aralkyl is defined herein. Representative aralkyloxy groups include benzyloxy, naphth-1-ylmethoxy, naphth-2-ylmethoxy, and the like.

"Aralkyloxyalkyl" means an aralkyl-O-alkylene- group wherein aralkyl and alkylene are as defined herein. A representative aralkyloxyalkyl group is benzyloxyethyl.

"Aralkyloxycarbonyl" means an aralkyl-O—CO— group wherein aralkyl is as defined herein. A representative aralkoxycarbonyl group is benzyloxycarbonyl.

"Aralkyloxycarbonylalkyl" means an aralkoxycarbonylalkylene- group wherein aralkyloxycarbonyl and alkylene are as defined herein. Representative aralkoxycarbonylalkyls include benzyloxycarbonylmethyl, and benzyloxycarbonylethyl.

"Aralkyl" means an aryl-alkylene- group wherein aryl and alkylene are as defined herein. Preferred aralkyls contain a lower alkyl moiety. Representative aralkyl groups include benzyl, 2-phenethyl, naphthlenemethyl, and the like.

"Aralkyloxyalkenyl" means an aralkyl-O-alkenylene- group wherein aralkyl and alkenylene are as defined herein. A representative aralkyloxyalkenyl group is 3-benzyloxyallyl.

"Aralkylsulfonyl" means an aralkyl-SO$_2$— group wherein aralkyl is as defined herein.

"Aralkylsulfinyl" means an aralkyl-SO— group wherein aralkyl is as defined herein.

"Aralkylthio" means an aralkyl-S— group wherein aralkyl is as defined herein. A representative aralkylthio group is benzylthio.

"Aroyl" means an aryl-CO— group wherein aryl is defined herein. Representative aroyl include benzoyl, naphth-1-oyl and naphth-2-oyl.

"Aryl" means an aromatic monocyclic or multicyclic ring system of 6 to about 14 carbon atoms, preferably of 6 to about 10 carbon atoms. The aryl is optionally substituted with one or more "ring system substituents" which may be the same or different, and are as defined herein. Representative aryl groups include phenyl and naphthyl. Representative ring system substituents include, but are not limited to, alkyl, hydroxy, amino, amidino, cyano and arylsulfamoyl.

"Aralkynyl" means an aryl-alkynylene- group wherein aryl and alkynylene are defined herein. Representative aralkynyl groups include phenylacetylenyl and 3-phenylbut-2-ynyl.

"Arylcarbamoyl" means an aryl-NHCO— group, wherein aryl is defined herein.

"Arylsulfinyl" means an aryl-SO— group wherein the aryl group is as defined herein. Preferred arylsulfinyl groups are those wherein the aryl group is a substituted phenyl.

"Arysulfonyl" means an aryl-SO$_2$— group wherein the aryl group is as defined herein. Preferred arylsulfonyl groups are those wherein the aryl group is a substituted phenyl.

"Arylsulfonylcarbamoyl" means an aryl-SO$_2$—NH—CO— group wherein aryl group is defined herein. Preferred arylsulfonylcarbamoyl groups are those wherein the aryl group is a substituted phenyl.

"Benzyl" means a phenyl-CH$_2$— group. Substituted benzyl means a benzyl group in which the phenyl ring is substituted with one or more ring system substituents. Representative benzyl include 4-bromobenzyl, 4-methoxybenzyl, 2,4-dimethoxybenzyl, and the like.

"Carbamoyl" means a group of formula Y$_1$Y$_2$ NCO— wherein Y$_1$ and Y$_2$ are independently hydrogen; acyl; or alkyl, or Y$_1$ and Y$_2$ taken together with the N through which Y$_1$ and Y$_2$ are linked form a 4 to 7 membered azaheterocyclyl. Representative carbamoyl groups include carbamoyl (H$_2$NCO—), dimethylaminocarbamoyl (Me$_2$NCO—), and the like.

"Carboxy" and "carboxyl" mean a HO(O)C— group (i.e. a carboxylic acid).

"Carboxyalkyl" means a HO(O)C-alkylene- group wherein alkylene is defined herein. Representative carboxyalkyls include carboxymethyl and carboxyethyl.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamantyl, and the like. The prefix spiro before cycloalkyl means that geminal substituents on a carbon atom are replaced to form 1,1-cycloalkyl. "Cycloalkylene" means a bivalent cycloalkyl having about 4 to about 8 carbon atoms. Preferred cycloalkylenyl groups include 1,2-, 1,3-, or 1,4-cis or trans-cyclohexylene.

"Cycloalkenyl" means a non-aromatic mono- or multicyclic ring system of about 3 to about 10 carbon atoms, preferably of about 5 to about 10 carbon atoms which contains at least one carbon—carbon double bond. Preferred cycloalkylene rings contain about 5 to about 6 ring atoms.

The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl.

"Cycloalkyloxy" means a cycloalkyl-O— group wherein cycloalkyl is as defined herein. Representative cycloalkyloxy groups include cyclopentyloxy, cyclohexyloxy, and the like.

"Halo" or "halogen" mean fluoro, chloro, bromo, or iodo.

"Heteroaralkenyl" means a heteroaryl-alkenylene- group wherein heteroaryl and alkenylene are as defined herein. Preferred heteroaralkenyls contain a lower alkenylene moiety. Representative heteroaralkenyl groups include 4-pyridylvinyl, thienylethenyl, pyridylethenyl, imidazolylethenyl, pyrazinylethenyl, and the like.

"Heteroaralkyl" means a heteroaryl-alkylene- group wherein heteroaryl and alkylene are as defined herein. Preferred heteroaralkyls contain a lower alkylene group. Representative heteroaralkyl groups include thienylmethyl, pyridylmethyl, imidazolylmethyl, pyrazinylmethyl, and the like.

"Heteroararyl" means a heteroaryl-aryl- group wherein heteroaryl and aryl are as defined herein. Representative heteroararyl groups include thienylphenyl, pyridylphenyl, imidazolylphenyl, pyrazinylphenyl, and the like.

"Heteroaralkyloxy" means an heteroaralkyl-O— group wherein heteroaralkyl is as defined herein. A representative heteroaralkyloxy group is 4-pyridylmethyloxy.

"Heteroaralkyloxyalkenyl" means a heteroaralkyl-O-alkenylene- group wherein heteroaralkyl and alkenylene are as defined herein. A representative heteroaralkyloxyalkenyl group is 4-pyridylmethyloxyallyl.

"Heteroaralkyloxyalkyl" means a heteroaralkyl-O-alkylene- group wherein heteroaralkyl and alkylene are as defined herein. A representative heteroaralkyloxy group is 4-pyridylmethyloxyethyl.

"Heteroaralkynyl" means an heteroaryl-alkynylene- group wherein heteroaryl and alkynylene are as defined herein. Preferred heteroaralkynyls contain a lower alkynylene moiety. Representative heteroaralkynyl groups include pyrid-3-ylacetylenyl, quinolin-3-ylacetylenyl, 4-pyridylethynyl, and the like.

"Heteroaroyl" means an means a heteroaryl-CO— group wherein heteroaryl is as defined herein. Representative heteroaroyl groups include thiophenoyl, nicotinoyl, pyrrol-2-ylcarbonyl, pyridinoyl, and the like.

"Heteroaryidiazo" means an heteroaryl-N═N— group wherein heteroaryl is as defined herein.

"Heteroarylsulphonylcarbamoyl" means a heteroaryl-$SO_2$—NH—CO— group wherein heteroaryl is as defined herein.

"Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to about 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein. The nitrogen or sulphur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to about 6 ring atoms. The "heteroaryl" is optionally substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heterocyclylalkyl" means a heterocyclyl-alkylene- group wherein heterocyclyl and alkylene are as defined herein. Preferred heterocyclylalkyls contain a lower alkylene moiety. A representative heteroaralkyl group is tetrahydropyranylmethyl.

"Heterocyclylalkyloxyalkyl" means a heterocyclylalkyl-O— alkylene group wherein heterocyclylalkyl and alkylene are as defined herein. A representative heterocyclylalkyloxyalkyl group is tetrahydropyranylmethyloxymethyl.

"Heterocyclyloxy" means a heterocyclyl-O— group wherein heterocyclyl is as defined herein. Representative heterocyclyloxy groups include quinuclidyloxy, pentamethylenesulfideoxy, tetrahydropyranyloxy, tetrahydrothiophenyloxy, pyrrolidinyloxy, tetrahydrofuranyloxy, 7-oxabicyclo[2.2.1]heptanyloxy, hydroxytetrahydropyranyloxy, hydroxy-7-oxabicyclo[2.2.1]heptanyloxy, and the like.

"Hydroxyalkyl" means an alkyl group as defined herein substituted with one or more hydroxy groups. Preferred hydroxyalkyls contain lower alkyl. Representative hydroxyalkyl groups include hydroxymethyl and 2-hydroxyethyl.

"Oxo" means a group of formula >C═O (i.e., a carbonyl group).

"Phenoxy" means a phenyl-O— group wherein the phenyl ring is optionally substituted with one or more ring system substituents as defined herein.

"Ring system substituents" mean substituents attached to aromatic or non-aromatic ring systems inclusive of hydrogen, alkyl, aryl, heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, nitrile, $NO_2$ heteroarylthio, aralkylthio, heteroaralkylthio, cycloalkyl, cycloalkenyl, heterocyclyl, heterocyclenyl, aryidiazo, heteroaryldiazo, amidino, and the like.

"Sulfamoyl" means a group of formula $Y_1Y_2NSO_2$— wherein $Y_1$ and $Y_2$ are independently hydrogen; acyl; or alkyl, or $Y_1$ and $Y_2$ taken together with the N through which $Y_1$ and $Y_2$ are linked form a 4 to 7 membered azaheterocyclyl. Representative amino groups include amino ($H_2N$—), methylamino, dimethylamino, diethylamino, and the like. Representative sulfamoyl groups are sulfamoyl ($H_2NSO_2$—) and dimethylsulfamoyl ($Me_2NSO_2$—).

"Ureido" means a group of formula $Y_1Y_2NC(O)NY_3$—, wherein $Y_1$, $Y_2$, $Y_3$ are each independently hydrogen; acyl;

or alkyl, or $Y_1$ and $Y_3$ taken together are linked form a 4 to 7 membered azaheterocyclyl. Representative ureido groups are urea ($H_2NC(O)NH—$) and dimethylurea ($Me_2NH—$). In certain instances, $Y_1$, $Y_3$ and the atoms to which they are attached join to form a 5- to 7-membered heterocycle.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

The term "amino acid" refers to both natural, unnatural amino acids in their D and L stereo isomers if their structures allow such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, demosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, omithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

"Brine" refers to an aqueous saturated solution of sodium chloride.

In addition, the following abbreviations stand for the following:

"AcN", $CH_3CN$ or "MeCN" refer to acetonitrile.

"AIBN" refers to 2,2'-azobisisobutyronitrile.

"Bn" refers to benzyl.

"Boc" refers to t-butoxycarbonyl.

"$Boc_2O$" refers to Boc anhydride (di-tert-butyl carbonate).

"BOC-ON" refers to 2-(tert-butoxycarbonyloxyamino)-2-phenylacetonitrile.

"$BzlSO_2$" refers to benzylsulfonyl.

"Cbz" or "CBz" refers to benzyloxycarbonyl.

"$CNNH_2$" or "$H_2NCN$" refers to cyanamide.

"$CSCO_3$" refers to cesium carbonate.

"DCA" refers to dichloroacetic acid.

"DCC" refers to N,N'-dicyclohexylcarbodiimide.

"DCM" or "$CH_2Cl_2$" refers to dichloromethane.

"DIEA" refers to diisopropylethylamine.

"DMF" refers to N,N-dimethylformamide.

"DMSO" refers to dimethyl sulfoxide.

"DMAP" refers to 4-N,N-dimethylaminopyridine.

"EDC" refers to 1-ethyl-3-(3-dimethylamino-propyl) carbodiimide hydrochloride salt.

"$Et_3N$" or "TEA" refers to triethylamine.

"EtOAc" refers to ethyl acetate.

"EtOH" refers to ethanol.

HATU" refers to 0-(7-azabenzotriazol-1-yl)-1,1,3,3-tetramethyluromium hexafluorophosphate.

"HBTU" refers to 2-(1H-benzotriazol-1-yl)-1,1,3,3-tetramethyluronium hexafluorophosphate.

"HCl" refers to hydrochloric acid.

"HOAc" refers to acetic acid.

"HOAt" or "HOAT" refers to 1-hydroxy-7-azabenzotriazole.

"HOBt" refers to 1-hydroxybenzotriazole monohydrate.

"i-BuOCOCl" refers to isobutylchloroformate.

"HPLC" refers to high pressure liquid chromatography.

"KHMDS" refers to potassium hexamethyldisilazide, also termed potassium bis(trimethylsilyl)amide.

"$LiAlH_4$" refers to lithium aluminum hydride.

"$LiAlH_2(OEt)_2$" refers to lithium aluminum hydride diethoxide.

"Me" refers to methyl.

"MeOH" refers to methanol.

"NMM" refers to N-methylmorpholine.

"NBS" refers to N-bromosuccinimide.

"$PhB(OH)_2$" refers to phenylboronic acid.

"$Ph_3P$" or "$PPh_3$" refers to triphenylphospine.

"PyBOP" refers to benzotriazole-ly-oxy-tris-pyrrolidino-phosphonium hexafluorophosphate.

"RP-HPLC" refers to reverse phase high pressure liquid chromatography.

"Swern Ox" refers to a reaction step called a "Swern oxidation".

"TFA" refers to trifluoroacetic acid.

"THF" refers to tetrahydrofuran.

"TLC" refers to thin layer chromatography.

As will be apparent to one of skill in the art, certain compounds of the present invention possess asymmetric carbon atoms (optical centers) or double bonds; the racemates, diastereomers, enantiomers, geometric isomers and individual isomers are all intended to be encompassed within the scope of the present invention.

II. Compounds

In one embodiment, the present invention provides a compound Formula I:

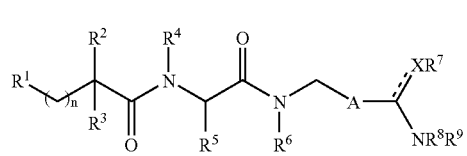

wherein: $R^1$, n, $R^2$, $R^3$, $R^4$, $R^5$, $R^6$, A, X and $R^7$ have previously been defined.

Certain embodiments of Formula I are preferred. For example, compounds of Formula I wherein the portion of the molecule represented by the following formula:

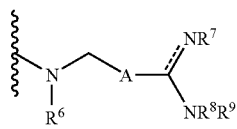

is preferably selected from:

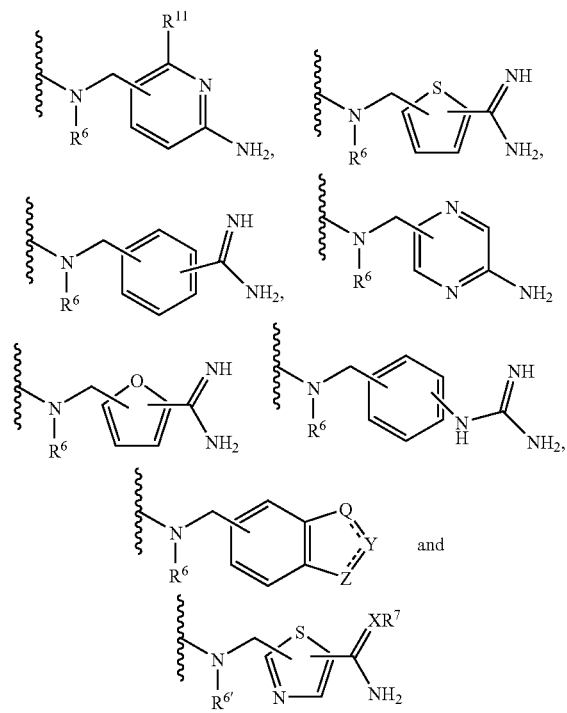

and

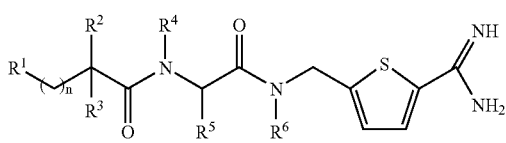

wherein $R^{11}$ is selected from hydrogen, hydroxyl, and an optionally substituted $C_1$–$C_8$ alkyl; and Q, Y and Z are each independently selected from an optional substituted carbon, an optionally substituted nitrogen, an oxygen and a sulfur, provided however at least one of Q, Y and Z is carbon, and wherein the dotted line is an optional double bond.

In certain other aspects, the compounds of Formula I have Formula II:

II

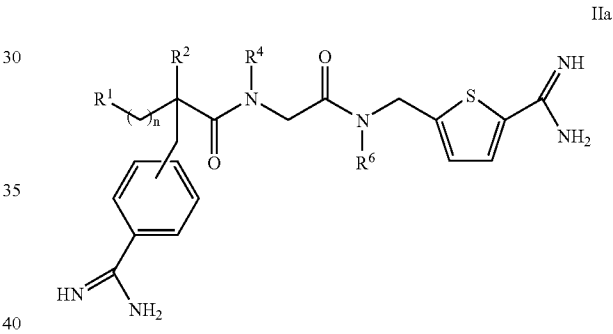

wherein: $R^1$ is selected from an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted amino, an optionally substituted carbamoyl, an optionally substituted $C_1$–$C_8$ alkylsulfonyl, an optionally substituted aryl, optionally substituted arylsulfonyl, and a carboxylic acid isostere; n is a value of about 1 to 4;

$R^2$ is selected from an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted $C_1$–$C_8$ alkoxycarbonylamino, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy;

$R^3$ is selected from an optionally substituted aryl, an optionally substituted aralkyl, an optionally substituted $C_1$–$C_8$ alkoxycarbonyl, an optionally substituted heteroaralkyl, and an optionally substituted carboxy; and $R^5$ is selected from hydrogen, an optionally substituted $C_1$–$C_8$ alkyl, and an optionally substituted aryl.

In a preferred aspect, $R^2$ is selected from an optionally substituted $C_1$–$C_8$ alkylcarbamoyl, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted ureido, an optionally substituted heteroarylalkylsulfamoyl, an optionally substituted alkylsulfamoyl, an optionally substituted arylsulfamoyl, an optionally substituted heteroarylsulfamoyl, and hydroxy.

In still another preferred aspect, $R^2$ is selected from an optionally substituted $C_1$–$C_8$ alkoxycarbonyl.

Further preferred compounds of Formula II, have Formula IIa:

IIa

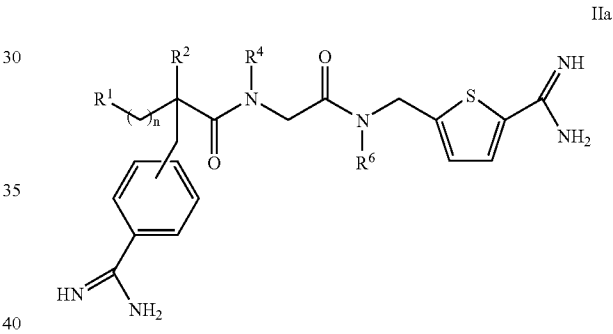

wherein:
$R^1$ is selected from an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted amino, and an optionally substituted carboxy an optionally substituted carbamoyl, an optionally substituted $C_1$–$C_8$ alkylsulfonyl, an optionally substituted aralkylsulfonyl, optionally substituted arylsulfonyl, and an acid isostere;

n is a value of about 1 to 2;

$R^2$ is selected from an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted $C_1$–$C_8$ alkoxycarbonylamino, an optionally substituted carbamoyl, an optionally substituted ureido, an optionally substituted sulfamoyl, an optionally substituted $C_1$–$C_8$ alkylsulfonylcarbamoyl, an optionally substituted heteroarylalkylsulfamoyl, an optionally substituted alkylsulfamoyl, an optionally substituted arylsulfamoyl, an optionally substituted heteroarylsulfamoyl, an optionally substituted arylsulfonylcarbamoyl and hydroxy; and $R^6$ is selected from hydrogen, an optionally substituted $C_1$–$C_8$ alkyl, and an optionally substituted aryl.

In another aspect, the preferred compounds of Formula I have Formula III:

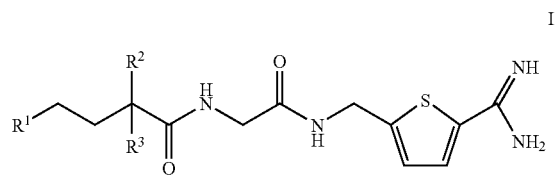

wherein:

$R^1$ is selected from an $C_1$–$C_6$ alkyl, carboxyl group, $C_1$–$C_6$ alkyl-OC(O)NH—, $C_1$–$C_6$ alkylOC(O)—, $C_1$–$C_6$ alkylC(O)—, $C_1$–$C_6$ alkylSO$_2$—, $C_1$–$C_6$ alkylOC(O)NR$^{12}$ wherein $R^{12}$ is a member selected from the group consisting of hydrogen, an optionally substituted $C_1$–$C_8$ alkyl, and an optionally substituted aryl and NR$^{13}$R$^{14}$C(O)—, wherein $R^{13}R^{14}$ are each independently selected from the group of hydrogen, and an optionally substituted $C_1$–$C_8$ alkyl.

In another aspect, the compounds of Formula III have Formula IIIa:

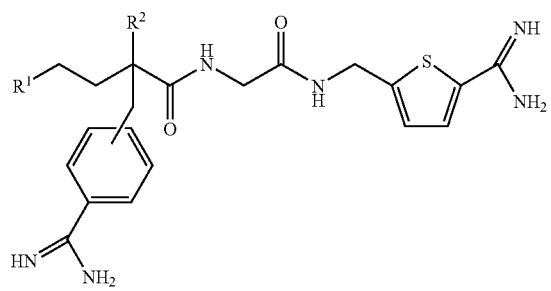

wherein:

$R^2$ is selected from an optionally substituted alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

In another preferred aspect, the compounds of Formula III have Formula IIIb:

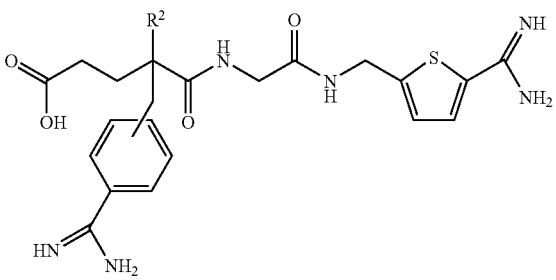

wherein:

$R^2$ is selected from an optionally substituted $C_1$–$C_6$ alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

In certain other aspects, the compounds of Formula III have Formula IIIc:

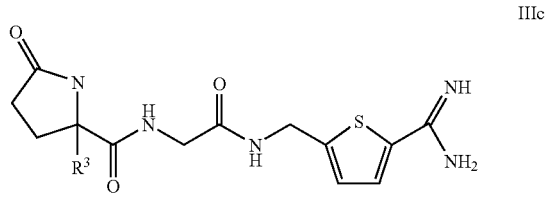

wherein:

$R^3$ is a member selected from the group of an optionally substituted aryl, an optionally substituted $C_1$–$C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group.

In another preferred aspect, the compounds of Formula III have Formula IIId:

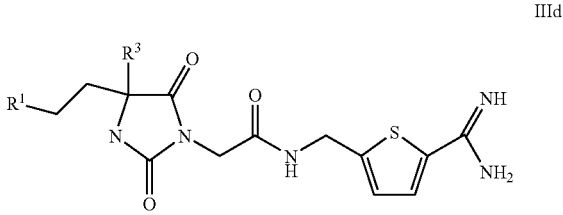

wherein:

$R_1$ is a member selected from the group of an optionally substituted $C_1$–$C_8$ alkyl, an optionally substituted $C_1$–$C_8$ alkoxy, an optionally substituted $C_1$–$C_8$ alkoxycarbonylamino, an optionally substituted carboxy, an optionally substituted carboxyalkyl, an optionally substituted carboxyalkenyl, an optionally substituted $C_1$–$C_8$ alkanoyl, an optionally substituted carbamoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylalkyl, an optionally substituted $C_1$–$C_8$ alkylthio, an optionally substituted $C_1$–$C_8$ alkylsulfinyl, an optionally substituted $C_1$–$C_8$ alkylsulfonyl, an optionally substituted $C_1$–$C_8$ alkylsulfonylcarbamoyl, an optionally substituted aryl, an optionally substituted arylsulfinyl, an optionally substituted arylsulfonyl, an optionally substituted arylsulfonylcarbamoyl, an optionally substituted aralkylsulfonyl, an optionally substituted amino, and an acid isostere;

$R^3$ is a member selected from the group of an optionally substituted aryl, an optionally substituted $C_1$–$C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroaralkenyl, an optionally substituted heteroararyl, and an optionally substituted cycloalkyl group; or $R^2$ and $R^3$, together with the atoms to which they are attached, join to form an optionally substituted 5- or 6-membered heterocyclic or carbocylic ring.

In certain other aspects, the compounds of Formula III have Formula IIIe:

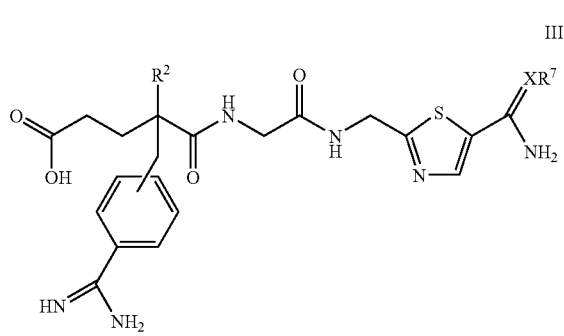

IIIe wherein:

$R^2$ is selected from an optionally substituted $C_1$–$C_6$ alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

In still another aspect, the compounds of Formula I have Formula IV:

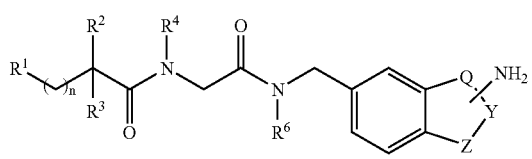

IV wherein:

$R^1$ is selected from an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted carbamoyl, an optionally substituted amino, and an optionally substituted carboxy;

n is a value of about 1 to 2;

$R^2$ is selected from an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy;

$R^3$ is selected from an optionally substituted aryl, an optionally substituted $C_1$–$C_8$ alkoxycarbonyl, and an optionally substituted carboxy; and $R^6$ is selected from hydrogen, an optionally substituted $C_1$–$C_8$ alkyl, and an optionally substituted aryl; and Q, Y and Z are each independently selected from a carbon, an optionally substituted nitrogen, an oxygen and a sulfur, provided however at least one of Q, Y and Z is carbon.

In another aspect, the compounds of Formula IV have Formula IVa:

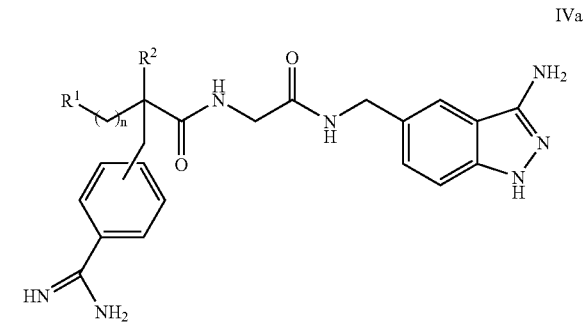

IVa wherein:

$R^1$ is selected from an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted carbamoyl, an optionally substituted amino, and an optionally substituted carboxy;

n is a value of about 1 to 2; and $R^2$ is selected from an optionally substituted aryl, an optionally substituted $C_1$–$C_8$ alkylcarbamoyl, an optionally substituted $C_1$–$C_8$ alkoxycarbonyl, an optionally substituted amino, and an optionally substituted carboxy, an optionally substituted $C_1$–$C_8$ alkoxycarbonylamino, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy.

Certain preferred compounds are set forth below in Table I:

TABLE I
| Compound | Structure |
|---|---|
| 1 | 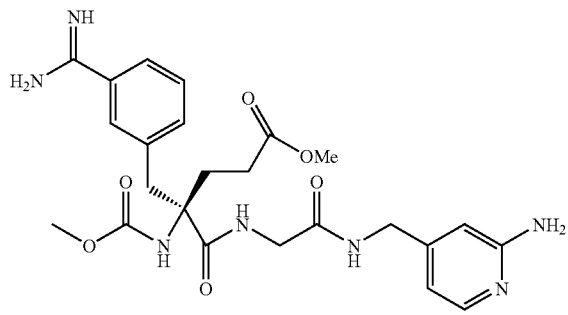 |
| 2 | 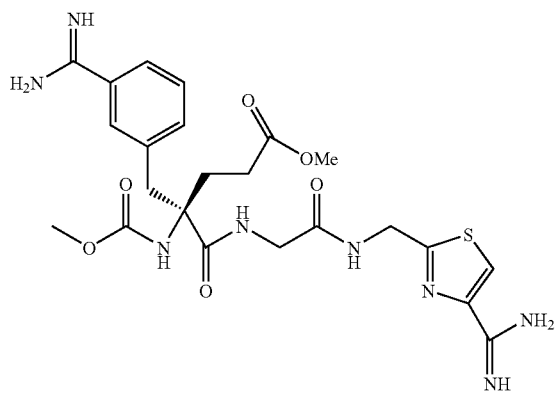 |
| 3 | 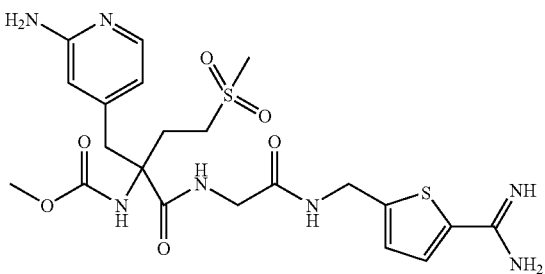 |
| 4 | 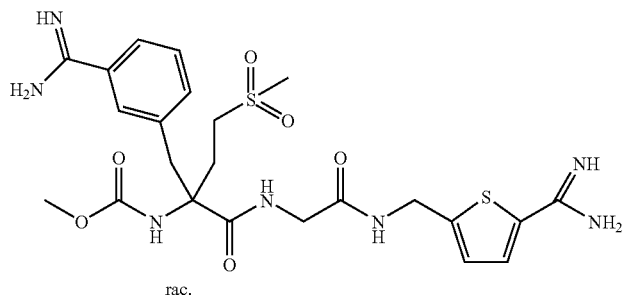 rac. |

TABLE I-continued
| Compound | Structure |
|---|---|
| 5 | 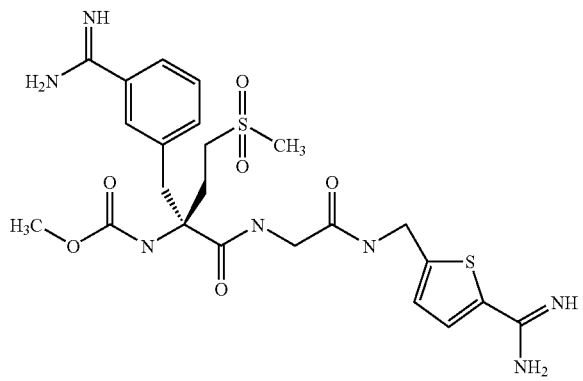 |
| 6 | Chiral 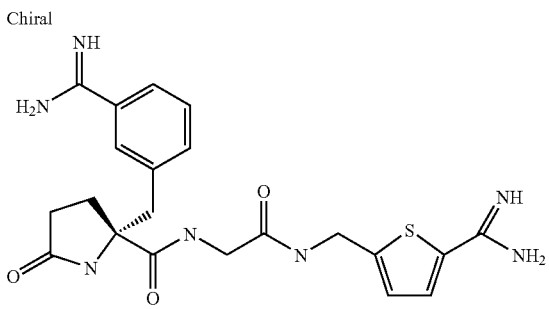 |
| 7 | 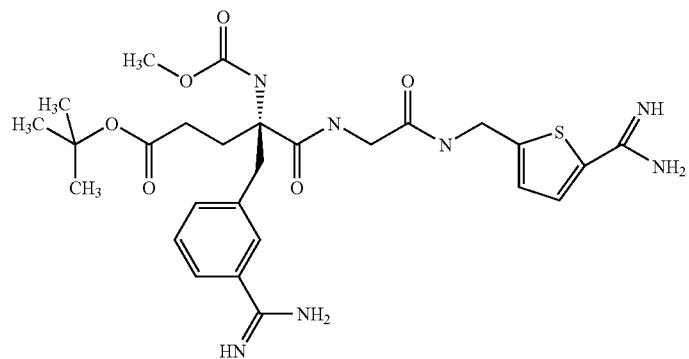 |
| 8 | 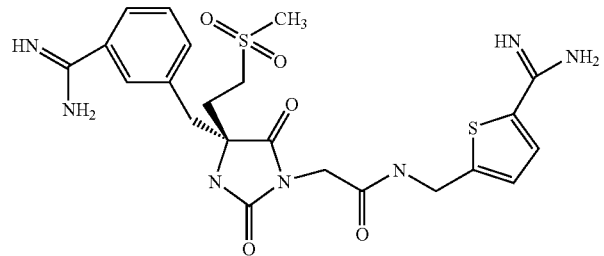 |

TABLE I-continued
| Compound | Structure |
|---|---|
| 9 | 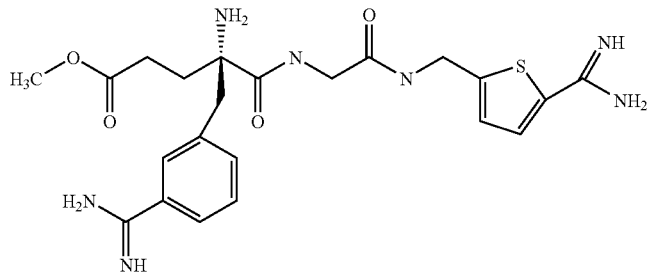 |
| 10 | 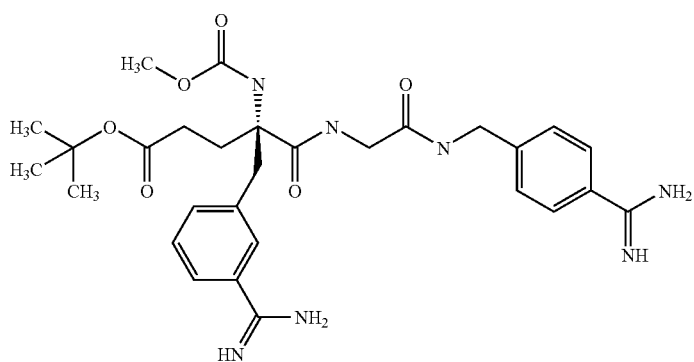 |
| 11 | 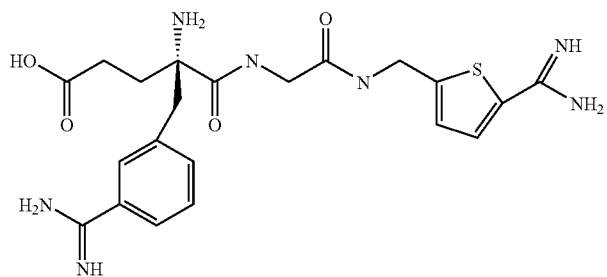 |
| 12 | 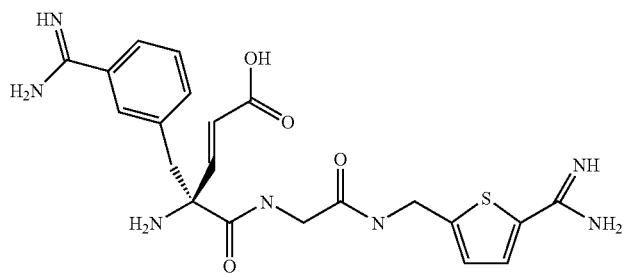 |

TABLE I-continued
| Compound | Structure |
|---|---|
| 13 | 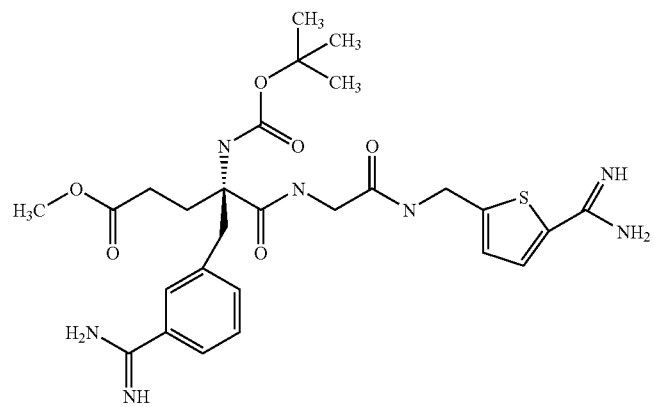 |
| 14 | 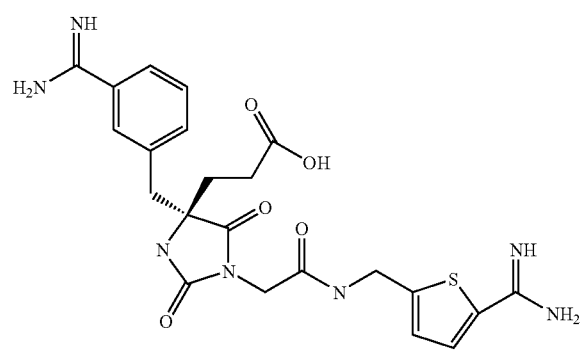 |
| 15 | 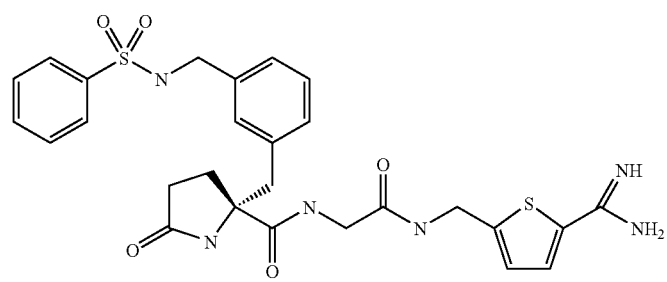 |
| 16 | 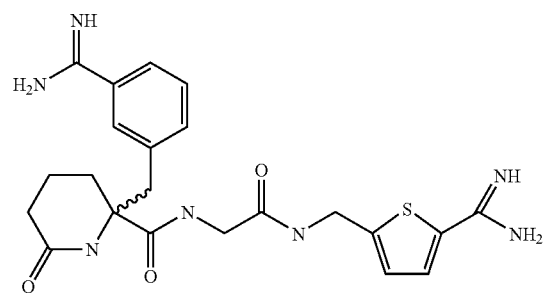 |
| 17 | 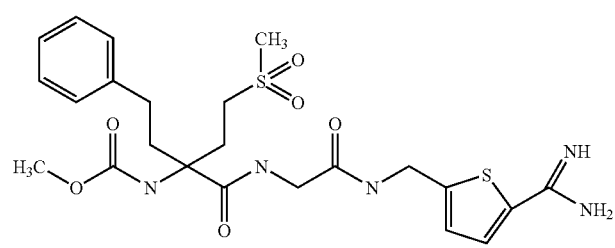 |

TABLE I-continued
| Compound | Structure |
|---|---|
| 18 | 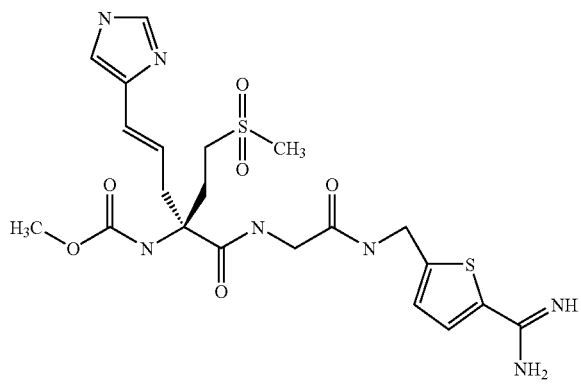 |
| 19 | 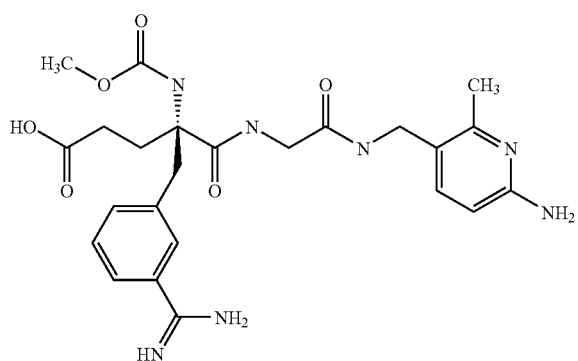 |
| 20 | 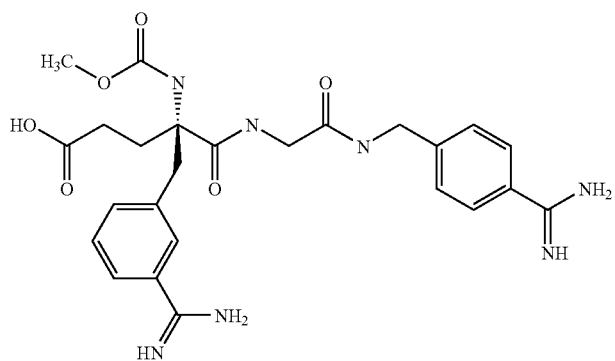 |
| 21 | 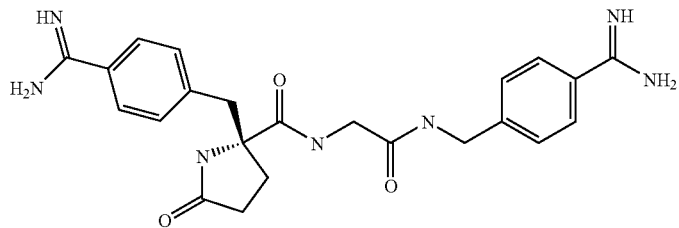 |

TABLE I-continued

| Compound | Structure |
|---|---|
| 22 | 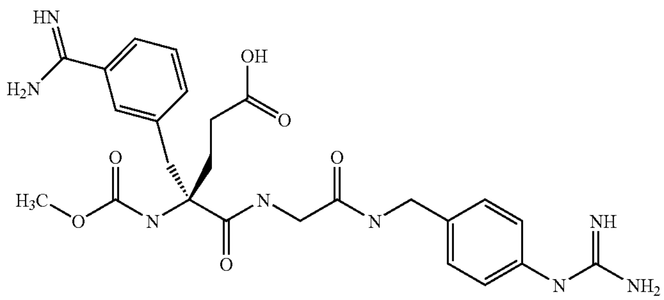 |
| 23 | 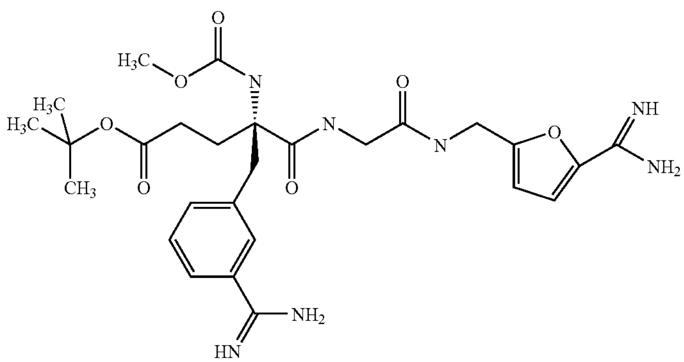 |
| 24 | 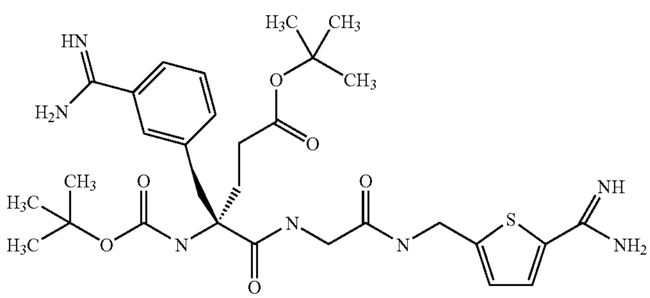 |
| 25 | 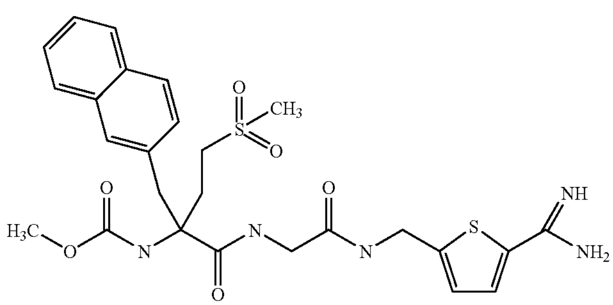 |
| 26 | 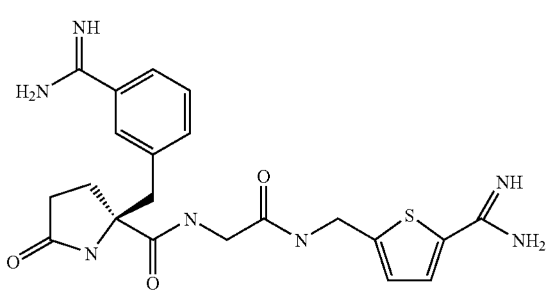 |

TABLE I-continued

| Compound | Structure |
|---|---|
| 27 | 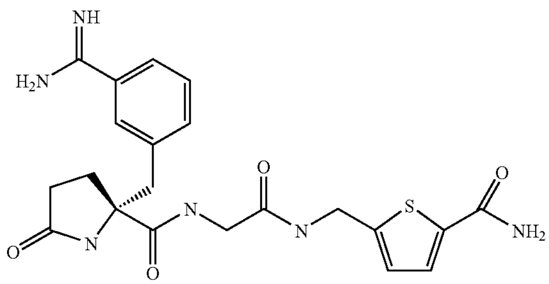 |
| 28 | 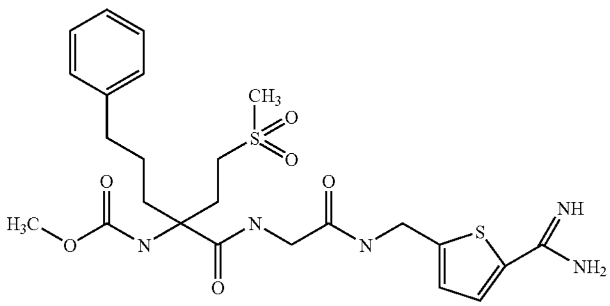 |
| 29 | 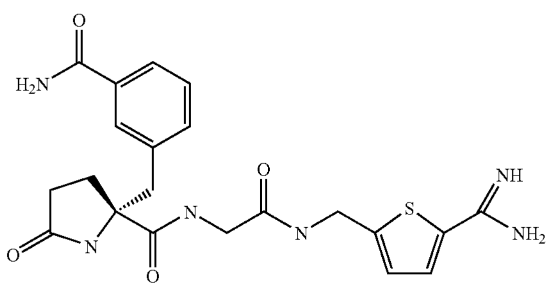 |
| 30 | 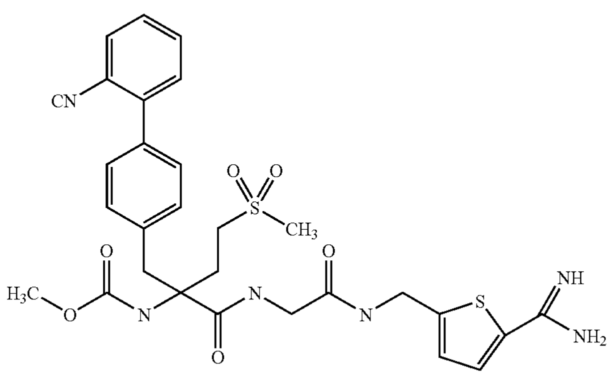 |
| 31 | 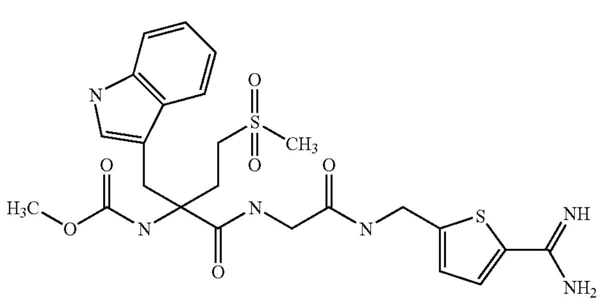 |

TABLE I-continued
| Compound | Structure |
|---|---|
| 32 | 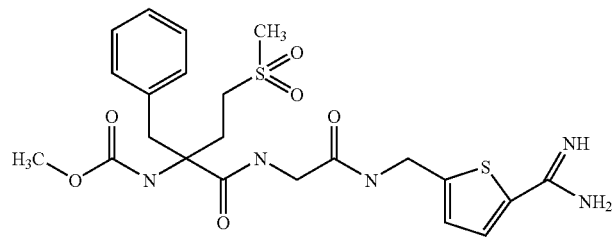 |
| 33 | 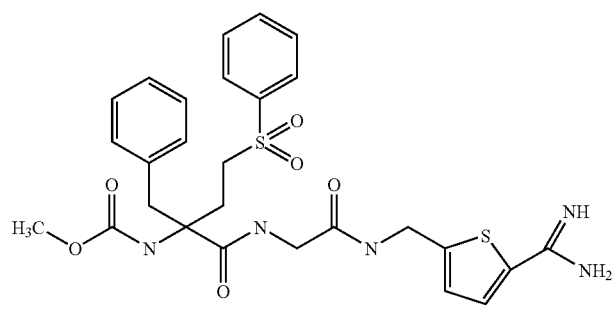 |
| 34 | 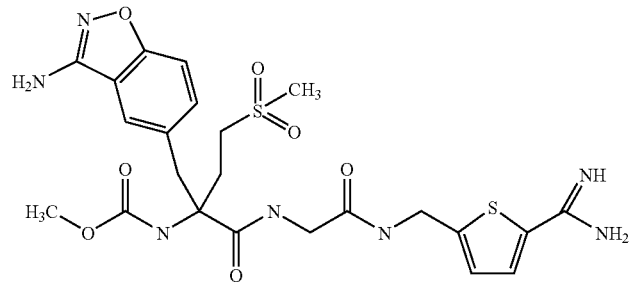 |
| 35 | 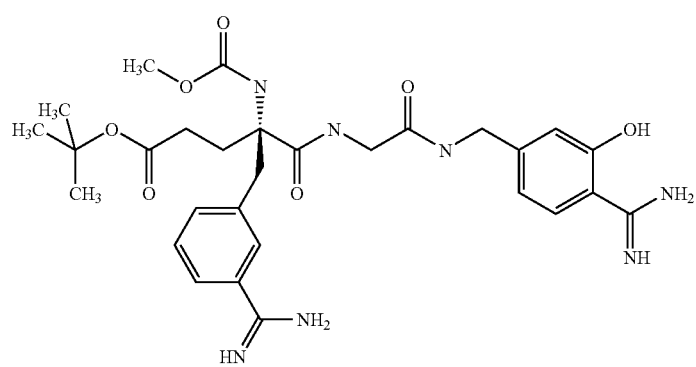 |
| 36 | Chiral 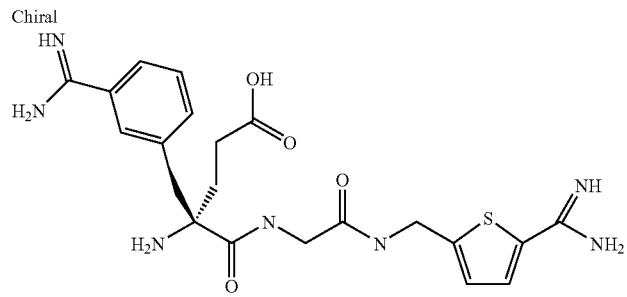 |

TABLE I-continued
| Compound | Structure |
|---|---|
| 37 | 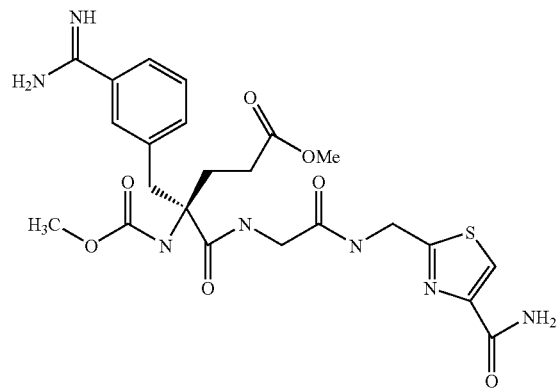 |
| 38 | 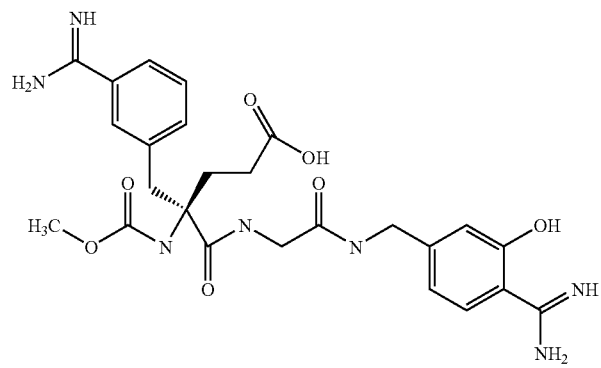 |
| 39 | 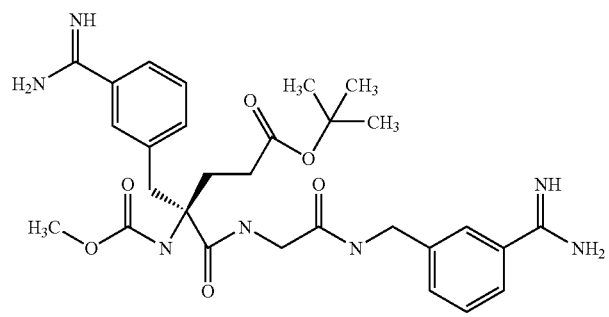 |
| 40 | 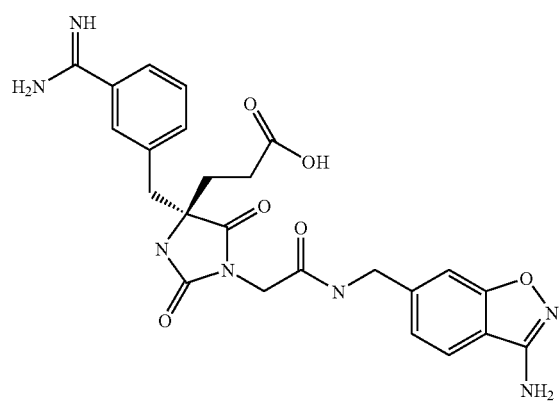 |

TABLE I-continued

| Compound | Structure |
|---|---|
| 41 | 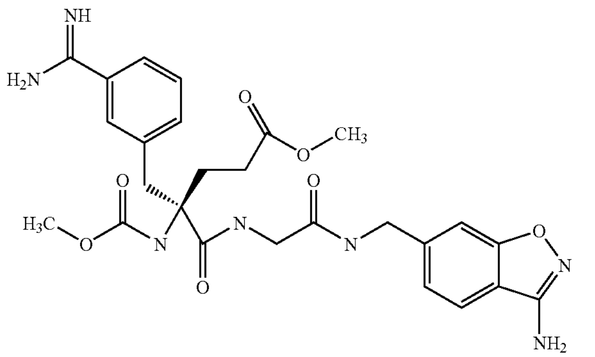 |
| 42 | 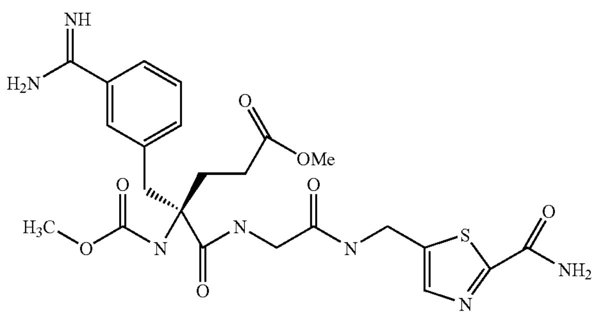 |
| 43 | 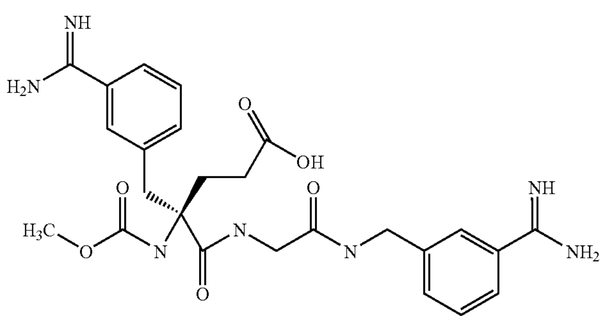 |
| 44 | 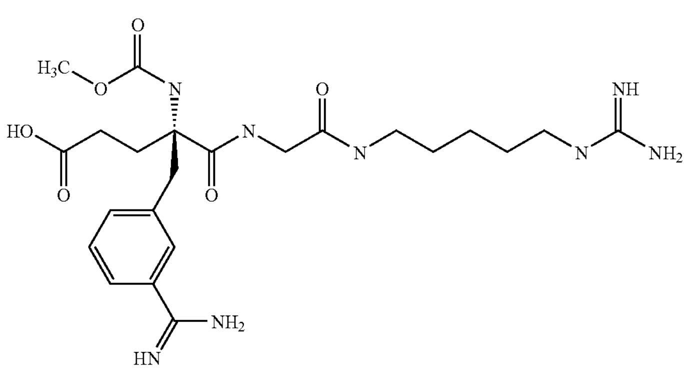 |

TABLE I-continued
| Compound | Structure |
|---|---|
| 45 | 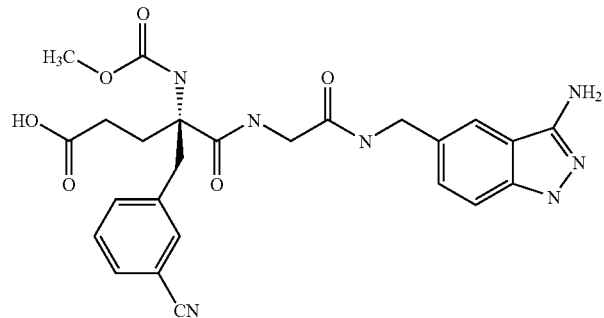 |
| 46 | 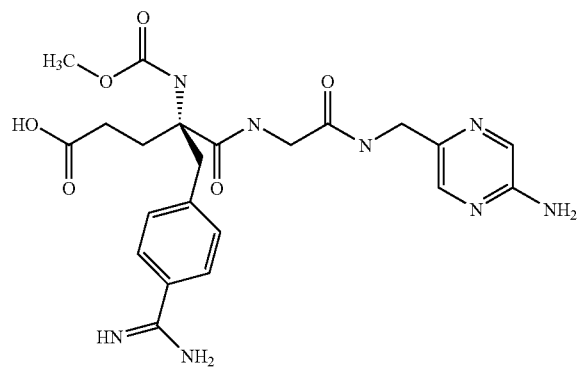 |
| 47 | 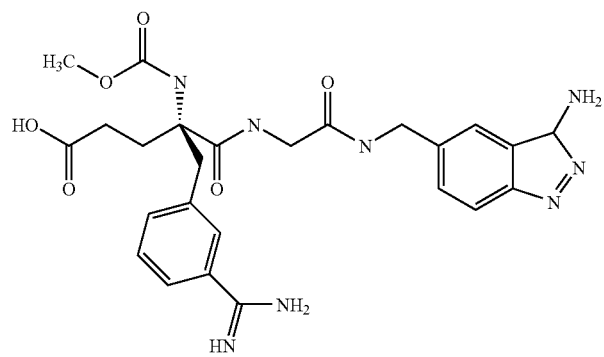 |
| 48 | 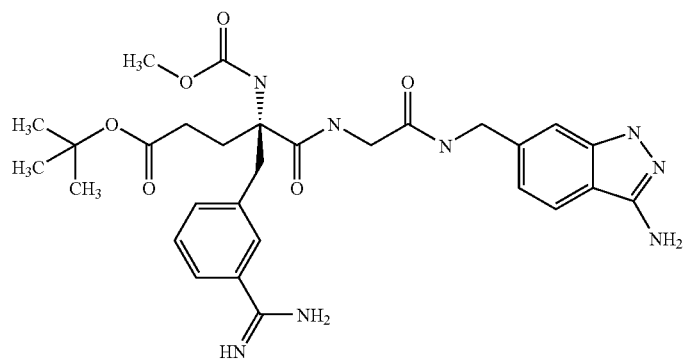 |

TABLE I-continued

| Compound | Structure |
|---|---|
| 49 | 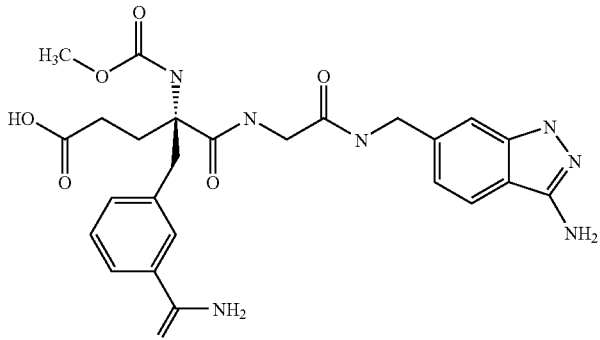 |
| 50 | 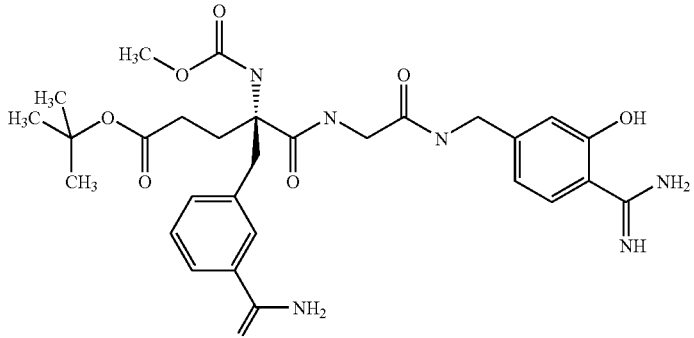 |
| 51 | 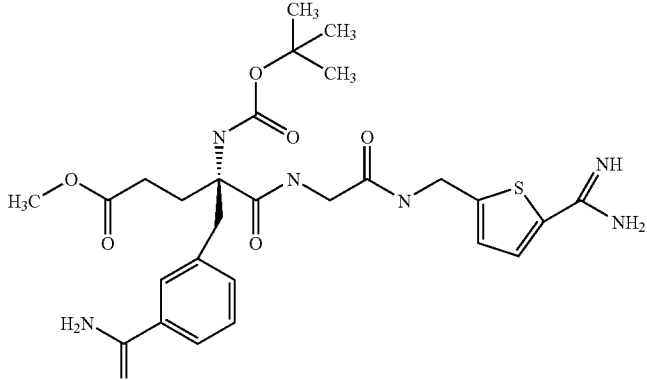 |

A. Preparation of the Preferred Compounds

Certain of the compounds of the present invention which have activity as inhibitors of matriptase or MTSP1 can be conveniently prepared by following the synthetic methods and techniques described in U.S. Pat. Nos. 5,492,895; 5,534, 498, 5,658,939; 5,696,231; 5,681,844; 5,703,208; 5,714, 499; 5,731,413; 5,739,112; 5,770,600; 5,883,077; 5,886, 146; 6,034,215; 6,025,472; WO 00/05245; and Tamura, et al., *Bioorganic & Medicinal Chemistry Letters*, 9:2573–2578 (1999), the disclosures of which are incorporated by reference herein.

Figure 2:
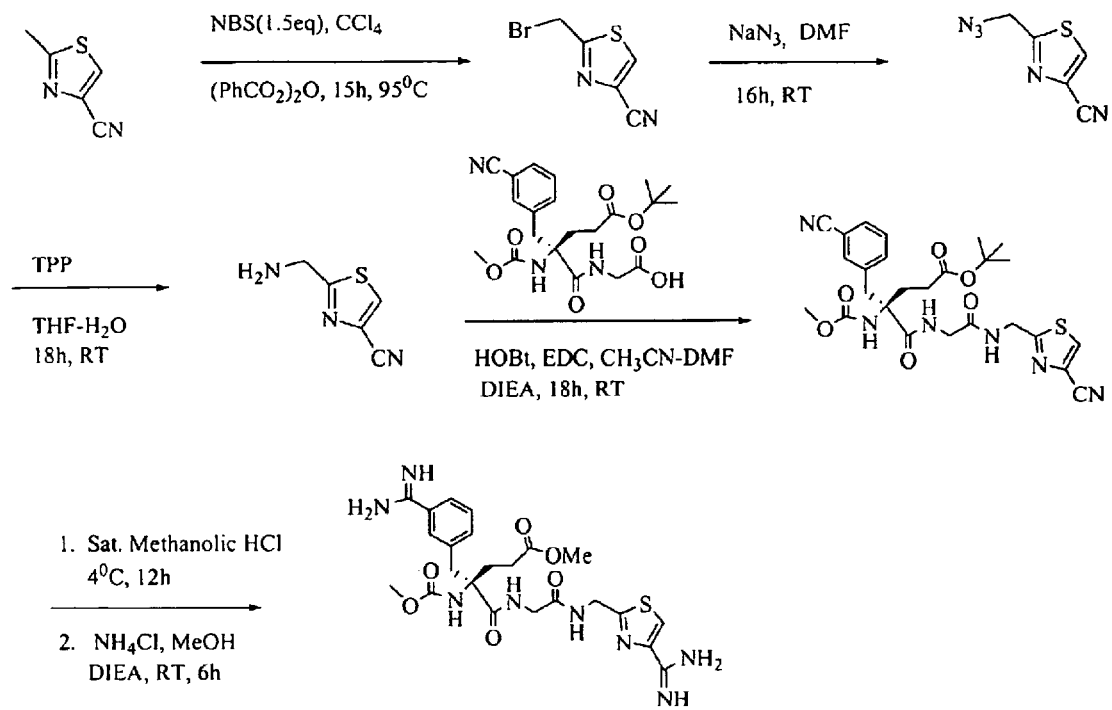
FIG. 2 illustrates a synthetic scheme for certain embodiments of the present invention.

FIGS. 1–2 depict a synthetic scheme for the preparation of Compound Nos. 1–3.

By substituting the appropriate reagents at various points in the reaction scheme depicted in FIGS. 1–2 and described in Examples 1–6, the compounds of Formula I can be conveniently synthesized.

B. Selection of Preferred Compounds

According to one aspect of the present invention, compounds of the present invention are selected for their potency and selectivity in inhibiting serine protease activity of matriptase or MTSP1. As described in Example section, and as is generally known, a target serine protease and its substrate are combined under assay conditions permitting reaction of the protease with its substrate. The assay is performed in the absence of a test compound, and in the presence of increasing concentrations of the test compound. The concentration of test compound at which 50% of the serine protease activity is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the serine protease than those compounds having higher $IC_{50}$ or $EC_{50}$ values. The $IC_{50}$ measurement is often used for more simplistic assays, whereas the $EC_{50}$ is often used for more complicated assays, such as those employing cells.

Preferred compounds according to this aspect of the present invention have an $IC_{50}$ value of 100 nM or less as measured in an in vitro assay for inhibition of serine protease activity of matriptase or MTSP1 activity. Especially preferred compounds have an $IC_{50}$ value of less than 30 nM.

The test compounds also are evaluated for selectivity toward inhibiting serine protease activity of matriptase or MTSP1 in relation to other serine proteases (see, Example section). As described in the Examples, and as generally known, a test compound is assayed for its potency toward a panel of serine proteases and other enzymes and an $IC_{50}$ value or $EC_{50}$ value is determined for each test compound in each assay system. A compound that demonstrates a low $IC_{50}$ value or $EC_{50}$ value for the target enzyme, e.g., the serine protease domain of matriptase or MTSP1, and a higher $IC_{50}$ value or $EC_{50}$ value for other enzymes within the test panel (e.g., tissue plasminogen activator, thrombin, Factor Xa), is considered to be selective toward the target enzyme. Generally, a compound is deemed selective if its $IC_{50}$ value or $EC_{50}$ value in the target enzyme assay is less than one half, preferably one-fifth and more preferably one order of magnitude less than the next smallest $IC_{50}$ value or $EC_{50}$ value measured in the selectivity panel of enzymes.

III. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, but will depend on such factors as weight, diet, concurrent medication and other factors which those skilled in the medical arts will recognize.

The therapeutically effective amount of the compound of the present invention can range broadly depending upon the desired effects and the therapeutic indication. Typically, dosages will be between about 0.01 mg/kg and 100 mg/kg body weight, preferably between about 0.01 and 10 mg/kg body weight.

Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

IV. Utility

The compounds of the present invention have matriptase inhibitory activity.

The compounds of the present invention are active as inhibitors of matriptase and specifically bind matriptase. More particularly, preferred compounds bind to the serine protease domain of matriptase and inhibit its activity.

It is believed that these compounds will be useful in the prevention or treatment of cancerous conditions where that cancerous condition is exacerbated by the activity of matriptase.

Another use for the compounds of the present invention is to decrease progression of cancerous conditions and the concomitant degradation of the cellular matrix.

The compounds of the present invention are active as inhibitors of serine protease activity of matriptase or MTSP1 and specifically bind to the serine protease domain of matriptase or MTSP1. Accordingly, those compounds that contain sites suitable for linking to a solid/gel support may be used in vitro for affinity chromatography to purify matriptase from a sample or to remove matriptase from a sample using conventional affinity chromatography procedures. These compounds are attached or coupled to an affinity chromatography either directly or through a suitable linker support using conventional methods. See, e.g., Current Protocols in Protein Science, John Wiley & Sons (J. E. Coligan et al., eds, 1997) and Protein Purification Protocols, Humana Press (S. Doonan, ed., 1966) and references therein.

The compounds of the present invention having matriptase or MTSP1 serine protease inhibitory activity are useful in in vitro assays to measure matriptase or MTSP1 activity and the ratio of complexed to uncomplexed matriptase or MTSP1 in a sample. These assays could also be used to monitor matriptase or MTSP1 activity levels in tissue samples, such as from biopsy or to monitor matriptase activities and the ratio of complexed to uncomplexed matriptase for any clinical situation where measurement of matriptase or MTSP1 activity is of assistance. An assay which determines serine protease activity in a sample could be used in combination with an ELISA which determines total amount of matriptase or MTSP1 (whether complexed or uncomplexed) in order to determine the ratio of complexed to uncomplexed matriptase.

Various animal models can be used to evaluate the ability of a compound of the present invention to reduce primary tumor growth or to reduce the occurrence of metastasis. These models can include genetically altered rodents (transgenic animals), transplantable tumor cells originally derived from rodents or humans and transplanted onto syngenic or immuno-compromised hosts, or they can include specialized models, such as the CAM model described below, designed to evaluate the ability of a compound or compounds to inhibit the growth of blood vessels (angiogensis) which is believed to be essential for tumor growth. Other models can also be utilized.

Appropriate animal models are chosen to evaluate the in vivo anti-tumor activity of the compounds described in this invention based on a set of relevant criteria. For example, one criterion might be expression of matriptase or MTSP1 and/or matriptase or MTSP1 mRNA by the particular tumor being examined. Two human prostate derived tumors that meet this criterion—are the LnCap and PC-3 cell lines. Another criterion might be that the tumor is derived from a tissue that normally expresses high levels of matriptase or MTSP1. Human colon cancers meet this criterion. A third criterion might be that growth and/or progression of the tumor is dependent upon processing of a matriptase or MTSP1 substrate (e.g., sc-u-PA). The human epidermoid cancer Hep-3 fits this criterion. Another criterion might be that growth and/or progression of the tumor is dependent on a biological or pathological process that requires matriptase or MTSP1 activity. Another criterion might be that the particular tumor induces expression of matriptase or MTSP1 by surrounding tissue. Other criteria may also be used to select specific animal models.

Once appropriate tumor cells are selected, compounds to be tested are administered to the animals bearing the selected tumor cells, and subsequent measurements of tumor size and/or metastatic spread are made after a defined period of growth specific to the chosen model.

The CAM model (chick embryo chorioallantoic membrane model), first described by Ossowski, L., *J. Cell Biol.*, 107:2437–2445 (1988), provides another method for evaluating the anti-tumor and anti-angiogenesis activity of a compound.

Tumor cells of various origins can be placed on 10 day old CAM and allowed to settle overnight. Compounds to be tested can then be injected intravenously as described by Brooks et al., *Methods in Molecular Biology*, 129:257–269, (1999). The ability of the compound to inhibit tumor growth or invasion into the CAM is measured 7 days after compound administration.

When used as a model for measuring—the ability of a compound to inhibit angiogensis, a filter disc containing angiogenic factors, such as basic fibroblast growth factor (bFGF) or vascular ediothelial cell growth factor (VEGF), is placed on a 10 day old CAM as described by Brooks et al., *Methods in Molecular Biology*, 129:257–269, (1999). After overnight incubation, compounds to be tested are then administered intravenously. The amount of angiogenesis is measured by counting the amount of branching of blood vessels 48 hours after the administration of compound (*Methods in Molecular Biology*, 129:257–269, (1999)).

The compounds of the present invention are useful in vivo for treatment of pathologic conditions which would be ameliorated by decreased serine protease activity of matriptase or MTSP1.

It is believed these compounds will be useful in decreasing or inhibiting metastasis, and degradation of the extracellular matrix in tumors and other neoplasms. These compounds will be useful as therapeutic agents in treating conditions characterized by pathological degradation of the extracellular matrix, including those described hereinabove in the Background and Introduction to the Invention.

The present invention includes methods for preventing or treating a condition in a mammal suspected of having a condition which will be attenuated by inhibition of serine protease activity of matriptase or MTSP1 comprising administering to said mammal a therapeutically effective amount of a compound which selectively inhibits serine protease activity of matriptase or MTSP1 or a pharmaceutical composition of the present invention.

The compounds of the present invention are administered in vivo, ordinarily in a mammal, preferably in a human. In employing them in vivo, the compounds can be administered to a mammal in a variety of ways, including orally, parenterally, intravenously, subcutaneously, intramuscularly, colonically, rectally, nasally or intraperitoneally, employing a variety of dosage forms.

In practising the methods of the present invention, the compounds of the present invention are administered alone or in combination with one another, or in combination with other therapeutic or in vivo diagnostic agents.

As is apparent to one skilled in the medical art, a "therapeutically effective amount" of the compounds of the present invention will vary depending upon the age, weight and mammalian species treated, the stage of the disease or pathologic condition being treated, the particular compounds employed, the particular mode of administration and the desired effects and the therapeutic indication. Because these factors and their relationship to determining this amount are well known in the medical arts, the determination of therapeutically effective dosage levels, the amount necessary to achieve the desired result of inhibiting matriptase or MTSP1 serine protease activity, will be within the ambit of one skilled in these arts. Typically, administration of the compounds of the present invention is commenced at lower dosage levels, with dosage levels being increased until the desired effect of inhibiting matriptase or MTSP1 activity to the desired extent is achieved, which would define a therapeutically effective amount. For the compounds of the present invention such doses are between about 0.01 mg/kg and about 100 mg/kg body weight, preferably between about 0.01 and about 10 mg/kg body weight.

In addition, the compounds are suitable to treat other conditions including, but not limited to, unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

An effective quantity of the compound of interest is employed in treatment. The appropriate dosage for treatment will be clear to one of skill in the art. The dosage of compounds used in accordance with the invention varies depending on the compound and the condition being treated. The age, lean body weight, total weight, body surface area, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

EXAMPLES

A. Assays

1. Amidolytic Assay for Determining Inhibition of Serine Protease Activity of Matriptase or MTSP1

The ability of the compounds of the present invention to act as inhibitors of rMAP catalytic activity was assessed by determining the inhibitor-induced inhibition of amidolytic activity by the rMAP, as measured by $IC_{50}$ values.

The assay buffer was HBSA (10 mM Hepes, 150 mM sodium chloride, pH 7.4, 0.1% bovine serum albumin). All reagents were from Sigma Chemical Co. (St. Louis, Mo.), unless otherwise indicated.

Two $IC_{50}$ assays (a) one at either 30-minutes or 60-minutes (a 30-minute or a 60-minute preincubation of test compound and enzyme) and (b) one at 0-minutes (no preincubation of test compound and enzyme) were conducted.

For the $IC_{50}$ assay at either 30-minutes or 60-minutes, the following reagents were combined in appropriate wells of a Corning microtiter plate: 50 microliters of HBSA, 50 microliters of the test compound, diluted (covering a broad concentration range) in HBSA (or HBSA alone for uninhibited velocity measurement), and 50 microliters of the rMAP (Corvas International) diluted in buffer, yielding a final enzyme concentration of 250 pM as determined by active site filtration. Following either a 30-minute or a 60-minute incubation at ambient temperature, the assay was initiated by the addition of 50 microliters of the substrate S-2765 (N-α-Benzyloxycarbonyl-D-arginyl-L-glycyl-L-arginine-p-nitroaniline dihydrochloride; DiaPharma Group, Inc.; Franklin, Ohio) to each well, yielding a final assay volume of 200 microliters and a final substrate concentration of 100 µM (about 4-times $K_m$). Before addition to the assay mixture, S-2765 was reconstituted in deionized water and diluted in HBSA. For the $IC_{50}$ assay at 0 minutes; the same reagents were combined: 50 microliters of HBSA, 50 microliters of the test compound, diluted (covering the identical concentration range) in HBSA (or HBSA alone- for uninhibited velocity measurement), and 50 microliters of the substrate S-2765. The assay was initiated by the addition of 50 microliters of rMAP. The final concentrations of all components were identical in both $IC_{50}$ assays (at 30- or 60- and 0-minute).

The initial velocity of chromogenic substrate hydrolysis was measured in both assays by the change of absorbance at 405 nm using a Thermo Max® Kinetic Microplate Reader (Molecular Devices) over a 5 minute period, in which less than 5% of the added substrate was utilized. The concentration of added inhibitor, which caused a 50% decrease in the initial rate of hydrolysis was defined as the respective $IC_{50}$ value in each of the two assays (30- or 60-minutes and 0-minute).

2. In vitro Enzyme Assays for Specificity Determination

The ability of compounds to act as a selective inhibitor of matriptase activity was assessed by determining the concentration of test-compound which inhibited the activity of matriptase by 50%, ($IC_{50}$) as described in Example A, and comparing $IC_{50}$ value for matriptase to that determined for all or some of the following serine proteases: thrombin, recombinant tissue plasminogen activator (rt-PA), plasmin, activated protein C, chymotrypsin, factor Xa and trypsin.

The buffer used for all assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_0$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

3. Thrombin (fIIa) Assay

Enzyme activity was determined using the chromogenic substrate, Pefachrome t-PA ($CH_3SO_2$-D-hexahydrotyrosine-glycyl-L-Arginine-p-nitroaniline, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 μL), α-thrombin (50 μL) (the final enzyme concentration is 0.5 nM) and inhibitor (50 μL) (covering a broad concentration range), were combined in appropriate wells and incubated for 30 minutes at room temperature prior to the addition of substrate Pefachrome-t-PA (50 μL) (the final substrate concentration is 250 μM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

4. Factor Xa

Factor Xa catalytic activity was determined using the chromogenic substrate S-2765 (N-benzyloxycarbonyl-D-arginine-L-glycine-L-arginine-p-nitro aniline), obtained from DiaPharma Group (Franklin, Ohio). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. *Arch. Biochem. Biophys.* 273:375–388 (1989)]. The enzyme was diluted into HBSA prior to assay in which the final concentration was 0.25 nM.

5. Recombinant Tissue Plasminogen Activator (rt-PA) Assay rt-PA catalytic activity was determined using the substrate, Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

6. Plasmin Assay

Plasmin catalytic activity was determined using the chromogenic substrate, S-2366 [L-pyroglutamyl-L-prolyl-L-arginine-p-nitroaniline hydrochloride], which was obtained from DiaPharma group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

7. Activated Protein C (aPC) Assay aPC catalytic activity was determined using the chromogenic substrate, Pefachrome PC (delta-carbobenzloxy-D-lysine-L-prolyl-L-arginine-p-nitroailine dihydrochloride), obtained from Pentapharm Ltd.). The substrate was made up in deionized water followed by dilution in HBSA prior to the assay in which the final concentration was 400 micromolar (about 3-times Km). Purified human aPC was obtained from Hematologic Technologies, Inc. The enzyme was diluted into HBSA prior to assay in which the final concentration was 1.0 nM.

8. Chymotrypsin Assay

Chymotrypsin catalytic activity was determined using the chromogenic substrate, S-2586 (methoxy-succinyl-L-arginine-L-prolyl-L-tyrosyl-p-nitroanili de), which was obtained from DiaPharma Group. The substrate was made up in deionized water followed by dilution in HBSA prior to the assay in which the final concentration was 100 micromolar (about 9-times Km). Purified (3×-crystallized; CDI) bovine pancreatic alpha-chymotrypsin was obtained from Worthington Biochemical Corp. The enzyme was reconstituted in deionized water and diluted into HBSA prior to assay in which the final concentration was 0.5 nM.

9. Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3×-crystallized; TRL3) bovine pancreatic trypsin was obtained from Worthington Biochemical Corp. The enzyme was reconstituted in deionized water and diluted into HBSA prior to assay in which the final concentration was 0.5 nM.

B. Synthetic Examples

Example 1

MeOCO-(Me)E(α-(3-Amdn)Bn)-G-(4-Amino)pyridine-4-MeAm (Compound 1)

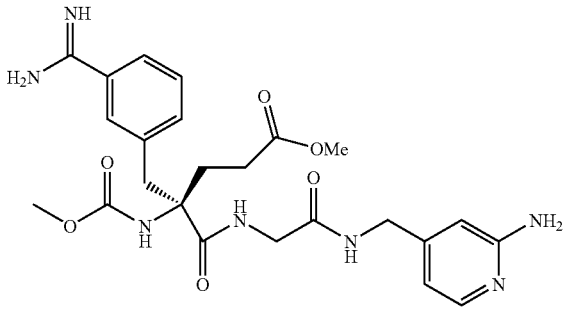

Preparation 1

2-(Di-tert-butyloxycarbonyl)amino-4-picoline

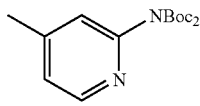

To a solution of 2-amino-4-picoline (2.0 g, 18.49 mmol) in THF (30 mL) were added di-tert-butyl dicarbonate(12.1 g, 55.4 mmol) and 4-N,N-dimethylaminopyridine (7.9 g, 64.71 mmol). The resulting mixture was stirred at room temperature for 15 h then was concentrated under reduced pressure. The crude residue was purified via silica gel column chromatography using EtOAc/n-hexane as eluent to afford the title compound (4.62 g, 73%).

Preparation 2

2-(Di-tert-butyloxycarbonyl)amino-4-(bromomethyl)pyridine

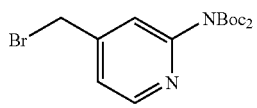

To a mixture of 2-(di-tert-butyloxycarbonyl)amino-4-picoline (2.4 g, 7.78 mmol) and N-bromosuccinimide (2.08 g, 11.7 mmol) in $CCl_4$ (50 mL) was added benzoyl peroxide (0.18 g, 0.77 mmol). The resulting mixture was stirred at 95° C. for 6 h, concentrated under reduced pressure, diluted with EtOAc (100 mL) and washed with saturated $Na_2S_2O_3$ (50 mL), $NaHCO_3$ (50 mL) and brine (20 mL). The organic phase was dried over sodium sulfate and concentrated under reduced pressure. The crude residue was purified via silica gel column chromatography using EtOAc/n-hexane as eluent to afford the title compound (1,9 g, 63%) as a yellow oil.

Preparation 3

2-(Di-tert-butyloxycarbonyl)amino-4-(azidomethyl)pyridine

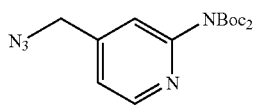

2-(Di-tert-butyloxycarbonyl)amino-4-(bromomethyl)pyridine (2.0 g, 5.18 mmol) was dissolved in 30 mL DMF and sodium azide (0.505 g, 7.7 mmol) was added. The reaction was allowed to stir for 12 h at room temperature and then diluted with water (50 mL). The aqueous layer was extracted with ethyl acetate (3×) and the combined organic layers were washed again with 100 mL of brine, dried with anhydrous sodium sulfate and concentrated in vacuo to yield 1.6 g (88%) of the title compound used in next step without further purification.

Preparation 4

2-(Di-tert-butyloxycarbonyl)amino)-4-(aminomethyl)pyridine

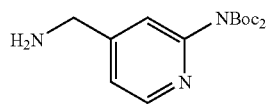

To a magnetically stirred solution of 2-(di-tert-butyloxycarbonyl)amino-4-(azidomethyl)pyridine (1.6 g, 4.5 mmol) in a mixture of THF (20 mL) and water (2 mL) was added triphenylphosphine (1.8 g, 6.87 mmol) portionwise with ice-bath cooling. After the addition was complete, the mixture was stirred for an additional 18 h at room temperature and concentrated under reduced pressure. The crude residue was purified via silica gel column chromatography using EtOAc/n-hexane as eluent to afford the title compound (1.2 g, 60%) as a gummy material.

Preparation 5

MeOCO-(t-Bu)E(α-(3-CN)Bn)-G-(2-di-tert-butyloxycarbonyl)amino)pyridine-4-MeAm

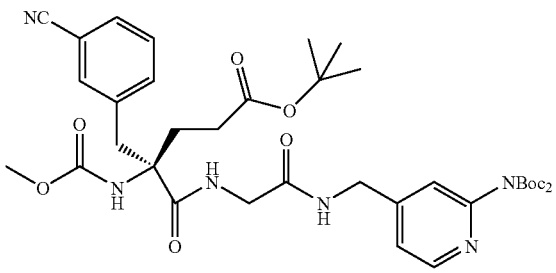

A 100 mL round bottom flask containing a Teflon-coated magnetic stirring bar and a rubber septum was charged with MeOCO-(t-Bu)E((α-(3-CN)Bn)-Glycine (0.5 g, 1.15 mmol), EDC (0.332 g, 1.73 mmol), HOBt (0.212 g, 1.38 mmol), and 2-(di-tert-butyloxy carbonyl)amino)-4-(aminomethyl)pyridine (0.5 g, 1.5 mmol) in acetonitrile (40 mL). The reaction mixture was treated with DIEA (0.523 mL, 3.0 mmol), stirred for 18 h and concentrated. Ethyl acetate (100 mL) and $H_2O$ (50 mL) were added and the biphasic mixture was transferred to a separatory funnel and the phases were separated. The aqueous phase was re-extracted with ethyl acetate (3×50 mL) and the combined organic phases were washed with 0.5 N HCl (2×50 mL), $H_2O$ (50 mL), saturated $NaHCO_3$ solution (2×50 mL), brine (100 mL), dried over magnesium sulfate and concentrated in vacuo. The crude residue (0.712 g, 83%) was used in next step without further purification.

Preparation 6

MeOCO-(Me)E(α-(3-Amdn)Bn)-G-(4-Amino)pyridine-4-MeAm

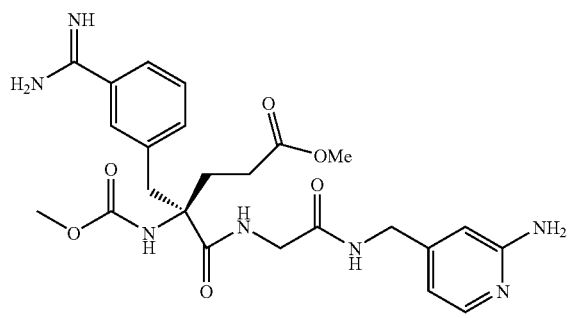

MeOCO-(t-Bu)E(alpha-(3-CN)Bn)-G-(2-di-tert-butyloxycarbonyl)amino)pyridine-4-MeAm (0.712 g, 0.96 mmol) was added to saturated methanolic HCl (10 mL) precooled in an ice bath at 0° C. The reaction mixture was stirred at 4° C. overnight then was concentrated under reduced pressure. The residue was dissolved in 10 mL of methanol. The reaction mixture was treated with ammonium chloride (0.513 g, 9.6 mmol) and DIEA (2.01 mL, 11.5 mmol), stirred for 12 h at room temperature then was concentrated under reduced pressure. The crude residue was purified via RP-HPLC using ACN/H$_2$O/TFA as eluent to afford the title compound (0.36 g, 72%) as a white solid. $^1$H-NMR (D$_2$O) δ 1.96–2.08 (m, 1H), 2.17–2.24 (m, 1H), 2.54–2.57 (m, 2H), 3.24 (d, J=13.6 Hz, 1H), 3.37 (d, J=13.6 Hz, 1H), 3.66 (s, 3H), 3.70 (s, 3H), 3.93 (d, J=7.2 Hz 2H), 4.49 (s, 2H), 6.79–6.82(m, 2H), 7.39–7.50 (m, 2H), 7.57 (t, J=7.6 Hz, 1H), 7.71 (br. d, J=8.0 Hz, 1H), 7.76 (d, J=7.2 Hz, 1H); MS (m/e) 514 (M+1), 257 (M+2/2).

Example 2

MeOCO-(Me)E(α-(3-Amdn)Bn)-G-(4-Amdn)thiazole-2-MeAm (Compound 2)

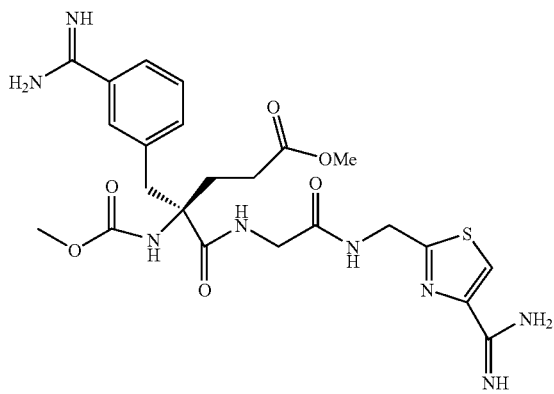

Preparation 1

2-Bromomethyl-thiazole-4-carbonitrile

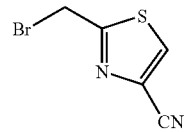

To a mixture of 2-methyl-thiazole-4-carbonitrile (3.0 g, 24.1 mmol), N-bromosuccinimide (4.3 g, 24.1 mmol) in CCl$_4$ (50 mL) was added benzoyl peroxide (0.583 g, 0.10 mmol). The resulting mixture was stirred at 95° C. for 15 h, concentrated under reduced pressure, diluted with EtOAc (100 mL) and washed with saturated Na$_2$S$_2$O$_3$ (50 mL), NaHCO$_3$ (50 mL) and brine (20 mL). The organic phase was dried over sodium sulfate and concentrated under reduced pressure. The crude residue was purified via silica gel column chromatography using EtOAc/n-hexane as eluent to afford the title compound (4.6 g, 83%) as yellow oil. Rf0.39 (silica gel,EtOAc/hexane,3/7).

Preparation 2

2-Azidomethyl-thiazole-4-carbonitrile

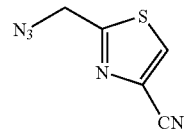

2-Bromomethyl-thiazole-4-carbonitrile (1.6 g, 7.8 mmol) was dissolved in 20 mL DMF and sodium azide (0.768 g, 11.8 mmol) was added. The reaction was allowed to stir for 16 h at room temperature and then diluted with water (50 mL). The aqueous layer was extracted with ethyl acetate (3×) and the combined organic layers were washed again with 75 ml of brine, dried with anhydrous sodium sulfate and concentrated in vacuo to yield 1.20 g (92%) of the title compound as a gummy material which was used in next step with out further purification.

Preparation 3

2-Aminomethyl-thiazole-4-carbonitrile

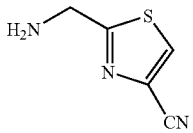

To a magnetically stirred solution of 2-azidomethyl-thiazole-4-carbonitrile (1.3 g, 7.8 mmol) in a mixture of THF (40 mL) and water (4 mL) was added triphenylphosphine (3.10 g, 11.8 mmol) portionwise with ice-bath cooling. After the addition was complete, the mixture was stirred for an additional 18 h at room temperature and extracted with 3% hydrochloric acid (10 mL). The resultant aqueous solution was extracted with ether, basified to pH=12 with 3N NaOH, extracted into ethyl acetate (3×), and the combined organic layers were washed with 100 mL of brine, dried with anhydrous magnesium sulfate and concentrated in vacuo to yield 1.0 g (91%) of the title compound as an oil which was used in next step with out further purification.

Preparation 4

MeOCO-(t-Bu)E(alpha-(3-CN)Bn)-G-(4-CN) thiazole-2-MeAm

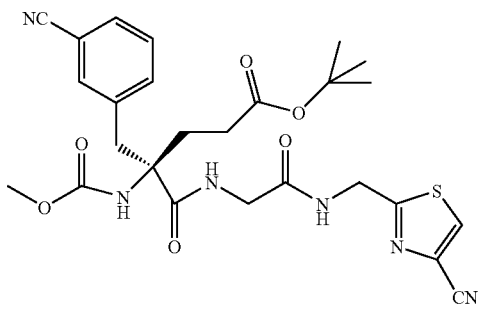

A 100 mL round bottom flask containing a Teflon-coated magnetic stirring bar and a rubber septum was charged with MeOCO-(t-Bu)E(α-(3-CN)Bn)-Glycine (3.1 g, 7.1 mmol), EDC (2.06 g, 10.7 mmol), HOBt (1.32 g, 8.6 mmol), and 2-aminomethyl-thiazole-4-carbonitrile (1.30 g, 9.3 mmol) in acetonitrile (40 mL) and DMF (3 mL). The reaction mixture was treated with DIEA (3.24 mL, 18.6 mmol), stirred for 18 h and concentrated. Ethyl acetate (100 mL) and H$_2$O (50 mL) were added and the biphasic mixture was transferred to a separatory funnel and the phases were separated. The aqueous phase was re-extracted with ethyl acetate (3×50 mL) and the combined organic phases were washed with 0.5 N HCl (2×50 mL), H$_2$O (50 mL), saturated NaHCO$_3$ solution (2×50 mL), brine (100 mL), dried (MgSO$_4$), filtered and concentrated in vacuo. The crude residue was purified via RP-HPLC using ACN/H$_2$O/TFA as eluent to afford the title compound (2.98 g, 75%) as an off white solid.

Preparation 5

MeOCO-(Me)E(α-(3-Amdn)Bn)-G-(4-Amdn) thiazole-2-MeAm (Compound 2)

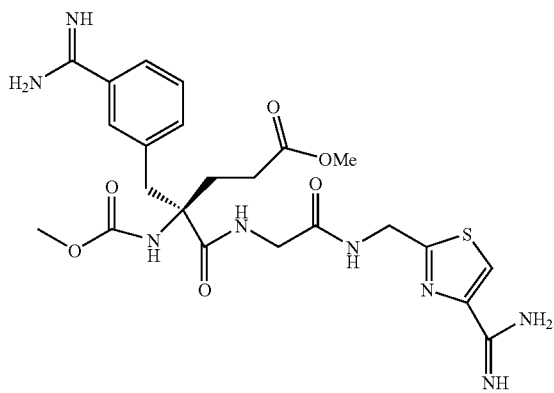

MeOCO-(t-Bu)E(alpha-(3-CN)Bn)-G-(4-CN)thiazole-2-MeAm (0.5 g, 0.90 mmol) was added to saturated methanolic HCl (3 mL) at 0° C. with ice bath cooling. The reaction mixture was stirred at 4° C. overnight then is concentrated under reduced pressure. The residue was dissolved in 8 mL of methanol. The reaction mixture was treated with ammonium chloride (0.48 g, 9.0 mmol) and DIEA (1.88 mL, 10.8 mmol), stirred for 6 h at room temperature then is concentrated under reduced pressure. The crude residue was purified via RP-HPLC using ACN/H$_2$O/TFA as eluent to afford the title compound (0.386 g, 78%) as a white solid. $^1$H-NMR (D$_2$O) δ 1.94–2.08 (m, 1H), 2.16–2.25 (m, 1H), 2.50–2.56 (m, 2H), 3.23 (d, J=14.0 Hz, 1H), 3.36 (d, J=14.0 Hz, 1H), 3.66 (s, 3H), 3.70 (s, 3H), 3.93 (d, J=4.0 Hz 2H), 4.8 (d, J=4.4 Hz, 2H), 7.49–7.52 (m, 2H), 7.57 (d, J=7.6 Hz, 1H), 7.71 (d, J=7.6 Hz, 1H), 8.54 (s, 1H); MS (m/e) 547 (M+1), 274 (M+2/2).

Example 3

N-MeOCO-(α-(3-Am)4-pyrMe)M(O$_2$)-G-(2-Amdn) thiophene-5-MeAm (Compound 3)

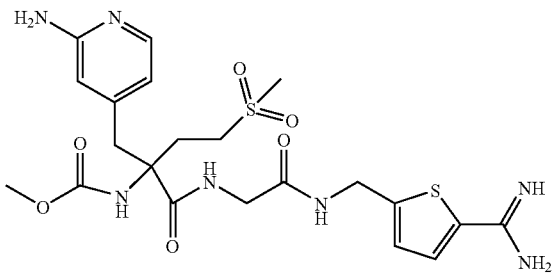

Preparation 1

2-[(4-Chlorobenzylidene)-amino]-4-methylsulfanyl-butyric acid methyl ester

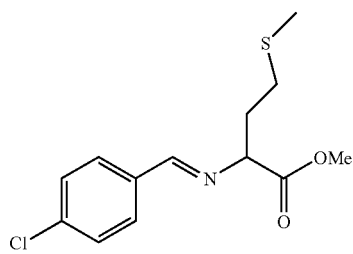

To a solution of L-methionine methyl ester hydrochloride (2 g, 10.0 mmol) and sodium carbonate (1.06 g, 10.0 mmol) in water (46 mL) was added p-chlorobenzaldehyde (1.4 g, 10.0 mmol). The resulting mixture was stirred at 40° C. for 45 minutes then 17 h at room temperature. The white cloudy solution was extracted with dichloromethane (3×50 mL). The organic phase was washed with water (2×50 mL), dried over anhydrous magnesium sulfate and concentrated in vacuo to yield the title compound 2.6 g (91%) which was used in next step with out further purification.

Preparation 2

2-Amino-2-(2-di-tert-butoxycarbonylamino-pyridin-4ylmethyl)-4-methylsulfanyl-butyric acid methyl ester

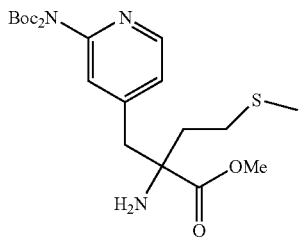

To a magnetically stirred solution of 2-[(4-chlorobenzylidene)-amino]-4-methylsulfanyl-butyric acid methyl ester (0.3 g, 1.05 mmol), 2-(di-tert-butyloxycarbonyl)amino-4-(bromomethyl)pyridine (0.82 g, 2.1 mmol) and tetrabutylammonium chloride (3.1 mg, 0.01 mmol) in toluene (10 mL) was added cesium hydroxide monohydrate (0.879, 5.25 mmol) portion wise at 0° C. After the addition was complete, the mixture was stirred for 1.5 h at 0° C. The reaction mixture turned to a cloudy yellow color. The reaction mixture was diluted with water (15 mL), diluted with dichloromethane (50 mL), and was concentrated under reduced pressure. The crude residue was dissolved in THF (10 mL) and was added to citric acid solution (0.5 M, 10 mL). The mixture was stirred for an additional 1 h at room temperature and the biphasic mixture was transferred to a separatory funnel. The aqueous phase was washed with ether (3×10 mL) to remove other impurities. The aqueous layer was basified with saturated NaHCO₃ solution until pH=9 and extracted with 30 mL of dichloromethane. The combined organic layers were dried over anhydrous sodium sulfate, and concentrated in vacuo to yield the title compound 0.398 g (80%) that was used directly in next step without further purification.

Preparation 3

2-(2-di-tert-Butoxycarbonylamino-pyridin-4-ylmethyl)-2-methoxycarbonylamino-4-methylsulfanyl-butyric acid methyl ester

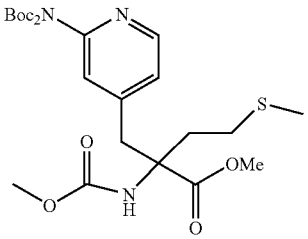

2-Amino-2-(2-di-tert-butoxycarbonylamino-pyridin-4ylmethyl)-4-methylsulfanyl-butyric acid methyl ester (0.20 g, 0.42 mmol) was dissolved in 5 mL of THF. Methyl chloroformate (0.05 mL, 0.55 mmol) and DIEA (0.154 mL, 0.88 mmol) were added to the reaction mixture and stirred for 1 h at room temperature. Water (10 mL) was added, stirred for 20 min and the biphasic mixture was transferred to a separatory funnel. The organic phase was separated and the aqueous phase was re-extracted with EtOAc (3×10 mL) and the combined organic phases were washed with 5% HCl (2×10 mL), H₂O (10 mL), NaHCO₃ (saturated, 2×10 mL), H₂O (20 mL), brine (10 mL), dried (MgSO₄), filtered and concentrated to give pale yellow oil. The crude residue was purified via silica gel column chromatography using EtOAc/n-hexane as eluent to afford the title compound (0.2 g, 89%) as oil.

Preparation 4

2-(2-di-tert-Butoxycarbonylamino-pyridin-4-methanesulfonyl-2-methoxy-carbonylamino-butyric acid

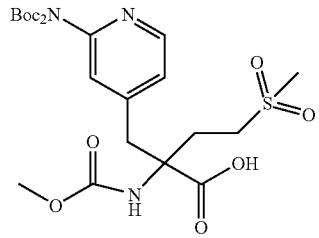

To a magnetically stirred solution of 2-(2-di-tert-Butoxycarbonylamino-pyridin-4-ylmethyl)-2-methoxycarbonylamino-4-methylsulfanyl-butyric acid methyl ester (0.2 g, 0.37 mmol) in a mixture of acetone (10 mL) and water (10 mL) was added Oxone® (2.3 g, 3.7 mmol). After the addition was complete, the mixture was stirred for an additional 16 h at room temperature then was concentrated under reduced pressure. The crude residue was diluted with water (15 mL), extracted in to dichloromethane (50 mL), the combined organic layers were washed with 20 mL of brine, dried with anhydrous magnesium sulfate and concentrated in vacuo. To the crude residue, dissolved in a mixture of THF (4 mL) and water (1 mL) was added LiOH solution (1M, 0.75 mL, 0.75 mmol). The mixture was stirred for an additional 14 h at room temperature, neutralized with 1M oxalic acid, extracted into dichloromethane (50 mL). The combined organic layers were washed with 20 mL of brine, dried with anhydrous magnesium sulfate, and concentrated in vacuo and used in next step with out further purification.

Preparation 5

N-MeOCO-(α-(3-Am)4-pyrMe)M(O₂)-G-(2-Amdn) thiophene-5-MeAm (Compound 3)

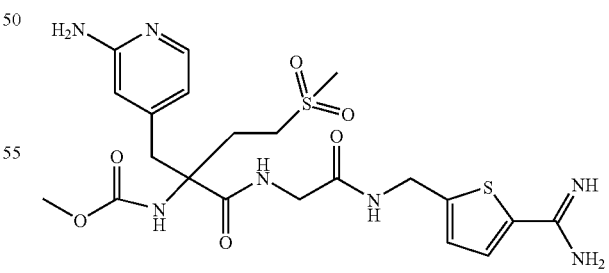

A 100 mL round bottom flask containing a Teflon-coated magnetic stirring bar and a rubber septum was charged with 2-(2-di-tert-Butoxycarbonylamino-pyridin-4-methanesulfonyl-2-methoxycarbonylamino-butyric acid (0.117 g, 0.21 mmol), EDC (0.06 g, 0.31 mmol), HOBt (0.042 g, 0.27 mmol), and 2-amino-N-5-cyano-thiophen-2- ylmethyl)-acetamide hydrochloride (0.074 g, 0.32 mmol) in acetonitrile (10 mL). The reaction mixture was treated with DIEA (0.146 mL, 0.84 mmol), stirred for 12 h, and concentrated. Ethyl acetate (10 mL) and H₂O (3 mL) were added and the biphasic mixture was transferred to a separatory funnel and the phases were separated. The aqueous phase was re-extracted with ethyl acetate (3×10 mL) and the combined organic phases were washed with 0.5 N HCl (2×10 mL), H₂O (20 mL), saturated NaHCO₃ (2×10 mL), brine (30 mL), dried (MgSO₄), filtered and concentrated in vacuo. The crude residue was treated with saturated methanolic HCl (5 mL) at 0° C. via ice bath. The reaction mixture was stirred at 4° C. overnight then was concentrated under reduced pressure. The residue was dissolved in 5 mL of methanol. The reaction mixture was treated with ammonium chloride (0.112 g, 2.1 mmol) and DIEA (0.44 mL, 2.52 mmol), stirred for 6 h at room temperature then was concentrated under reduced pressure. The crude residue was purified via RP-HPLC using ACN/H₂O/TFA as eluent to afford the title compound (0.052 g, 45%) as a white solid. ¹H-NMR (D₂O) δ 2.23–2.40 (m, 2H), 3.10 (s, 3H), 3.18–3.38 (m, 4H), 3.65 (s, 3H), 3.95 (br. s, 2H), 4.69 (d, J=6.8 Hz 2H), 6.67 (dd, J=1.6 and 6.8 Hz, 1H), 6.80 (s, 1H), 7.19 (d, J=4.0 Hz, 1H), 7.72 (d, J=6.4 Hz, 1H), 7.92 (d, J=3.6 Hz, 1H), MS (m/e) 540 (M+1), 270 (M+2/2).

Example 4

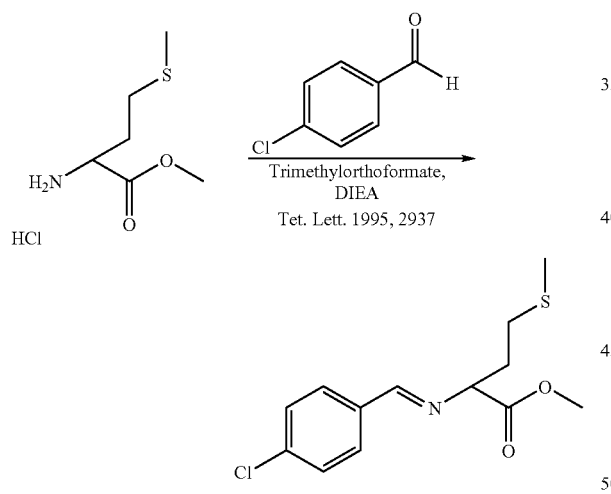

(±)-2-[(4-Chloro-benzylidene)-amino]-4-methylsulfanyl-butyric acid methyl ester.

D,L-Methionine-OMe (2.0 g, 10 mmol) was added to diisopropylethylamine (3.7 mL, 20 mmol) in stirring trimethylorthoformate (20 mL) and the mixture was stirred for 30 min. 4-Chlorobenzaldehyde (1.4 g, 10 mmol) was added to this mixture and the homogeneous solution stirred overnight. The solvent was removed in vacuo to give an oil. This oil was dissolved in ether (50 mL) and washed with water (2×100 mL). The ether layer was dried over magnesium sulfate and evaporated to give an oil as the title compound which was used without further purification (2.84 g, quantitative yield).

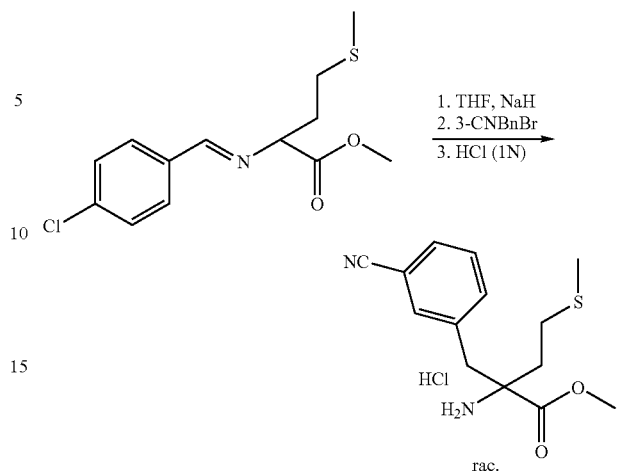

(±)-2-Amino-2-(3-cyano-benzyl)-4-methylsulfanyl-butyric acid methyl ester hydrochloric acid.

NaH (60% suspension in oil, 154 mg, 3.86 mmol) was added in portions to a stirring solution of (±)-2-[(4-chlorobenzylidene)-amino]-4-methylsulfanyl-butyric acid methyl ester (1.0 g, 285 mmol) in THF (20 mL) at rt and the mixture was stirred for 15 min. 3-Cyanobenzylbromide (753 mg, 3.86 mmol) was added and the mixture stirred for 2 h. HCl (1N, 15 mL) was added to this mixture and the resulting suspension (PH≈1–2) was stirred overnight. The reaction mixture was washed with EtOAc (25 mL) and neutralized with NaHCO₃ (sat. in H₂O). The cloudy water layer was extracted with CH₂Cl₂ (3×50 mL), and the combined organic layers were dried over Na₂SO₄ and evaporated to give an oil as the title compound (150 mg, 15% for two steps), MS (electrospray) 279 (M+1).

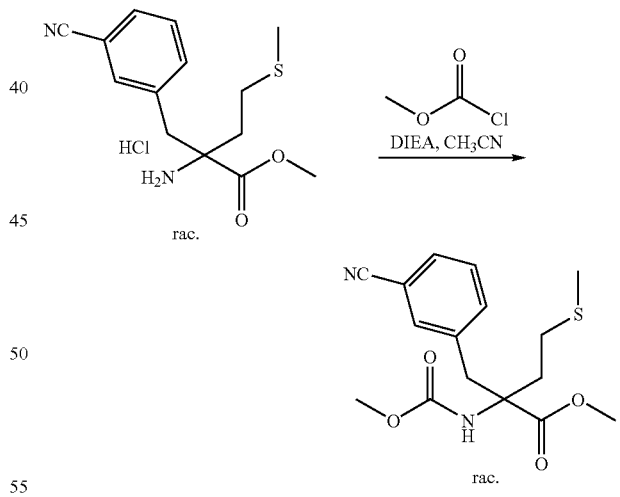

(±)-2-(3-Cyano-benzyl)-2-methoxycarbonylamino-4-methylsulfanyl-butyric acid methyl ester.

Methylchloroformate (80 μL, 1.08 mmol) was added to a stirring mixture of (±)-2-amino-2-(3-cyano-benzyl)-4-methylsulfanyl-butyric acid methyl ester hydrochloric acid (150 mg, 0.540 mmol), and triethylamine (155 μL, 1.08 mmol) in CH₃CN and the mixture stirred overnight. The mixture was diluted with EtOAc (100 mL), and washed with HCl (1N, 50 mL), NaHCO₃ (sat. 50 mL), brine (50 mL), dried over Na₂SO₄ and evaporated to give an oil. Column chromatography (EtOAc/Hexanes, 1:3) gave a transparent oil corresponding to the title compound (154 mg, 85%), MS (electrospray) 337 (M+1).

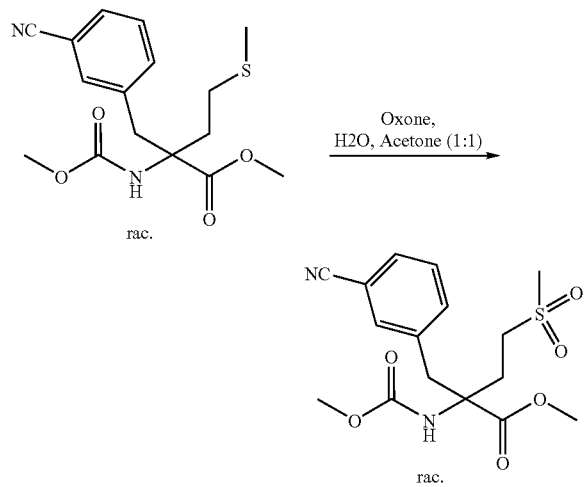

(±)-2-(3-Cyano-benzyl)-4-methanesulfonyl-2-methoxycarbonylamino-butyric acid methyl ester.

Oxone (600 mg) was added to a stirring solution of (±)-2-(3-cyano-benzyl)-2-methoxycarbonylamino-4-methylsulfanyl-butyric acid methyl ester (100 mg, 0.297 mmol) in H₂O/Acetone (1:1, 10 mL) and the mixture was stirred overnight. The solvent was removed to approximately half of the volume and diluted with H₂O (20 mL). The water layer was extracted with EtOAc (2×20 mL), dried over Na₂SO₄ and the solvent removed to give a solid. Column chromatography (MeOH/CH₂Cl₂, 5:95) gave a transparent oil corresponding to the title compound (109 mg, quant.), MS (electrospray) 369 (M+1).

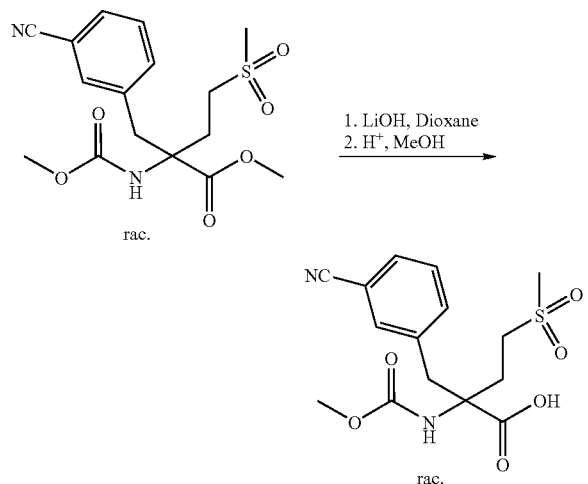

(±)-2-(3-Cyano-benzyl)-4-methanesulfonyl-2-methoxycarbonylamino-butyric acid.

LiOH (2.0 N, 3.0 mL) was added to a stirring solution of (±)-2-(3-cyano-benzyl)-4-methanesulfonyl-2-methoxycarbonylamino-butyric acid methyl ester (700 mg, 1.9 mmol) in Dioxane (10 mL) and the mixture stirred overnight. The solution was acidified using Dowex 50 WX8-400. The solid was removed by filtration and the solvent removed in vacuo to give an oil corresponding to the title compound, MS (electrospray) 353 (M-1).

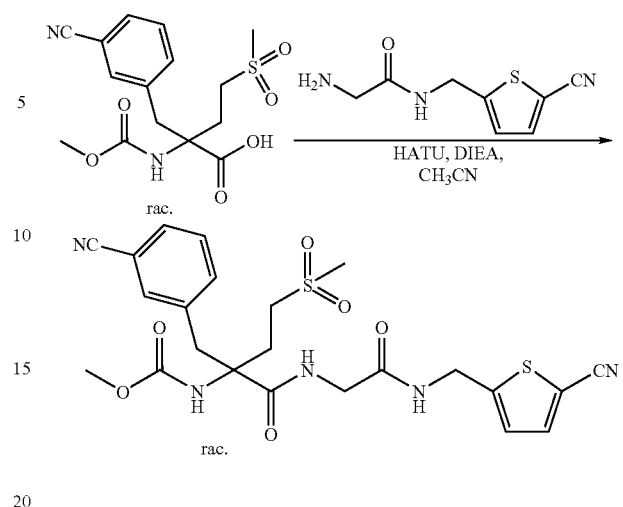

(±)-[1-(3-Cyano-benzyl)-1-({[(5-cyano-thiophen-2-ylmethyl)-carbamoyl]-methyl}-carbamoyl)-3-methanesulfonyl-propyl]-carbamic acid methyl ester.

A solution of 2-amino-N-(5-cyano-thiophen-2-ylmethyl)-acetamide (150 mg, 0.485 mmol), (±)-2-(3-cyano-benzyl)-4-methanesulfonyl-2-methoxycarbonylamino-butyric acid (172 mg, 0.485 mmol), HATU (369 mg, 0.97 mmol), and DIEA (178 μL, 0.97 mmol) in acetonitrile (5.0 mL) was stirred at rt overnight. The solution was diluted with EtOAc (20 mL) washed with HCl (1M, 10 mL), NaHCO₃ (sat., 10 mL), brine (10 mL), and removed in vacuo to give an oil. Column chromatography (MeOH/CH₂Cl₂, 5:95) gave an oil corresponding to the title compound (100 mg, 39%), MS (electrospray) 532 (M+1).

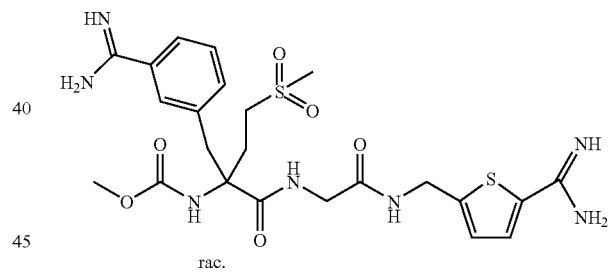

(±)-[1-(3-Carbamimidoyl-benzyl)-1-({[(5-carbamimidoyl-thiophen-2-ylmethyl)-carbamoyl]-methyl}-carbamoyl)-3-methanesulfonyl-propyl]-carbamic acid methyl ester. (Compound 4)

(±)-[1-(3-Cyano-benzyl)-1-({[(5-cyano-thiophen-2-ylmethyl)-carbamoyl]-methyl}-carbamoyl)-3-methanesulfonyl-propyl]-carbamic acid methyl ester (100 mg, 0.189 mmol) was added to sat. HCl in MeOH (10 mL) and the mixture stirred overnight. The solvent was removed in vacuo and diluted in MeOH (5 mL). To this solution was added NH₄Cl (1.0 g, 19 mmol), and TEA (500 μL, 7.0 mmol) and the heterogeneous mixture was stirred for 2 days. HPLC purification (CH₃CN, H₂O, 0.1% TFA) gave a fluffy white solid as the title compound, MS (electrospray) 566 (M+1); 283 (M+2). ¹H NMR (CD₃OD); 2.2 (m, 2H), 3.0 (s, 3H), 3.3–3.4 (m, 4H), 3.37 (s, 3H), 3.87 (d, J=3.0 Hz, 2H), 3.65 (d, J=3.0 Hz 2H), 7.19 (d, 1H), 7.50 (m, 2H), 7.57 (t, 1H), 7.65 (s, 1H), 7.70 (m, 1H), 7.80 (d, 1H), 8.60 (m, 1H), 8.78 (m, 1H)

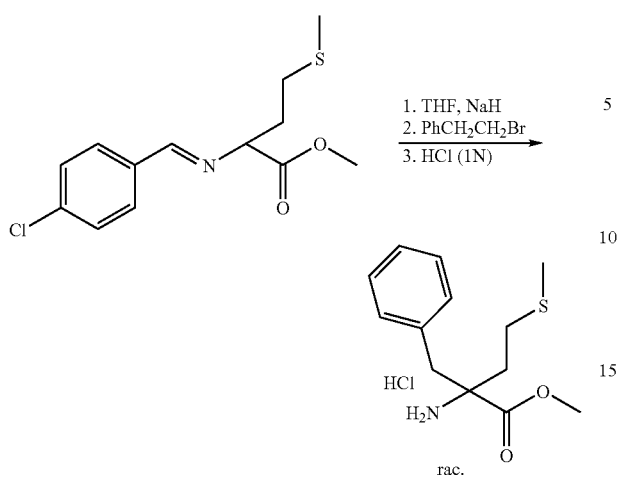

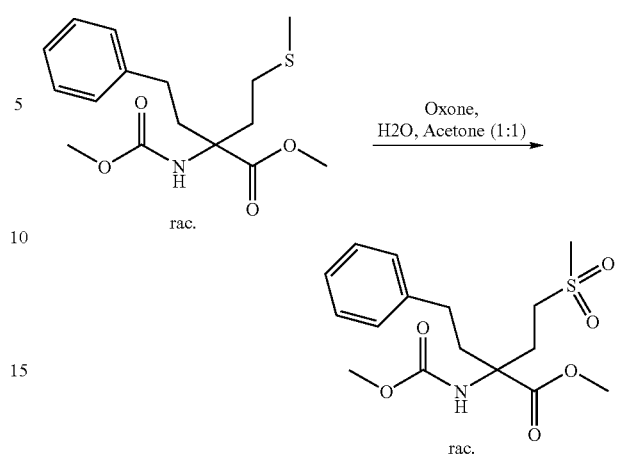

(±)-2-Amino-4-methylsulfanyl-2-phenethyl-butyric acid methyl ester hydrochloric acid.

NaH (60% suspension in oil, 461 mg, 11.2 mmol) was added in portions to a stirring solution of (±)-2-[(4-chlorobenzylidene)-amino]-4-methylsulfanyl-butyric acid methyl ester (3.0 g, 10.5 mmol) in DMF (10 mL) at rt and the mixture stirred for 15 min. (2-Bromoethyl) benzene (2.14 g, 11.6 mmol) was added and the mixture stirred for 2 h. To this mixture was added HCl (1N, 20 mL) and the resulting suspension was stirred overnight. The reaction mixture was washed with EtOAc (25 mL) and neutralized with NaHCO$_3$ (sat. in H$_2$O). The cloudy water layer was extracted with CH$_2$Cl$_2$ (3×50 mL). The combined organic layers were dried over Na$_2$SO$_4$ and removed in vacuo to give an oil as the title compound (832, 30%), MS (electrospray) 268 (M+1).

(±)-4-Methanesulfonyl-2-methoxycarbonylamino-2-phenethyl-butyric acid methyl ester.

Oxone (6.1 g) was added to a stirring solution of (±)-2-methoxycarbonylamino-4-methylsulfanyl-2-phenethyl-butyric acid methyl ester (610 mg, 1.88 mmol) in H$_2$O/Acetone (1:1, 18 mL) and the mixture stirred over night. The solvent was removed in vacuo to approximately half of the volume and diluted with H$_2$O (20 mL). The water layer was extracted with EtOAc (2×20 mL), dried over Na$_2$SO$_4$ and the solvent removed in vacuo to give a solid. Column chromatography (MeOH/CH$_2$Cl$_2$, 5:95) gave the a transparent oil corresponding to the title compound (670 mg, quant.), MS (electrospray) 358 (M+1).

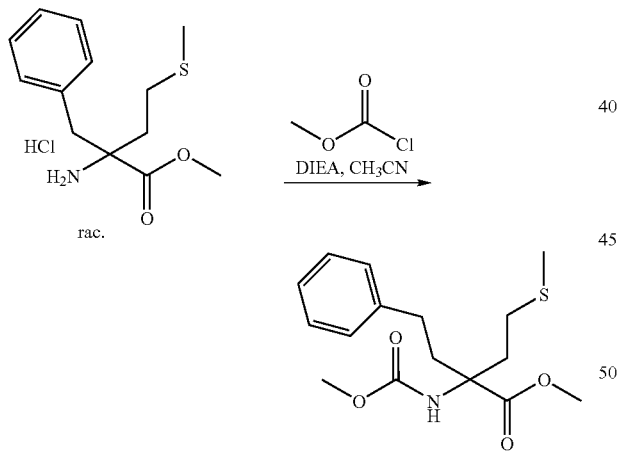

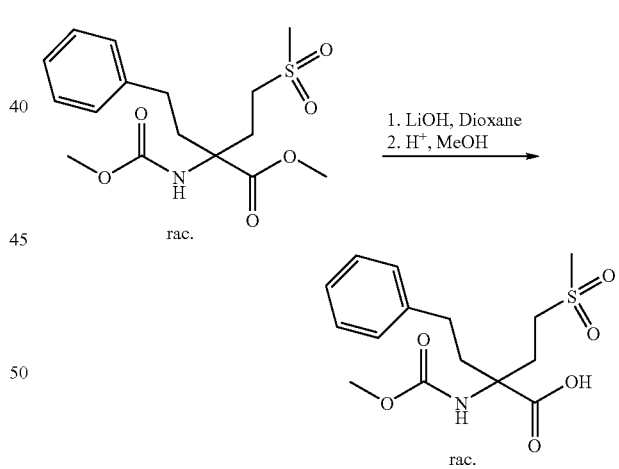

(±)-2-Methoxycarbonylamino-4-methylsulfanyl-2-phenethyl-butyric acid methyl ester.

Methylchloroformate (479 µL, 3.74 mmol) was added to a stirring mixture of (±)-2-amino-4-methylsulfanyl-2-phenethyl-butyric acid methyl ester hydrochloric acid (832 mg, 3.11 mmol), and DIEA (1.1 mL, 6.23 mmol) in CH$_3$CN (10 mL) and the mixture stirred overnight. The mixture was diluted with EtOAc (100 mL), and washed with HCl (1N, 50 mL), NaHCO$_3$ (sat. 50 mL), brine (50 mL), dried over Na$_2$SO$_4$ and evaporated to give an oil. Column chromatography (EtOAc/Hexanes, 1:3) gave a transparent oil corresponding to the title compound (610 mg, 60%), MS (electrospray) 326 (M+1).

(±)-4-Methanesulfonyl-2-methoxycarbonylamino-2-phenethyl-butyric acid.

LiOH (1.2 N, 8.3 mL) was added to a stirring solution of (±)-4-methanesulfonyl-2-methoxycarbonylamino-2-phenethyl-butyric acid methyl ester (741 mg, 2.07 mmol) in Dioxane (25 mL) and the mixture stirred overnight. The solution was acidified using Dowex 50 WX8-400. The solid was removed by filtration and the solvent removed in vacuo to give an oil corresponding to the title compound (497 mg, 70%), MS (electrospray) 342 (M−1).

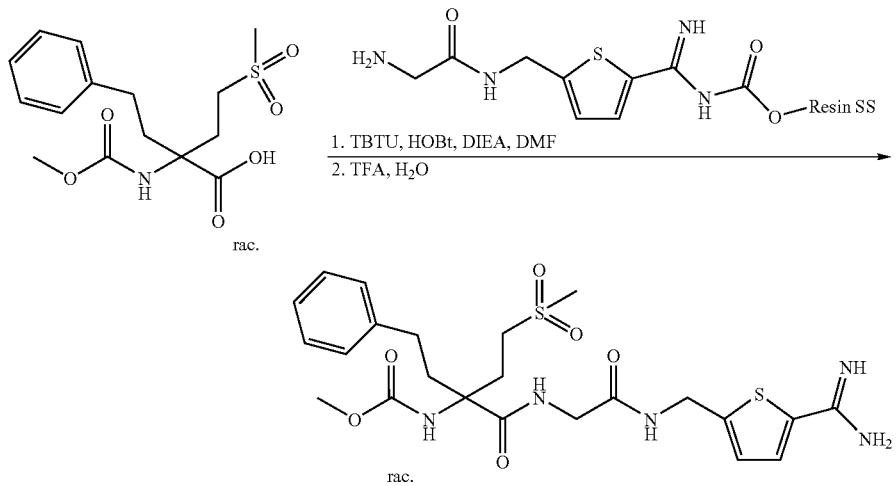

(±)-[1-({[(5-Carbamimidoyl-thiophen-2-ylmethyl)-carbamoyl]-methyl}-carbamoyl)-1-(2-methanesulfonyl-ethyl)-3-phenyl-propyl]-carbamic acid methyl ester. (Compound 5)

A suspension of (±)-4-methanesulfonyl-2-methoxycarbonylamino-2-phenethyl-butyric acid (46 mg, 0.134 mmol), thiophenoamidine bound resin (50 mg, 0.535 mmol/g), TBTU (47 mg, 0.15 mmol), HOBt (26 mg, 0.15 mmol), and DIEA (74 µL, 0.40 mmol) in DMF (2.0 mL) was shaken at rt overnight. DMF was removed by filtration and the resin washed. TFA/H$_2$O (95:5, 2 mL) was added and the suspension was further shaken for 3 h. The filtrate was then purified on HPLC (CH$_3$CN, H$_2$O, 0.1% TFA) to give a fluffy white solid as the title compound (11 mg, 89% for two steps), MS (electrospray) 538 (M+1);. $^1$H NMR (CD$_3$OD); 2.15 (m, 2H), 2.5 (m, 4H), 2.95 (s, 3H), 3.0–3.2 (m, 3H), 3.64 (s, 3H), 3.90 (m, 2H), 4.70 (m, 2H), 7.2–7.4 (m, 7H), 7.80 (d, J=3.0, 1H).

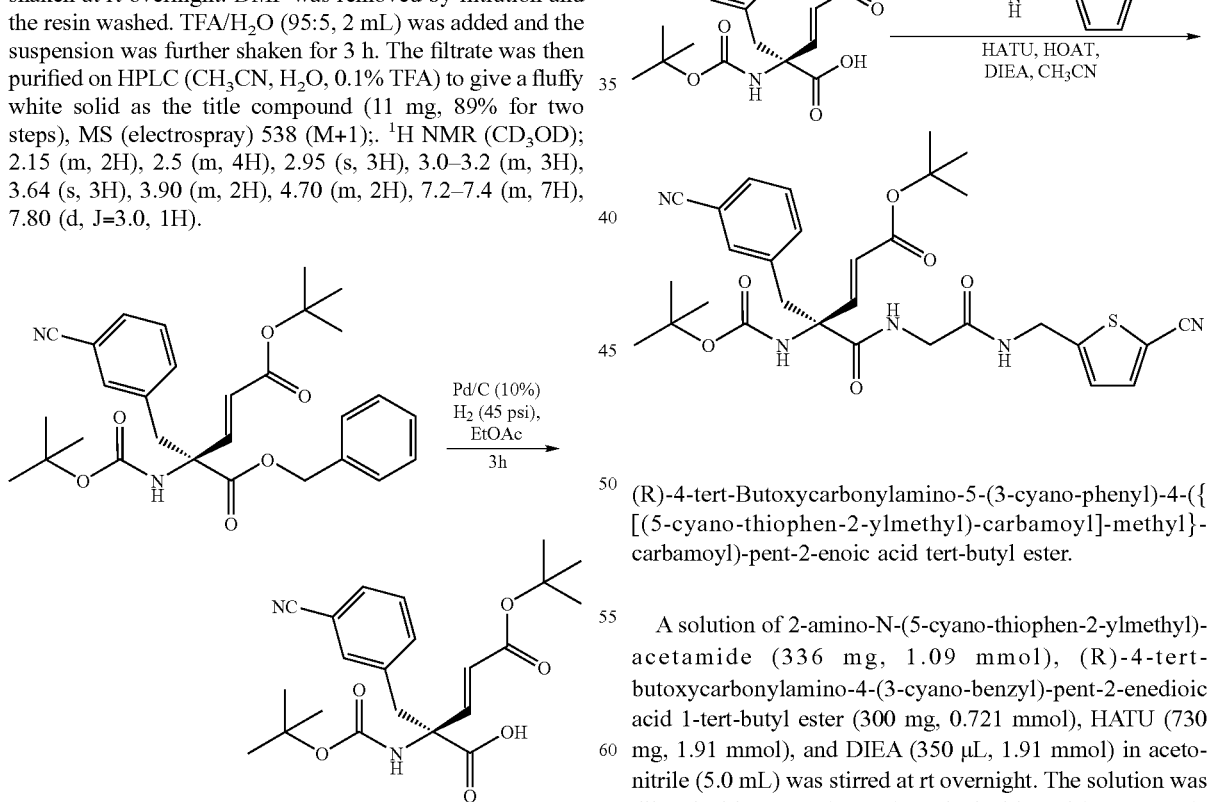

(R)-4-tert-Butoxycarbonylamino-4-(3-cyano-benzyl)-pent-2-enedioic acid 1-tert-butyl ester.

(R)-4-tert-Butoxycarbonylamino-4-(3-cyano-benzyl)-pent-2-enedioic acid 5-benzyl ester 1-tert-butyl ester (1.0 g, 1.98 mmol) was shaken with Pd (5% on carbon, 300 mg) in EtOAc (10 mL) under H$_2$ (50 psi) for 3 h. The solid was removed by filtration and the solvent evaporated in vacuo to give an oil corresponding to the title compound.

(R)-4-tert-Butoxycarbonylamino-5-(3-cyano-phenyl)-4-({[(5-cyano-thiophen-2-ylmethyl)-carbamoyl]-methyl}-carbamoyl)-pent-2-enoic acid tert-butyl ester.

A solution of 2-amino-N-(5-cyano-thiophen-2-ylmethyl)-acetamide (336 mg, 1.09 mmol), (R)-4-tert-butoxycarbonylamino-4-(3-cyano-benzyl)-pent-2-enedioic acid 1-tert-butyl ester (300 mg, 0.721 mmol), HATU (730 mg, 1.91 mmol), and DIEA (350 µL, 1.91 mmol) in acetonitrile (5.0 mL) was stirred at rt overnight. The solution was diluted with EtOAc (20 mL) washed with HCl (1M, 10 mL), NaHCO$_3$ (sat., 10 mL), brine (10 mL), and removed in vacuo to give an oil. Column chromatography (MeOH/CH$_2$Cl$_2$, 5:95) gave an oil corresponding to the title compound, MS (electrospray) 594 (M+1).

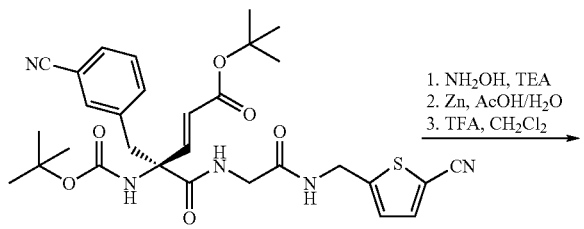

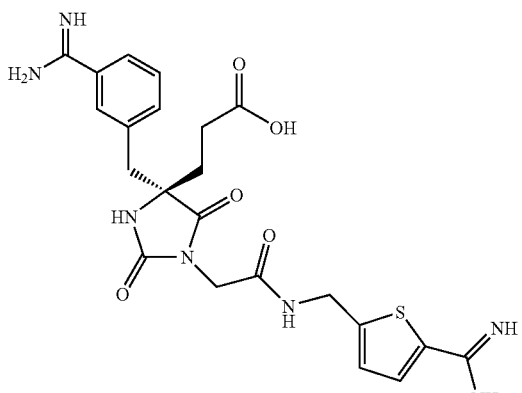

3(3-Amdn)Bn)-3(Carboxopropyl)Hydantion-MeCarbonly-(2-Amdn)thiophene-5-MeAm

To a stirring solution of MeOCO-(Me)E(α-(3-Amdn)Bn)-G-(4-Amdn)thiazole-2-MeAm (compound 2; preparation 5; p.41) in THF/H$_2$O (4:1) was added 1 M LiOH (4 eq). After 4 h, the reaction was concentrated in vacuo and purified by PP-HPLC using ACN/H$_2$O/TFA as eluent to afford the title compound as a colorless solid. MS (API, pos ion): 500 (M+H)$^+$, 250.6 (M+2H)$^+$.

(R)-4-Amino-5-(3-carbamimidoyl-phenyl)-4-({[(5-carbamimidoyl-thiophen-2-ylmethyl)-carbamoyl]-methyl}-carbamoyl)-pent-2-enoic acid. (Compound 6)

(R)-4-tert-Butoxycarbonylamino-5-(3-cyano-phenyl)-4-({[(5-cyano-thiophen-2-ylmethyl)-carbamoyl]-methyl}-carbamoyl)-pent-2-enoic acid tert-butyl ester (100 mg, 0.169 mmol) was added to NH$_2$OH (650 mg, 16.8 mmol) in MeOH (10 mL) and the mixture was stirred overnight. HPLC purification (CH$_3$CN, H$_2$O, 0.1% THF) gave a fluffy white solid as the 4-amino-5-[3-(N-hydroxycarbamimidoyl)-phenyl]-4-[({[5-(N-hydroxycarbamimidoyl)-thiophen-2-ylmethyl]-carbamoyl}-methyl)-carbamoyl]-pent-2-enoic acid, MS (electrospray) (M+1). This compound was added to a stirring Zinc dust (300 mg) in AcOH/H$_2$O (9:1, 5 mL) and the mixture stirred for 2 days. The solid was removed by filtration and the solvent evaporated in vacuo to give a solid. The residue was dissolved in TFA/CH$_2$Cl$_2$ (1:15 mL) and the resulting solution stirred for 3 h. HPLC purification (CH$_3$CN, H$_2$O, 0.1% TFA) gave a fluffy white solid as the title compound, MS (electrospray) 472 (M+1); 236 (M+2). $^1$H NMR (CD$_3$OD); 3.3–3.5 (m, 2H), 3.36 (m, 1H), 4.03 (m, 1H), 4.66 (m, 2H), 6.19 (d, J=12 Hz, 1H), 7.17 (m, 2H), 7.6–7.9 (m, 5H).

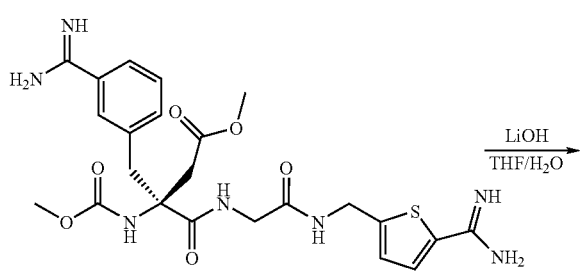

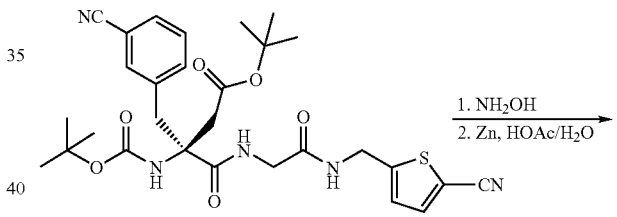

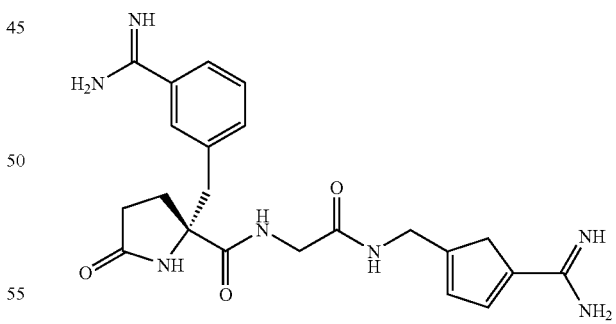

α-(3-Amdn)BnPyro-G-(2-Amdn)thiophene-5-MeAm

To a stirring solution of (R)-4-tert-butoxycarbonylamino-5-(3-cyano-phenyl)-4-({[(5-cyano-thiophen-2-ylmethyl]-carbamoyl)-pentanoic acid tert-butyl ester (100 mg, 0.17 mmol) in MeOH (10 ml) was added H$_2$NOH.HCl (230 mg, 20 eq) and N-methylmorpholine (0.45 ml, 20 eq). After stirring ovemite, the reaction was concentrated in vacuo and purified by RP-HPLC using ACN/H₂O/TFA as eluent to afford a colorless solid, which was added to a stirring suspension of Zinc dust (300 mg) in HOAc/H20 (9:1, 5 ml). After 2 days, the solid was removed by filtration and the filtrate was concentrated in vacuo. The residue was purified by RP-HPLC using ACN/H₂O/TFA as eluent to afford the title compound as a colorless solid. MS (API, pos ion): 456 $(M+H)^+$, 228.5 $(M+2H)^+$.

Table II lists the determined Ki values for certain of the enzymes listed above for certain compounds of the present invention and demonstrate the high degree of specificity for the inhibition of matriptase compared to the other serine proteases.

| Compound | Matriptase | Endothelin 1 | Endothelin 2 | FXa | Thrombin | Plasmin |
| --- | --- | --- | --- | --- | --- | --- |
| alpha-(3-amidinoBn)MeSO2-G-(2-Amdn)thiophene-5-MeAm | A | E | D | D | E | NT |
| alpha-(3-amidinoBn)MeSO2-G-(2-Amdn)thiophene-5-MeAm | A | F | F | D | D | E |
| alpha-(3-Amdn)BnPyro-G-(2-Amdn)thiophene-5-MeAm | A | F | E | E | D | D |
| MeOCO(t-Bu)E(R)(alpha-(3-Amdn)Bn)-G-(2-Amdn )thiophene-5-MeAm | A | F | E | D | E | E |
| 3(3-Amdn)Bn-3(Methsulfone)hydantoin-G-(2-Amdn)thiazole-2-MeAm | B | E | E | E | E | NT |
| (Me)E(alpha-(3-Amdn)Bn)-G-(2-Amdn)thiophene-5MeAm | B | NT | NT | NT | NT | NT |
| MeOCO-E(O-t-Butyl)(alpha-(3-Amdn)Bn)-G-(4-Amdn)BnAm | B | F | E | F | C | NT |
| N-MeOCO-(alpha-(3-Am)4-PyrMe)MeSO2-G-(2-Amdn)thiophene-5-MeAm | B | NT | NT | C | E | NT |
| E(alpha-(3-Amdn)Bn)-G-(2-Amdn)thiophene-5MeAm | B | F | E | D | D | D |
| alpha(3-amdn)Bn-2-3-dehydroE-G-(2-Amdn)thiophene-5-MeAm | B | F | E | D | D | D |
| MeOCO-(Me)E(alpha-(3-Amdn)Bn)-G-(4-Amdn)thiazole-2-MeAm | C | E | E | E | E | NT |
| iBoc-(Me)E(R)(alpha-(3-Amdn)Bn)-G-(2-Amdn)thiophene-5MeAm | C | NT | NT | NT | C | NT |

A = less than 100 nM,
B = 100 to 250 nM,
C = 250 to 500 nM,
D = 500 to 2500 nM,
E = Greater than 2500 nM,
F = Inactive,
NT = Not Tested It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A compound of the formula

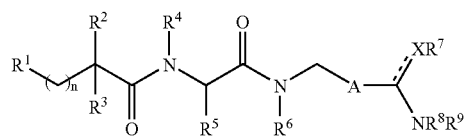

wherein:
$R^1$ is a member selected from the group consisting of an optionally substituted $C_1$–$C_8$ alkyl, an optionally substituted $C_1$–$C_8$ alkoxy, an optionally substituted $C_1$–$C_8$ alkoxycarbonylamino, an optionally substituted carboxy, an optionally substituted carboxyalkyl, an optionally substituted carboxyalkenyl, an optionally substituted $C_1$–$C_8$ alkanoyl, an optionally substituted carbamoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylalkyl, an optionally substituted $C_1$–$C_8$ alkylthio, an optionally substituted $C_1$–$C_8$ alkylsulfinyl, an optionally substituted $C_1$–$C_8$ alkylsulfonyl, an optionally substituted C₁–C₈ alkylsulfonylcarbamoyl, an optionally substituted aryl, an optionally substituted arylsulfinyl, an optionally substituted arylsulfonyl, an optionally substituted arylsulfonylcarbamoyl, an optionally substituted aralkylsulfonyl, an optionally substituted amino, and an acid isostere;

n is a value of 0 to about 6;

R² is a member selected from the group consisting of an optionally substituted aryl, an optionally substituted C₁–C₈ alkylcarbamoyl, an optionally substituted C₁–C₈ alkoxycarbonylamino, an optionally substituted C₁–C₈ alkoxycarbonyl, an optionally substituted C₁–C₈ alkoxycarbonylalkyl, an optionally substituted amino, an optionally substituted carbamoyl, an optionally substituted carboxyalkyl, an optionally substituted heteroaryl, an optionally substituted aralkyl, an optionally substituted heteroaralkyl, an optionally substituted heteroararyl, an optionally substituted cycloalkyl, an optionally substituted ureido, an optionally substituted sulfamoyl, an optionally substituted C₁–C₈ alkylsulfonylcarbamoyl, an optionally substituted arylsulfonylcarbamoyl, an optionally substituted heteroarylalkylsulfamoyl, an optionally substituted alkylsulfamoyl, an optionally substituted arylsulfamoyl, an optionally substituted heteroarylsulfamoyl, an optionally substituted aralkylsulfonylcarbamoyl and hydroxy; or R¹, R² and the atoms to which they are attached, join to form an optionally substituted 5- or 6-membered heterocyclic or carbocyclic ring;

R³ is a member selected from the group consisting of an optionally substituted aryl, an optionally substituted C₁–C₈ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group; or R¹ and R³, or R² and R³, together with the atoms to which they are attached, join to form an optionally substituted 5- or 6-membered heterocyclic or carbocyclic ring;

R⁴ is a member selected from the group consisting of hydrogen, an optionally substituted C₁–C₈ alkyl, and an optionally substituted aryl; or R³, R⁴, or R², R⁴ and the atoms to which they are attached, join to form an optionally substituted 5- or 6-membered heterocyclic or carbocyclic ring;

R⁵ is a member selected from the group consisting of hydrogen, an optionally substituted C₁–C₈ alkyl, and an optionally substituted aryl, an optionally substituted aralkyl, or, alternatively, R⁴, R⁵ and the atoms to which they are attached, join to form a 5- or 6-membered heterocyclic or heteroaryl ring;

R⁶ is a member selected from the group consisting of hydrogen, an optionally substituted C₁–C₈ alkyl, and an optionally substituted aryl; or R⁵, R⁶ and the atoms to which they are attached, join to form an optionally substituted 5- or 6-membered heterocyclic or carbocyclic ring;

'A' is a member selected from the group consisting of an optionally substituted C₁–C₈ alkylene, a five- or a six-membered optionally substituted cycloalkyl group, a 5 to 10-membered optionally substituted aryl group and a 5 to 10-membered optionally substituted heteroaryl group, wherein said 5 to 10-membered optionally substituted heteroaryl group has from 1 to 3 heteroatoms selected from the group consisting of optionally substituted N, O, and S, wherein 'A' can optionally have a heteroatom for attachment;

X is a heteroatom selected from the group consisting of S, O and N;

R⁷, if present, is a member selected from the group consisting of hydrogen, hydroxy, an optionally substituted C₁–C₈ alkyl, an optionally substituted C₁–C₈ alkoxy, an optionally substituted aryl, an optionally substituted C₁–C₈ alkanoyl, an optionally substituted C₁–C₈ alkanoyloxy, an optionally substituted alkylcarbamoyl, an optionally substituted alkoxycarbonyl, an optionally substituted C₁–C₈ alkoxycarbonyloxy; alternatively, A, R⁷, and the atoms to which they are attached, join to form a 5- to 10-membered optionally substituted heteroaryl group, wherein said 5- to 10-membered optionally substituted heteroaryl group has at least 1 optionally substituted nitrogen and the dotted line is either a bond or is absent; and R⁸ and R⁹ are members independently selected from the group consisting of hydrogen, hydroxy, an optionally substituted C₁–C₈ alkyl, an optionally substituted alkoxy, an optionally substituted aryl, an optionally substituted C₁–C₈ alkanoyl, an optionally substituted alkanoyloxy, an optionally substituted C₁–C₈ alkylcarbamoyl, an optionally substituted alkoxycarbonyl, and an optionally substituted C₁–C₈ alkoxycarbonyloxy, in an alternative embodiment, R⁷ and R⁹ and the atoms to which they are attached, join to form a 5- to 7-membered heterocyclic or heteroaryl ring.

2. The compound of claim 1, wherein

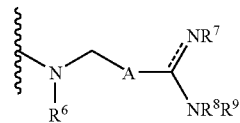

is a member selected from the group consisting of:

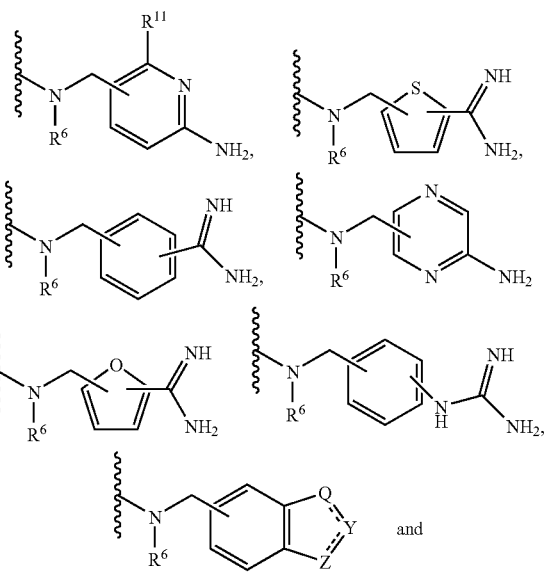

-continued

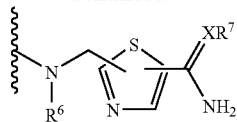

wherein $R^{11}$ is a member selected from the group consisting of hydrogen, hydroxyl, and an optionally substituted $C_1$–$C_8$ alkyl; and Q, Y and Z are each independently selected from the group consisting of an optionally substituted carbon, an optionally substituted nitrogen, an oxygen and a sulfur, provided however at least one of Q, Y and Z is carbon and wherein the dotted line is an optional double bond.

3. The compound of claim 2, wherein said compound has the formula

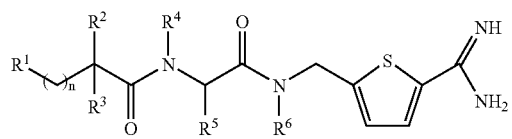

II wherein:

$R^1$ is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted amino, an optionally substituted carbamoyl, an optionally substituted $C_1$–$C_8$ alkylsulfonyl, an optionally substituted aryl, optionally substituted arylsulfonyl, and a carboxylic acid isostere;

n is a value of about 1 to 4;

$R^2$ is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted $C_1$–$C_8$ alkoxycarbonylamino, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy;

$R^3$ is a member selected from the group consisting of an optionally substituted aryl, an optionally substituted aralkyl, an optionally substituted $C_1$–$C_8$ alkoxycarbonyl, an optionally substituted heteroaralkyl, and an optionally substituted carboxy; and $R^5$ is a member selected from the group consisting of hydrogen, an optionally substituted $C_1$–$C_8$ alkyl, and an optionally substituted aryl.

4. The compound of claim 3, wherein said compound has the formula

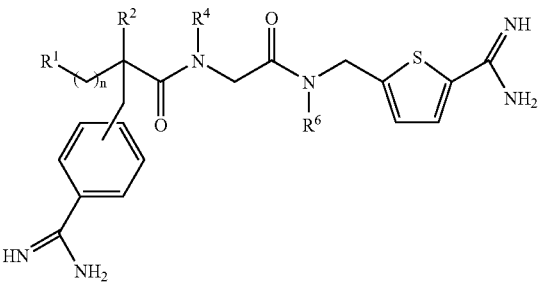

IIa wherein:

$R^1$ is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted amino, and an optionally substituted carboxy an optionally substituted carbamoyl, an optionally substituted $C_1$–$C_8$ alkylsulfonyl, an optionally substituted aralkylsulfonyl, optionally substituted arylsulfonyl, and an acid isostere;

n is a value of about 1 to 2;

$R^2$ is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted $C_1$–$C_8$ alkoxycarbonylamino, an optionally substituted carbamoyl, an optionally substituted ureido, an optionally substituted sulfamoyl, an optionally substituted $C_1$–$C_8$ alkylsulfonylcarbamoyl, an optionally substituted heteroarylalkylsulfamoyl, an optionally substituted alkylsulfamoyl, an optionally substituted arylsulfamoyl, an optionally substituted heteroarylsulfamoyl, an optionally substituted arylsulfonylcarbamoyl and hydroxy; and $R^6$ is a member selected from the group consisting of hydrogen, an optionally substituted $C_1$–$C_8$ alkyl, and an optionally substituted aryl.

5. The compound of claim 3, wherein $R^2$ is selected from an optionally substituted $C_1$–$C_8$ alkylcarbamoyl, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted ureido, an optionally substituted heteroarylalkylsulfamoyl, an optionally substituted alkylsulfamoyl, an optionally substituted arylsulfamoyl, an optionally substituted heteroarylsulfamoyl, and hydroxy.

6. The compound of claim 3, wherein $R^2$ is an optionally substituted $C_1$–$C_8$ alkoxycarbonyl.

7. The compound of claim 2, wherein said compound has the formula

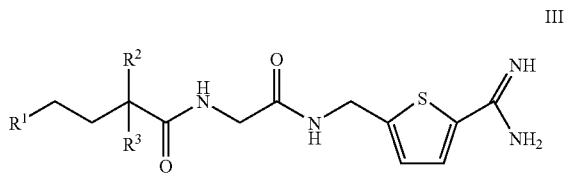

III wherein:
R¹ is a member selected from the group consisting of an $C_1$–$C_6$ alkyl, carboxyl group, $C_1$–$C_6$ alkyl-OC(O) NH—, $C_1$–$C_6$ alkylOC(O)—, $C_1$–$C_6$ alkylC(O)—, $C_1$–$C_6$ alkylSO$_2$—, $C_1$–$C_6$ alkylOC(O)NR$^{12}$ wherein R$^{12}$ is a member selected from the group consisting of hydrogen, an optionally substituted $C_1$–$C_8$ alkyl, and an optionally substituted aryl and NR$^{13}$R$^{14}$C(O)—, wherein R$^{13}$R$^{14}$ are each independently selected from the group of hydrogen, and an optionally substituted $C_1$–$C_8$ alkyl.

8. The compound of claim 7, wherein said compound has the formula

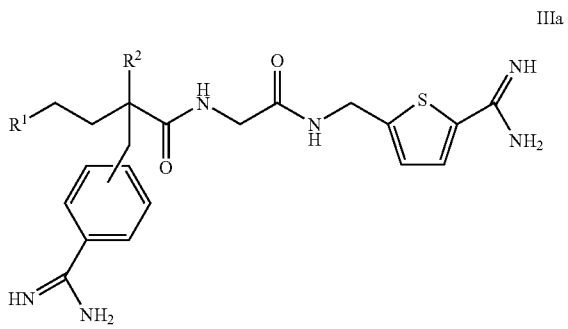

IIIa wherein:
R² is selected from an optionally substituted alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

9. The compound of claim 7, wherein said compound has the formula

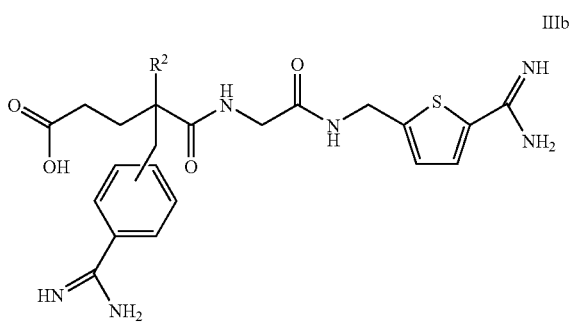

IIIb wherein:
R² is selected from an optionally substituted $C_1$–$C_6$ alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

10. The compound of claim 2, wherein said compound has the formula

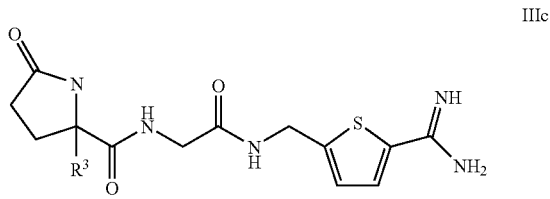

IIIc wherein:
R³ is a member selected from the group consisting of an optionally substituted aryl, an optionally substituted $C_1$–$C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroaryaryl, and an optionally substituted cycloalkyl group.

11. The compound of claim 2, wherein said compound has the formula

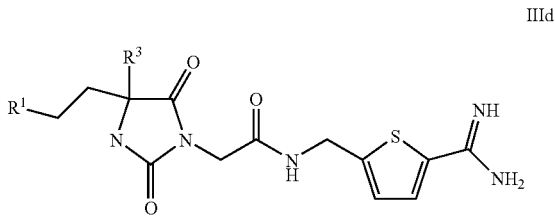

IIId wherein:
R¹ is a member selected from the group consisting of an optionally substituted $C_1$–$C_8$ alkyl, an optionally substituted $C_1$–$C_8$ alkoxy, an optionally substituted $C_1$–$C_8$ alkoxycarbonylamino, an optionally substituted carboxy, an optionally substituted carboxyalkyl, an optionally substituted carboxyalkenyl, an optionally substituted $C_1$–$C_8$ alkanoyl, an optionally substituted carbamoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylalkyl, an optionally substituted $C_1$–$C_8$ alkylthio, an optionally substituted $C_1$–$C_8$ alkylsulfinyl, an optionally substituted $C_1$–$C_8$ alkylsulfonyl, an optionally substituted $C_1$–$C_8$ alkylsulfonylcarbamoyl, an optionally substituted aryl, an optionally substituted arylsulfinyl, an optionally substituted arylsulfonyl, an optionally substituted arylsulfonylcarbamoyl, an optionally substituted aralkylsulfonyl, an optionally substituted amino, and an acid isostere;
R³ is a member selected from the group consisting of an optionally substituted aryl, an optionally substituted $C_1$–$C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group; or $R^2$ and $R^3$, together with the atoms to which they are attached, join to form an optionally substituted 5- or 6-membered heterocyclic or carbocylic ring.

12. The compound of claim 2, wherein said compound has the formula

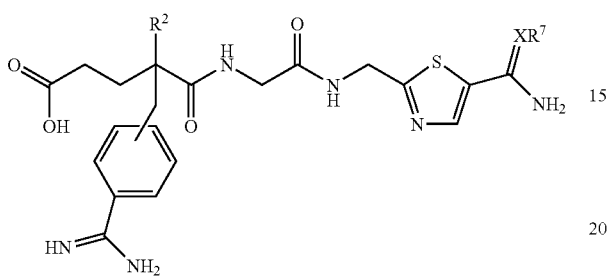

IIIe wherein:

$R^2$ is selected from an optionally substituted $C_1$–$C_6$ alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

13. The compound of claim 1, wherein said compound has the formula

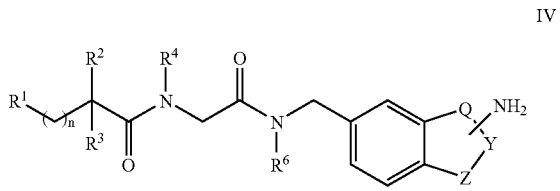

IV wherein:

$R^1$ is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted carbamoyl, an optionally substituted amino, and an optionally substituted carboxy;

n is a value of about 1 to 2;

$R^2$ is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy;

$R^3$ is a member selected from the group consisting of an optionally substituted aryl, an optionally substituted $C_1$–$C_8$ alkoxycarbonyl, and an optionally substituted carboxy; and $R^6$ is a member selected from the group consisting of hydrogen, an optionally substituted $C_1$–$C_8$ alkyl, and an optionally substituted aryl; and Q, Y and Z are each independently selected from the group consisting of a carbon, an optionally substituted nitrogen, an oxygen and a sulfur, provided however at least one of Q, Y and Z is carbon.

14. The compound of claim 13, wherein said compound has the formula

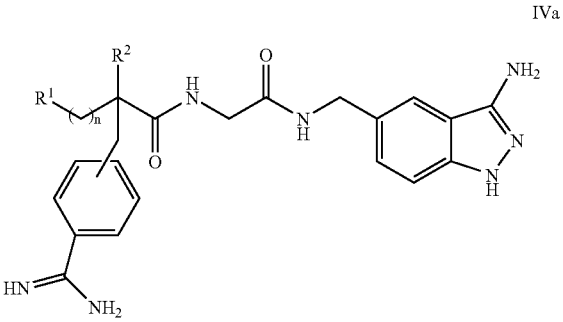

IVa wherein:

$R^1$ is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted carbamoyl, an optionally substituted amino, and an optionally substituted carboxy;

n is a value of about 1 to 2; and $R^2$ is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, and an optionally substituted carboxy, an optionally substituted $C_1$–$C_8$ alkoxycarbonylamino, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy.

15. A pharmaceutical composition, said pharmaceutical composition comprising:

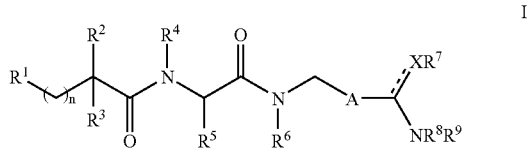

I wherein:

$R^1$ is a member selected from the group consisting of an optionally substituted $C_1$–$C_8$ alkyl, an optionally substituted $C_1$–$C_8$ alkoxy, an optionally substituted $C_1$–$C_8$ alkoxycarbonylamino, an optionally substituted carboxy, an optionally substituted carboxyalkyl, an optionally substituted carboxyalkenyl, an optionally substituted $C_1-C_8$ alkanoyl, an optionally substituted carbamoyl, an optionally substituted $C_1-C_8$ alkylcarbamoyl, an optionally substituted $C_1-C_8$ alkoxycarbonyl, an optionally substituted $C_1-C_8$ alkoxycarbonylalkyl, an optionally substituted $C_1-C_8$ alkylthio, an optionally substituted $C_1-C_8$ alkylsulfinyl, an optionally substituted $C_1-C_8$ alkylsulfonyl, an optionally substituted $C_1-C_8$ alkylsulfonylcarbamoyl, an optionally substituted aryl, an optionally substituted arylsulfinyl, an optionally substituted arylsulfonyl, an optionally substituted arylsulfonylcarbamoyl, an optionally substituted aralkylsulfonyl, an optionally substituted amino, and an acid isostere;

n is a value of 0 to about 6;

$R^2$ is a member selected from the group consisting of an optionally substituted aryl, an optionally substituted $C_1-C_8$ alkylcarbamoyl, an optionally substituted $C_1-C_8$ alkoxycarbonylamino, an optionally substituted $C_1-C_8$ alkoxycarbonyl, an optionally substituted $C_1-C_8$ alkoxycarbonylalkyl, an optionally substituted amino, an optionally substituted carbamoyl, an optionally substituted carboxyalkyl, an optionally substituted heteroaryl, an optionally substituted aralkyl, an optionally substituted heteroaralkyl, an optionally substituted heteroararyl, an optionally substituted cycloalkyl, an optionally substituted ureido, an optionally substituted sulfamoyl, an optionally substituted $C_1-C_8$ alkylsulfonylcarbamoyl, an optionally substituted arylsulfonylcarbamoyl, an optionally substituted heteroarylalkylsulfamoyl, an optionally substituted alkylsulfamoyl, an optionally substituted arylsulfamoyl, an optionally substituted heteroarylsulfamoyl, an optionally substituted aralkylsulfonylcarbamoyl and hydroxy; or $R^1$, $R^2$ and the atoms to which they are attached, join to form an optionally substituted 5- or 6-membered heterocyclic or carbocylic ring;

$R^3$ is a member selected from the group consisting of an optionally substituted aryl, an optionally substituted $C_1-C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group; or $R^1$ and $R^3$, or $R^2$ and $R^3$, together with the atoms to which they are attached, join to form an optionally substituted 5- or 6-membered heterocyclic or carbocylic ring;

$R^4$ is a member selected from the group consisting of hydrogen, an optionally substituted $C_1-C_8$ alkyl, and an optionally substituted aryl; or $R^3$, $R^4$, or $R^2$, $R^4$ and the atoms to which they are attached, join to form an optionally substituted 5- or 6-membered heterocyclic or carbocylic ring;

$R^5$ is a member selected from the group consisting of hydrogen, an optionally substituted $C_1-C_8$ alkyl, and an optionally substituted aryl, an optionally substituted aralkyl, or, alternatively, $R^4$, $R^5$ and the atoms to which they are attached, join to form a 5- or 6-membered heterocyclic or heteroaryl ring;

$R^6$ is a member selected from the group consisting of hydrogen, an optionally substituted $C_1-C_8$ alkyl, and an optionally substituted aryl; or $R^5$, $R^6$ and the atoms to which they are attached, join to form an optionally substituted 5- or 6-membered heterocyclic or carbocylic ring;

'A' is a member selected from the group consisting of an optionally substituted $C_1-C_8$ alkylene, a five- or a six-membered optionally substituted cycloalkyl group, a 5 to 10-membered optionally substituted aryl group and a 5 to 10-membered optionally substituted heteroaryl group, wherein said 5 to 10-membered optionally substituted heteroaryl group has from 1 to 3 heteroatoms selected from the group consisting of optionally substituted N, O, and S, wherein 'A' can optionally have a heteroatom for attachment;

X is a heteroatom selected from the group consisting of S, O and N;

$R^7$, if present, is a member selected from the group consisting of hydrogen, hydroxy, an optionally substituted $C_1-C_8$ alkyl, an optionally substituted $C_1-C_8$ alkoxy, an optionally substituted aryl, an optionally substituted $C_1-C_8$ alkanoyl, an optionally substituted $C_1-C_8$ alkanoyloxy, an optionally substituted alkylcarbamoyl, an optionally substituted alkoxycarbonyl, an optionally substituted $C_1-C_8$ alkoxycarbonyloxy; alternatively, A, $R^7$, and the atoms to which they are attached, join to form a 5- to 10-membered optionally substituted heteroaryl group, wherein said 5- to 10-membered optionally substituted heteroaryl group has at least 1 optionally substituted nitrogen and the dotted line is either a bond or is absent; and $R^8$ and $R^9$ are members independently selected from the group consisting of hydrogen, hydroxy, an optionally substituted $C_1-C_8$ alkyl, an optionally substituted alkoxy, an optionally substituted aryl, an optionally substituted $C_1-C_8$ alkanoyl, an optionally substituted alkanoyloxy, an optionally substituted $C_1-C_8$ alkylcarbamoyl, an optionally substituted alkoxycarbonyl, and an optionally substituted $C_1-C_8$ alkoxycarbonyloxy, in an alternative embodiment, $R^7$ and $R^9$ and the atoms to which they are attached, join to form a 5- to 7-membered heterocyclic or heteroaryl ring.

16. The composition of claim 15, wherein

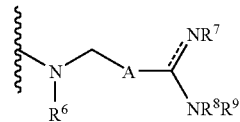

is a member selected from the group consisting of:

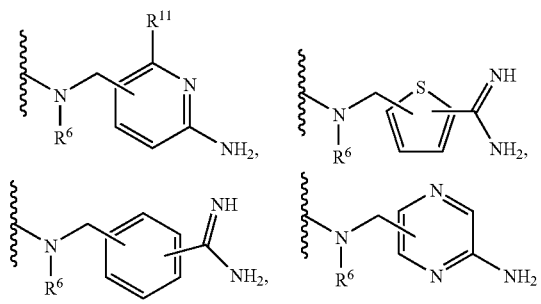

-continued

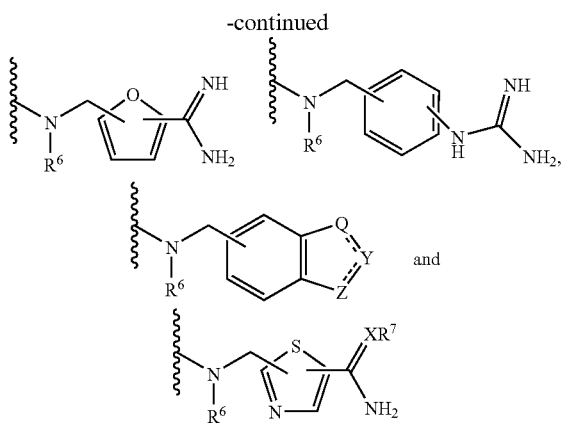

wherein $R^{11}$ is a member selected from the group consisting of hydrogen, hydroxyl, and an optionally substituted $C_1$–$C_8$ alkyl; and Q, Y and Z are each independently selected from the group consisting of an optionally substituted carbon, an optionally substituted nitrogen, an oxygen and a sulfur, provided however at least one of Q, Y and Z is carbon and wherein the dotted line is an optional double bond.

17. The composition of claim 16, wherein said compound has the formula

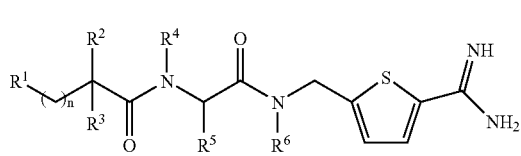

II wherein:

$R^1$ is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted amino, an optionally substituted carbamoyl, an optionally substituted $C_1$–$C_8$ alkylsulfonyl, an optionally substituted aryl, optionally substituted arylsulfonyl, and a carboxylic acid isostere;

n is a value of about 1 to 4;

$R^2$ is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted $C_1$–$C_8$ alkoxycarbonylamino, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy;

$R^3$ is a member selected from the group consisting of an optionally substituted aryl, an optionally substituted aralkyl, an optionally substituted $C_1$–$C_8$ alkoxycarbonyl, an optionally substituted heteroalkyl, and an optionally substituted carboxy; and $R^5$ is a member selected from the group consisting of hydrogen, an optionally substituted $C_1$–$C_8$ alkyl, and an optionally substituted aryl.

18. The composition of claim 17, wherein said compound has the formula

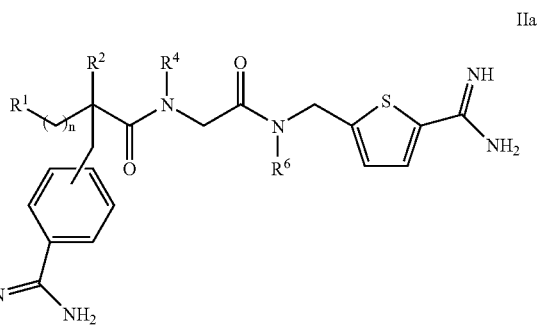

IIa wherein:

$R^1$ is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted amino, and an optionally substituted carboxy an optionally substituted carbamoyl, an optionally substituted $C_1$–$C_8$ alkylsulfonyl, an optionally substituted aralkylsulfonyl, optionally substituted arylsulfonyl, and an acid isostere;

n is a value of about 1 to 2;

$R^2$ is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted $C_1$–$C_8$ alkoxycarbonylamino, an optionally substituted carbamoyl, an optionally substituted ureido, an optionally substituted sulfamoyl, an optionally substituted $C_1$–$C_8$ alkylsulfonylcarbamoyl, an optionally substituted heteroarylalkylsulfamoyl, an optionally substituted alkylsulfamoyl, an optionally substituted arylsulfamoyl, an optionally substituted heteroarylsulfamoyl, an optionally substituted arylsulfonylcarbamoyl and hydroxy; and $R^6$ is a member selected from the group consisting of hydrogen, an optionally substituted $C_1$–$C_8$ alkyl, and an optionally substituted aryl.

19. The composition of claim 17, wherein $R^2$ is selected from an optionally substituted $C_1$–$C_8$ alkylcarbamoyl, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted ureido, an optionally substituted heteroarylalkylsulfamoyl, an optionally substituted alkylsulfamoyl, an optionally substituted arylsulfamoyl, an optionally substituted heteroarylsulfamoyl, and hydroxy.

20. The composition of claim 17, wherein $R^2$ is an optionally substituted $C_1$–$C_8$ alkoxycarbonyl.

21. The composition of claim 16, wherein said compound has the formula

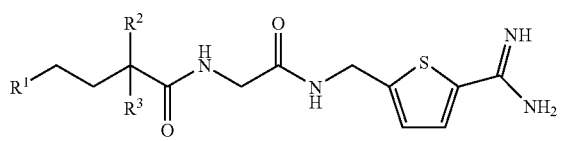

wherein:
R¹ is a member selected from the group consisting of an $C_1$–$C_6$ alkyl, carboxyl group, $C_1$–$C_6$ alkyl-OC(O)NH—, $C_1$–$C_6$ alkylOC(O)—, $C_1$–$C_6$ alkylC(O)—, $C_1$–$C_6$ alkylSO$_2$—, $C_1$–$C_6$ alkylOC(O)NR$^{12}$ wherein R$^{12}$ is a member selected from the group consisting of hydrogen, an optionally substituted $C_1$–$C_8$ alkyl, and an optionally substituted aryl and NR$^{13}$R$^{14}$C(O)—, wherein R$^{13}$R$^{14}$ are each independently selected from the group of hydrogen, and an optionally substituted $C_1$–$C_8$ alkyl.

22. The composition of claim 21, wherein said compound has the formula

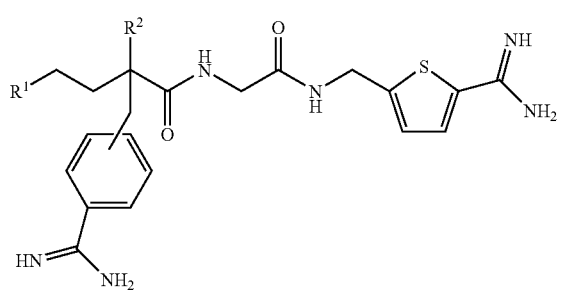

wherein:
R² is selected from an optionally substituted alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

23. The composition of claim 21, wherein said compound has the formula

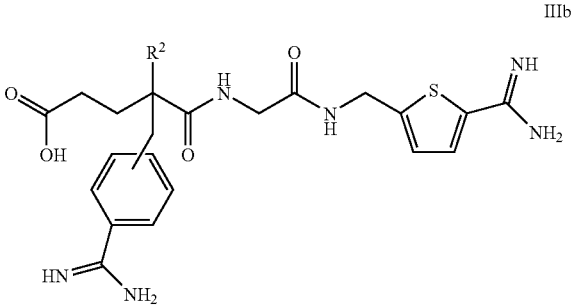

wherein:
R² is selected from an optionally substituted $C_1$–$C_6$ alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

24. The composition of claim 16, wherein said compound has the formula

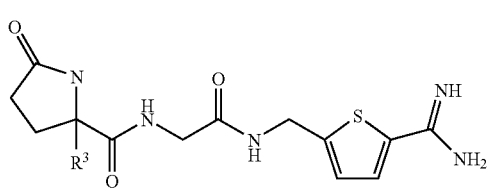

wherein:
R³ is a member selected from the group consisting of an optionally substituted aryl, an optionally substituted $C_1$–$C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group.

25. The composition of claim 16, wherein said compound has the formula

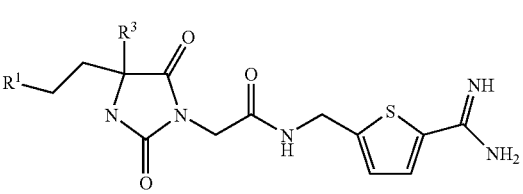

wherein:
R¹ is a member selected from the group consisting of an optionally substituted $C_1$–$C_8$ alkyl, an optionally substituted $C_1$–$C_8$ alkoxy, an optionally substituted $C_1$–$C_8$ alkoxycarbonylamino, an optionally substituted carboxy, an optionally substituted carboxyalkyl, an optionally substituted carboxyalkenyl, an optionally substituted $C_1$–$C_8$ alkanoyl, an optionally substituted carbamoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylalkyl, an optionally substituted $C_1$–$C_8$ alkylthio, an optionally substituted $C_1$–$C_8$ alkylsulfinyl, an optionally substituted $C_1$–$C_8$ alkylsulfonyl, an optionally substituted $C_1$–$C_8$ alkylsulfonylcarbamoyl, an optionally substituted aryl, an optionally substituted arylsulfinyl, an optionally substituted arylsulfonyl, an optionally substituted arylsulfonylcarbamoyl, an optionally substituted aralkylsulfonyl, an optionally substituted amino, and an acid isostere;
R³ is a member selected from the group consisting of an optionally substituted aryl, an optionally substituted $C_1$–$C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group; or $R^2$ and $R^3$, together with the atoms to which they are attached, join to form an optionally substituted 5- or 6-membered heterocyclic or carbocylic ring.

26. The composition of claim 16, wherein said compound has the formula

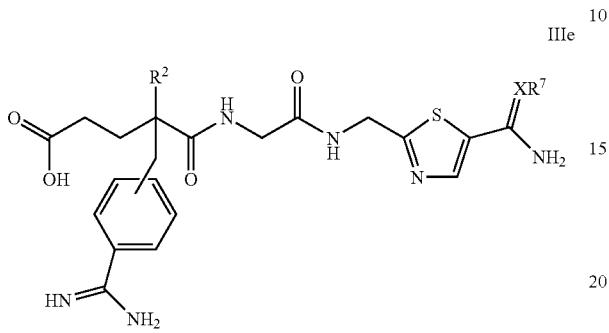

IIIe wherein:

$R^2$ is selected from an optionally substituted $C_1$–$C_6$ alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

27. The composition of claim 15, wherein said compound has the formula

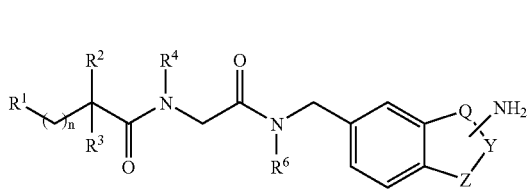

IV wherein:

$R^1$ is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted carbamoyl, an optionally substituted amino, and an optionally substituted carboxy;

n is a value of about 1 to 2;

$R^2$ is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy;

$R^3$ is a member selected from the group consisting of an optionally substituted aryl, an optionally substituted $C_1$–$C_8$ alkoxycarbonyl, and an optionally substituted carboxy; and $R^6$ is a member selected from the group consisting of hydrogen, an optionally substituted $C_1$–$C_8$ alkyl, and an optionally substituted aryl; and Q, Y and Z are each independently selected from the group consisting of a carbon, an optionally substituted nitrogen, an oxygen and a sulfur, provided however at least one of Q, Y and Z is carbon.

28. The composition of claim 27, wherein said compound has the formula

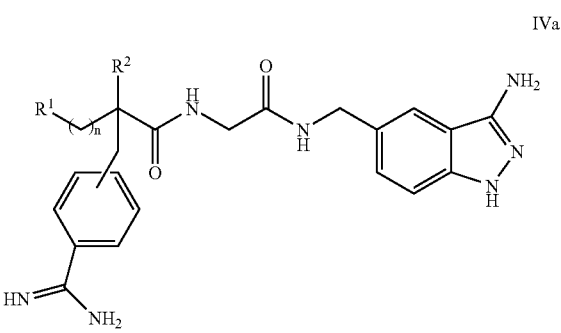

IVa wherein:

$R^1$ is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted carbamoyl, an optionally substituted amino, and an optionally substituted carboxy;

n is a value of about 1 to 2; and $R^2$ is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, and an optionally substituted carboxy, an optionally substituted $C_1$–$C_8$ alkoxycarbonylamino, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy.

29. A method for treating a condition in a mammal by decreasing or inhibiting the serine protease activity of matriptase or MTSP1, wherein the condition is selected from the group consisting of leukemia, lymphomas, breast cancer, gastrointestinal cancer, esophageal cancer, stomach cancer, colon cancer, bowel cancer, colorectal cancer, prostate cancer, bladder cancer, testicular cancer, ovarian cancer, uterine cancer, cervical cancer, brain cancer, lung cancer, bronchial cancer, pancreatic cancer, thyroid cancer, bone cancer and skin cancer, said method comprising: administering an effective amount of a compound of the formula:

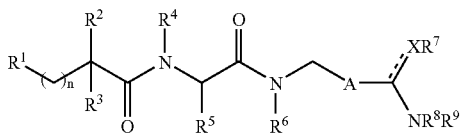

wherein:
R$^1$ is a member selected from the group consisting of an optionally substituted C$_1$–C$_8$ alkyl, an optionally substituted C$_1$–C$_8$ alkoxy, an optionally substituted C$_1$–C$_8$ alkoxycarbonylamino, an optionally substituted carboxy, an optionally substituted carboxyalkyl, an optionally substituted carboxyalkenyl, an optionally substituted C$_1$–C$_8$ alkanoyl, an optionally substituted carbamoyl, an optionally substituted C$_1$–C$_8$ alkylcarbamoyl, an optionally substituted C$_1$–C$_8$ alkoxycarbonyl, an optionally substituted C$_1$–C$_8$ alkoxycarbonylalkyl, an optionally substituted C$_1$–C$_8$ alkylthio, an optionally substituted C$_1$–C$_8$ alkylsulfinyl, an optionally substituted C$_1$–C$_8$ alkylsulfonyl, an optionally substituted C$_1$–C$_8$ alkylsulfonylcarbamoyl, an optionally substituted aryl, an optionally substituted arylsulfinyl, an optionally substituted arylsulfonyl, an optionally substituted arylsulfonylcarbamoyl, an optionally substituted aralkylsulfonyl, an optionally substituted amino, and an acid isostere;

n is a value of 0 to about 6;

R$^2$ is a member selected from the group consisting of an optionally substituted aryl, an optionally substituted C$_1$–C$_8$ alkylcarbamoyl, an optionally substituted C$_1$–C$_8$ alkoxycarbonylamino, an optionally substituted C$_1$–C$_8$ alkoxycarbonyl, an optionally substituted C$_1$–C$_8$ alkoxycarbonylalkyl, an optionally substituted amino, an optionally substituted carbamoyl, an optionally substituted carboxyalkyl, an optionally substituted heteroaryl, an optionally substituted aralkyl, an optionally substituted heteroaralkyl, an optionally substituted heteroararyl, an optionally substituted cycloalkyl, an optionally substituted ureido, an optionally substituted sulfamoyl, an optionally substituted C$_1$–C$_8$ alkylsulfonylcarbamoyl, an optionally substituted arylsulfonylcarbamoyl, an optionally substituted heteroarylalkylsulfamoyl, an optionally substituted alkylsulfamoyl, an optionally substituted arylsulfamoyl, an optionally substituted heteroarylsulfamoyl, an optionally substituted aralkylsulfonylcarbamoyl and hydroxy; or R$^1$, R$^2$ and the atoms to which they are attached, join to form an optionally substituted 5- or 6-membered heterocyclic or carbocyclic ring;

R$^3$ is a member selected from the group consisting of an optionally substituted aryl, an optionally substituted C$_1$–C$_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group; or R$^1$ and R$^3$, or R$^2$ and R$^3$, together with the atoms to which they are attached, join to form an optionally substituted 5- or 6-membered heterocyclic or carbocyclic ring;

R$^4$ is a member selected from the group consisting of hydrogen, an optionally substituted C$_1$–C$_8$ alkyl, and an optionally substituted aryl; or R$^3$, R$^4$, or R$^2$, R$^4$ and the atoms to which they are attached, join to form an optionally substituted 5- or 6-membered heterocyclic or carbocyclic ring;

R$^5$ is a member selected from the group consisting of hydrogen, an optionally substituted C$_1$–C$_8$ alkyl, and an optionally substituted aryl, an optionally substituted aralkyl, or, alternatively, R$^4$, R$^5$ and the atoms to which they are attached, join to form a 5- or 6-membered heterocyclic or heteroaryl ring;

R$^6$ is a member selected from the group consisting of hydrogen, an optionally substituted C$_1$–C$_8$ alkyl, and an optionally substituted aryl; or R$^5$, R$^6$ and the atoms to which they are attached, join to form an optionally substituted 5- or 6-membered heterocyclic or carbocyclic ring;

'A' is a member selected from the group consisting of an optionally substituted C$_1$–C$_8$ alkylene, a five- or a six-membered optionally substituted cycloalkyl group, a 5 to 10-membered optionally substituted aryl group and a 5 to 10-membered optionally substituted heteroaryl group, wherein said 5 to 10-membered optionally substituted heteroaryl group has from 1 to 3 heteroatoms selected from the group consisting of optionally substituted N, O, and S, wherein 'A' can optionally have a heteroatom for attachment;

X is a heteroatom selected from the group consisting of S, O and N;

R$^7$, if present, is a member selected from the group consisting of hydrogen, hydroxy, an optionally substituted C$_1$–C$_8$ alkyl, an optionally substituted C$_1$–C$_8$ alkoxy, an optionally substituted aryl, an optionally substituted C$_1$–C$_8$ alkanoyl, an optionally substituted C$_1$–C$_8$ alkanoyloxy, an optionally substituted alkylcarbamoyl, an optionally substituted alkoxycarbonyl, an optionally substituted C$_1$–C$_8$ alkoxycarbonyloxy; alternatively, A, R$^7$, and the atoms to which they are attached, join to form a 5- to 10-membered optionally substituted heteroaryl group, wherein said 5- to 10-membered optionally substituted heteroaryl group has at least 1 optionally substituted nitrogen and the dotted line is either a bond or is absent; and R$^8$ and R$^9$ are members independently selected from the group consisting of hydrogen, hydroxy, an optionally substituted C$_1$–C$_8$ alkyl, an optionally substituted alkoxy, an optionally substituted aryl, an optionally substituted C$_1$–C$_8$ alkanoyl, an optionally substituted alkanoyloxy, an optionally substituted C$_1$–C$_8$ alkylcarbamoyl, an optionally substituted alkoxycarbonyl, and an optionally substituted C$_1$–C$_8$ alkoxycarbonyloxy, in an alternative embodiment, R$^7$ and R$^9$ and the atoms to which they are attached, join to form a 5- to 7-membered heterocyclic or heteroaryl ring, to decrease or inhibit the serine protease activity of matriptase or MTSP1.

30. The method of claim 29, wherein

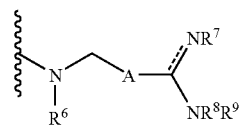

is a member selected from the group consisting of:

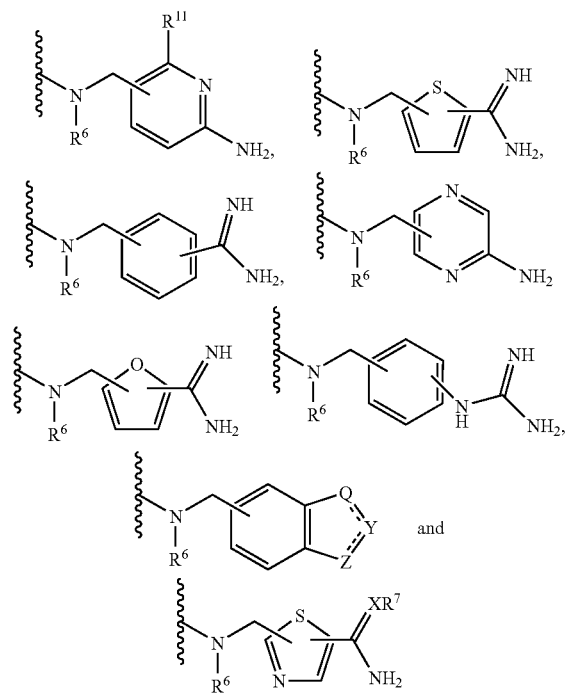

wherein R[11] is a member selected from the group consisting of hydrogen, hydroxyl, and an optionally substituted $C_1$–$C_8$ alkyl; and Q, Y and Z are each independently selected from the group consisting of an optionally substituted carbon, an optionally substituted nitrogen, an oxygen and a sulfur, provided however at least one of Q, Y and Z is carbon and wherein the dotted line is an optional double bond.

31. The method of claim 30, wherein said compound has the formula

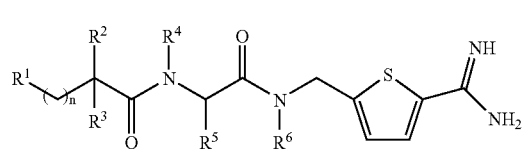

II wherein:
- R[1] is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted amino, an optionally substituted carbamoyl, an optionally substituted $C_1$–$C_8$ alkylsulfonyl, an optionally substituted aryl, optionally substituted arylsulfonyl, and a carboxylic acid isostere;
- n is a value of about 1 to 4;
- R[2] is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted $C_1$–$C_8$ alkoxycarbonylamino, an optionally substituted ureido, an optionally substituted sulfamoyl, an optionally substituted $C_1$–$C_8$ alkylsulfonylcarbamoyl, an optionally substituted arylsulfonylcarbamoyl, an optionally substituted aralkylsulfonylcarbamoyl and hydroxy;
- R[3] is a member selected from the group consisting of an optionally substituted aryl, an optionally substituted aralkyl, an optionally substituted $C_1$–$C_8$ alkoxycarbonyl, an optionally substituted heteroaralkyl, and an optionally substituted carboxy; and
- R[5] is a member selected from the group consisting of hydrogen, an optionally substituted $C_1$–$C_8$ alkyl, and an optionally substituted aryl.

32. The method of claim 31, wherein said compound has the formula

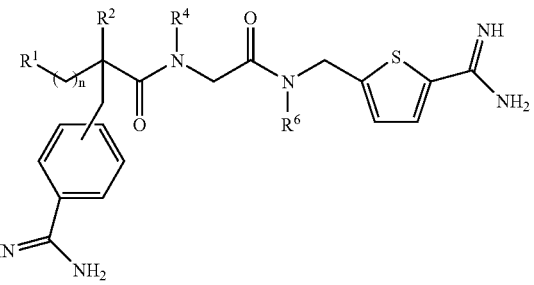

IIa wherein:
- R[1] is a member selected from the group consisting of an optionally substituted $C_1$–$C_8$ alkoxy, an optionally substituted carboxy, an optionally substituted $C_1$–$C_8$ alkanoyl, an optionally substituted $C_1$–$C_8$ alkylcarbamoyl, an optionally substituted $C_1$–$C_8$ alkoxycarbonyl, an optionally substituted $C_1$–$C_8$ alkoxycarbonylamino, an optionally substituted amino, and an optionally substituted carboxy an optionally substituted carbamoyl, an optionally substituted $C_1$–$C_8$ alkylsulfonyl, an optionally substituted aralkylsulfonyl, optionally substituted arylsulfonyl, and an acid isostere;
- n is a value of about 1 to 2;
- R[2] is a member selected from the group consisting of an optionally substituted aryl, an optionally substituted $C_1$–$C_8$ alkylcarbamoyl, an optionally substituted $C_1$–$C_8$ alkoxycarbonyl, an optionally substituted amino, an optionally substituted carboxy, an optionally substituted $C_1$–$C_8$ alkoxycarbonylamino, an optionally substituted carbamoyl, an optionally substituted ureido, an optionally substituted sulfamoyl, an optionally substituted $C_1$–$C_8$ alkylsulfonylcarbamoyl, an optionally substituted heteroarylalkylsulfonamide, an optionally substituted arylsulfonylcarbamoyl and hydroxy; and
- R[6] is a member selected from the group consisting of hydrogen, an optionally substituted $C_1$–$C_8$ alkyl, and an optionally substituted aryl.

33. The method of claim 31, wherein R[2] is selected from an optionally substituted $C_1$–$C_8$ alkylcarbamoyl, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted ureido, an optionally substituted heteroarylalkylsulfamoyl, an optionally substituted alkylsulfamoyl, an optionally substituted arylsulfamoyl, an optionally substituted heteroarylsulfamoyl, and hydroxy.

34. The method of claim 31, wherein $R^2$ is an optionally substituted $C_1$–$C_8$ alkoxycarbonyl.

35. The method of claim 30, wherein said compound has the formula

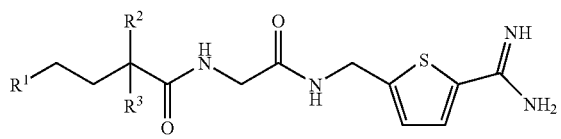

III wherein:

$R^1$ is a member selected from the group consisting of an $C_1$–$C_6$ alkyl, carboxyl group, $C_1$–$C_6$ alkyl-OC(O)NH—, $C_1$–$C_6$ alkylOC(O)—, $C_1$–$C_6$ alkylC(O)—, $C_1$–$C_6$ alkylSO$_2$—, $C_1$–$C_6$ alkylOC(O)NR$^{12}$ wherein $R^{12}$ is a member selected from the group consisting of hydrogen, an optionally substituted $C_1$–$C_8$ alkyl, and an optionally substituted aryl and NR$^{13}$R$^{14}$C(O)—, wherein $R^{13}$R$^{14}$ are each independently selected from the group of hydrogen, and an optionally substituted $C_1$–$C_8$ alkyl.

36. The method of claim 35, wherein said compound has the formula

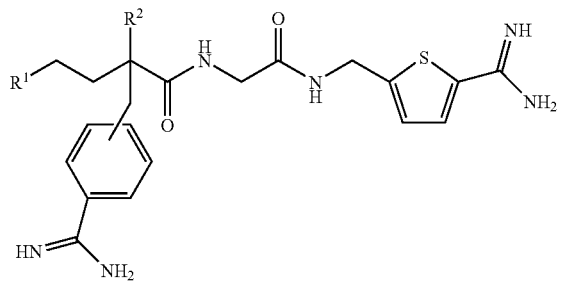

IIIa wherein:

$R^2$ is selected from an optionally substituted alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

37. The method of claim 35, wherein said compound has the formula

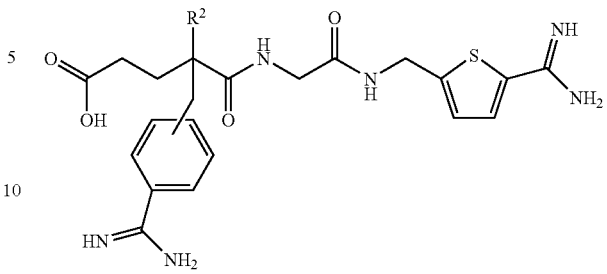

IIIb wherein:

$R^2$ is selected from an optionally substituted $C_1$–$C_6$ alkylcarbamoyl group, an optionally substituted $C_1$–$C_8$ alkoxycarbonylamino, an optionally substituted $C_1$–$C_8$ alkylsulfonylcarbamoyl, an optionally substituted aralkylsulfonylcarbamoyl, an optionally substituted carbamoyl, an optionally substituted heteroarylalkylsulfamoyl, an optionally substituted alkylsulfamoyl, an optionally substituted arylsulfamoyl, an optionally substituted heteroarylsulfamoyl, and an optionally substituted ureido.

38. The method of claim 30, wherein said compound has the formula

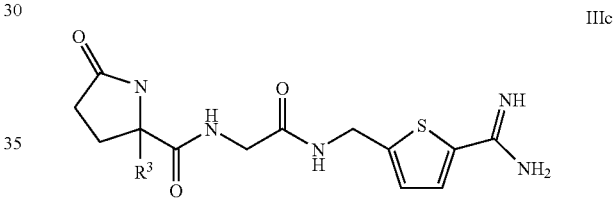

IIIc wherein:

$R^3$ is a member selected from the group consisting of an optionally substituted aryl, an optionally substituted $C_1$–$C_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroararyl, and an optionally substituted cycloalkyl group.

39. The method of claim 30, wherein said compound has the formula

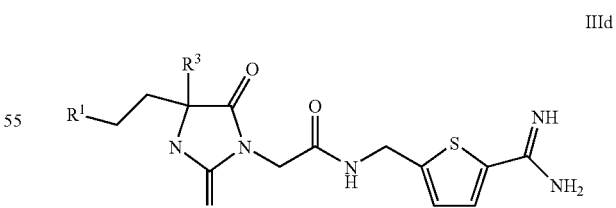

IIId wherein:

$R^1$ is a member selected from the group consisting of an optionally substituted $C_1$–$C_8$ alkyl, an optionally substituted $C_1$–$C_8$ alkoxy, an optionally substituted $C_1$–$C_8$ alkoxycarbonylamino, an optionally substituted carboxy, an optionally substituted carboxyalkyl, an optionally substituted carboxyalkenyl, an optionally substituted C$_1$–C$_8$ alkanoyl, an optionally substituted carbamoyl, an optionally substituted C$_1$–C$_8$ alkylcarbamoyl, an optionally substituted C$_1$–C$_8$ alkoxycarbonyl, an optionally substituted C$_1$–C$_8$ alkoxycarbonylalkyl, an optionally substituted C$_1$–C$_8$ alkylthio, an optionally substituted C$_1$–C$_8$ alkylsulfinyl, an optionally substituted C$_1$–C$_8$ alkylsulfonyl, an optionally substituted C$_1$–C$_8$ alkylsulfonylcarbamoyl, an optionally substituted aryl, an optionally substituted arylsulfinyl, an optionally substituted arylsulfonyl, an optionally substituted arylsulfonylcarbamoyl, an optionally substituted aralkylsulfonyl, an optionally substituted amino, and an acid isostere;

R$^3$ is a member selected from the group consisting of an optionally substituted aryl, an optionally substituted C$_1$–C$_8$ alkoxycarbonyl, an optionally substituted carboxyalkyl, an optionally substituted heteroaryl, an optionally substituted aralkyl, an optionally substituted heteroaralkyl, an optionally substituted heteroaralkenyl, an optionally substituted heteroaralkenyl, an optionally substituted heteroararyl, and an optionally substituted cycloalkyl group; or R$^2$ and R$^3$, together with the atoms to which they are attached, join to form an optionally substituted 5- or 6-membered heterocyclic or carbocylic ring.

40. The method of claim 30, wherein said compound has the formula

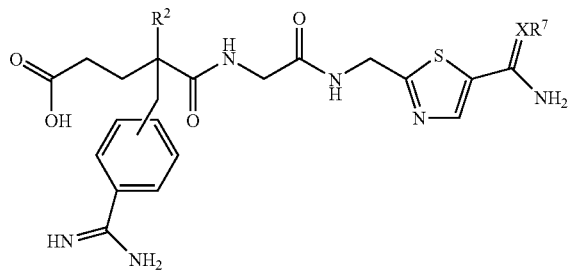

IIIe wherein:

R$^2$ is selected from an optionally substituted C$_1$–C$_6$ alkylcarbamoyl group, an optionally substituted C$_1$–C$_8$ alkoxycarbonylamino, an optionally substituted C$_1$–C$_8$ alkylsulfonylcarbamoyl, an optionally substituted aralkylsulfonylcarbamoyl, an optionally substituted carbamoyl, an optionally substituted heteroarylalkylsulfonamide, and an optionally substituted ureido.

41. The method of claim 29, wherein said compound has the formula

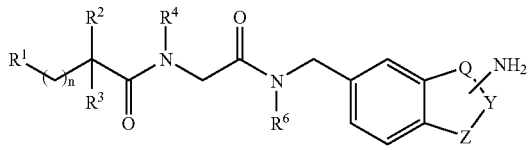

IV wherein:

R$^1$ is a member selected from the group consisting of an optionally substituted C$_1$–C$_8$ alkoxy, an optionally substituted carboxy, an optionally substituted C$_1$–C$_8$ alkanoyl, an optionally substituted C$_1$–C$_8$ alkylcarbamoyl, an optionally substituted C$_1$–C$_8$ alkoxycarbonyl, an optionally substituted C$_1$–C$_8$ alkoxycarbonylamino, an optionally substituted carbamoyl, an optionally substituted amino, and an optionally substituted carboxy;

n is a value of about 1 to 2;

R$^2$ is a member selected from the group consisting of an optionally substituted aryl, an optionally substituted C$_1$–C$_8$ alkylcarbamoyl, an optionally substituted C$_1$–C$_8$ alkoxycarbonyl, an optionally substituted amino, an optionally substituted carboxy, an optionally substituted ureido, an optionally substituted sulfamoyl, an optionally substituted C$_1$–C$_8$ alkylsulfonylcarbamoyl, an optionally substituted arylsulfonylcarbamoyl, an optionally substituted aralkylsulfonylcarbamoyl and hydroxy;

R$^3$ is a member selected from the group consisting of an optionally substituted aryl, an optionally substituted C$_1$–C$_8$ alkoxycarbonyl, and an optionally substituted carboxy; and R$^6$ is a member selected from the group consisting of hydrogen, an optionally substituted C$_1$–C$_8$ alkyl, and an optionally substituted aryl; and Q, Y and Z are each independently selected from the group consisting of a carbon, an optionally substituted nitrogen, an oxygen and a sulfur, provided however at least one of Q, Y and Z is carbon.

42. The method of claim 41, wherein said compound has the formula

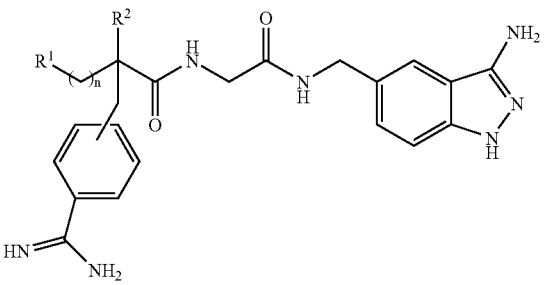

IVa wherein:

R$^1$ is a member selected from the group consisting of an optionally substituted C$_1$–C$_8$ alkoxy, an optionally substituted carboxy, an optionally substituted C$_1$–C$_8$ alkanoyl, an optionally substituted C$_1$–C$_8$ alkylcarbamoyl, an optionally substituted C$_1$–C$_8$ alkoxycarbonyl, an optionally substituted C$_1$–C$_8$ alkoxycarbonylamino, an optionally substituted carbamoyl, an optionally substituted amino, and an optionally substituted carboxy;

n is a value of about 1 to 2; and

R$^2$ is a member selected from the group consisting of an optionally substituted aryl, an optionally substituted C$_1$–C$_8$ alkylcarbamoyl, an optionally substituted C$_1$–C$_8$ alkoxycarbonyl, an optionally substituted amino, and an optionally substituted carboxy, an optionally substituted C$_1$–C$_8$ alkoxycarbonylamino, an optionally substituted ureido, an optionally substituted sulfamoyl, an optionally substituted C$_1$–C$_8$ alkylsulfonylcarbamoyl, an optionally substituted arylsulfonylcarbamoyl, an optionally substituted aralkylsulfonylcarbamoyl and hydroxy.

* * * * *